US008785727B2

(12) United States Patent
Bauer et al.

(10) Patent No.: US 8,785,727 B2
(45) Date of Patent: Jul. 22, 2014

(54) DESATURASE AND METHOD FOR THE PRODUCTION OF POLYUNSATURATED FATTY ACIDS IN TRANSGENIC ORGANISMS

(75) Inventors: Joerg Bauer, Teltow (DE); Johnathan A. Napier, Preston Hertfordshire (GB); Olga Sayanova, St. Albans Hertfordshire (GB)

(73) Assignee: Rothamsted Research Ltd., Hertfordshire (GB)

( * ) Notice: Subject to any disclaimer, the term of this patent is extended or adjusted under 35 U.S.C. 154(b) by 575 days.

(21) Appl. No.: 12/990,492

(22) PCT Filed: Apr. 29, 2009

(86) PCT No.: PCT/EP2009/055210
§ 371 (c)(1),
(2), (4) Date: Feb. 15, 2011

(87) PCT Pub. No.: WO2009/133145
PCT Pub. Date: Nov. 5, 2009

(65) Prior Publication Data
US 2011/0138490 A1 Jun. 9, 2011

(30) Foreign Application Priority Data

Apr. 30, 2008 (EP) .................................. 08155461

(51) Int. Cl.
*C12P 7/64* (2006.01)
*C12N 9/02* (2006.01)
*C12N 15/00* (2006.01)
*C07H 21/04* (2006.01)
*A01H 5/00* (2006.01)
*C12N 15/82* (2006.01)
*C12N 5/14* (2006.01)
*A23K 1/165* (2006.01)
*C11B 1/00* (2006.01)

(52) U.S. Cl.
USPC ........ 800/281; 435/134; 435/189; 435/320.1; 435/419; 536/23.2; 536/23.7; 426/52; 426/417; 800/295

(58) Field of Classification Search
None
See application file for complete search history.

(56) References Cited

U.S. PATENT DOCUMENTS

| 5,614,393 | A | 3/1997 | Thomas et al. | |
|---|---|---|---|---|
| 6,043,411 | A | 3/2000 | Nishizawa et al. | |
| 2006/0094091 | A1* | 5/2006 | Macool et al. | 435/134 |

FOREIGN PATENT DOCUMENTS

| EP | 0 550 162 A1 | 7/1993 |
|---|---|---|
| EP | 0 794 250 A1 | 9/1997 |
| WO | WO 91/13972 | 9/1991 |
| WO | WO 93/06712 | 4/1993 |
| WO | WO 93/11245 | 6/1993 |
| WO | WO 94/11516 | 5/1994 |
| WO | WO 94/18337 | 8/1994 |
| WO | WO 95/18222 | 7/1995 |
| WO | WO 96/21022 | 7/1996 |
| WO | WO 97/21340 | 6/1997 |
| WO | WO 97/30582 | 8/1997 |
| WO | WO 98/46763 | 10/1998 |
| WO | WO 98/46764 | 10/1998 |
| WO | WO 98/46765 | 10/1998 |
| WO | WO 98/46776 | 10/1998 |
| WO | WO 99/27111 | 6/1999 |
| WO | WO 99/64616 | 12/1999 |
| WO | WO 00/21557 | 4/2000 |
| WO | WO 02/081668 A2 | 10/2002 |
| WO | WO 2005/103253 A1 | 11/2005 |
| WO | WO 2007/093776 A2 | 8/2007 |

OTHER PUBLICATIONS

Torres-Guzman and Dominguez 1997 Molecular and Cellular Biology Nov: p. 6283-6293.*
Bell and Pond 1996 Phytochemistry 41:2 p. 465-471.*
Domergue et al., "Cloning and Functional Characterization of Phaeodactylum tricornutum front-end desaturases involved in eicosapentaenoic acid biosynthesis," *Eur. J. Biochem.*, vol. 269, pp. 4105-4113 (2002).
Horrocks et al., "Health Benefits of Docosahexaenoic Acid (DHA)," *Pharmacological Research*, vol. 40, No. 3, pp. 211-225 (1999).
Huang et al., "Cloning of Δ12- and Δ6-Desaturases from Mortierella alpine and Recombinant Production of γ-Linolenic Acid in *Saccharomyces cerevisiae*," *Lipids*, vol. 34, No. 7, pp. 649-659 (1999).
Sakuradani et al., "Δ6-Fatty acid desaturase from an arachidonic acid-producing *Mortierella* fungus; Gene cloning and its heterologous expression in a fungas, *Aspergillus*," gene vol. 238, pp. 445-453 (1999).
Sprecher, "Metabolism of highly unsaturated n-3 and n-6 fatty acids," *Biochimica et Biophysica Acta*, vol. 1486, pp. 219-231 (2000).
Stukey et al., "The OLE1 Gene of *Saccharomyces cerevisiae* Encodes the Δ9 Fatty Acid Desaturase and Can Be Functionally Replaced by the Rat Stearoyl-CoA Desaturase Gene," *The Journ. of Biological Chem.*, vol. 265, No. 33, pp. 20144-20149 (1990).

(Continued)

Primary Examiner — David T Fox
Assistant Examiner — Matthew Keogh
(74) Attorney, Agent, or Firm — Foley & Lardner LLP

(57) ABSTRACT

The present invention relates to a polynucleotide from *Emiliana huxleyi* which codes for a desaturase and which can be employed for the recombinant production of polyunsaturated fatty acids. The invention furthermore relates to vectors, host cells and transgenic nonhuman organisms which comprise the polynucleotide according to the invention, and to the polypeptides encoded by the polynucleotide. The invention furthermore relates to antibodies against the polypeptide according to the invention. Finally, the invention also relates to production methods for the polyunsaturated fatty acids and for oil, lipid and fatty acid compositions and to their use as drugs, cosmetics, foodstuffs, feedstuffs, preferably fish food, or food supplements.

15 Claims, 4 Drawing Sheets

(56) References Cited

OTHER PUBLICATIONS

Figure 3:
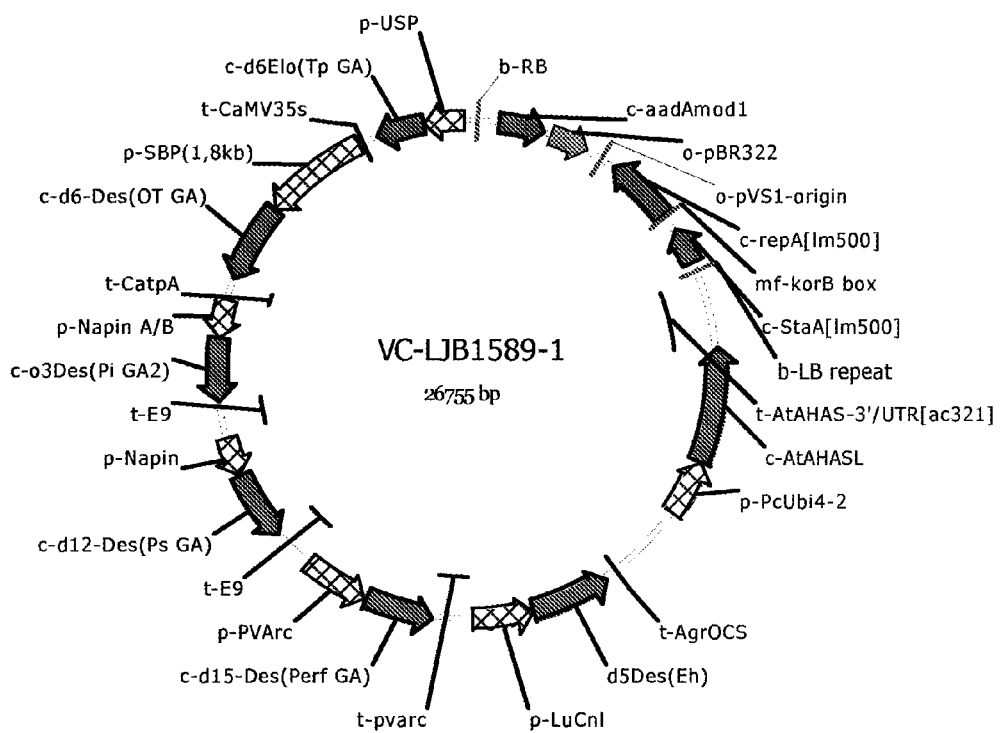

Tocher et al., "Recent Advances in the Biochemistry and Molecular Biology of Fatty Acyl Desaturases," *Prog. Lipid Res.*, vol. 37, No. 2/3. pp. 73-117 (1998).
Takeyama et al., "Expression of the eicosapentaenoic acid synthesis gene cluster from *Shewanella* sp. in a transgenic marine cyanobacterium, *Synechococcus* sp.," *Microbiology*, vol. 142, pp. 2725-2731 (1997).
Poulos, "Very Long Chain Fatty Acids in Higher Animals—A Review," *Lipids*, vol. 30, No. 1, 14 pages (1995).
Wada et al., "Enchancement of chilling tolerance of a cyanobacterium by genetic manipulation of fatty acid desaturation," *Nature*, vol. 347, pp. 200-203 (1990).
McKeon et al., "Stearoyl-Acyl Carrier Protein Desatrase from Safflower Seeds," *Methods in Enzymology*, vol. 71, pp. 275-281 (1981).
Wang et al., "Biosynthesis and regulation of linolenic acid in higher plants," *Plant Physiol. Biochem*, vol. 26, No. 6, pp. 777-792 (1988).
Totani et al., "The Filamentous Fungus *Mortierella* alpine, High in Arachidonic Acid," *Lipids*, vol. 22, No. 12, pp. 1060-1062 (1987).
Akimoto et al., "Carbon Dioxide Fixation and Polyunsaturated Fatty Acid Production by the Red Alga *Porphyridium cruentum*," vol. 73, pp. 269-278 (1998).
Yu et al., Production of Eicosapentaenoic Acid by a Recombinant Marine Cyanobacterium, *Synechococcus* sp., *Lipids*, vol. 35, pp. 1061-1064 (2000).
Zank et al., "Cloning and functional characterization of an enzyme involved in the elongation of Δ6- polyunsaturated fatty acids from the moss *Physcomitrella patens*," *The Plant Journ.*, vol. 31, No. 3, pp. 255-268 (2002).
Sakuradani et al., "Δ6-Fatty acid desaturase from an arachiodinic acid-producing *Mortierella* fungas," *Gene*, vol. 238, pp. 445-453 (1999).
Sprecher, "Metabolism of highly unsaturated n-3 and n-6 fatty acids," *Biochem et Biophysica Acta*, vol. 1486, pp. 219-231 (2000).
Tocher et al., "Recent Advances in the Biochemistry and Molecular Biology of Fatty Acyl Desaturases," *Prog. Lipid Res.*, vol. 37, No. 2/3, pp. 73-117 (1998).
Domergue et al., "Cloning and functional characterization of *Phaeodactylum tricornutum* front-end desatures involved in eicosapentaenoic acid biosynthesis," *Eur. J. Biochem.*, vol. 269, pp. 4105-4113 (2002).
Hamazaki, "Beneficial Effects of Eicosapentaenoic Acid on Endothelial Vasodilator Functions in Animals and Humans," *Fatty Acids and Lipids*, vol. 88, pp. 100-108 (2001).
Calder, "Dietary modification of inflammation with lipids," *Proceedings of the Nutrition Society*, vol. 61, pp. 345-358 (2002).
Cleland et al., "Fish Oil and Rheumatoid Arthritis: Antiinflammatory and Collateral Health Benefits," *The Journ. Of Rheumatology*, pp. 2305-2307 (2000).
Bell et al., "Lipid Composition During Growth of Motile and Coccolith Forms of *Emiliania huxleyi*," *Phytochemistry*, vol. 41, No. 2, pp. 465-471 (1996).
Pond et al., "The LIPID Compositions of the Coccolithophore *Emiliania huxleyi* and its possible ecophysiological Significance," vol. 76, pp. 579-594 (1996).
Guschina et al., "Lipids and lipid metabolism in eukaryotic algae," *Progress in Lipid Research*, vol. 45, pp. 160-186 (2006).
Singh et al., "Metabolic engineering of new fatty acids in plants," *Current Opinion in Plant Biology*, vol. 8, pp. 197-203 (2005).
Napier et al., "Progress towards the production of very long-chain polyunsaturated fatty acid in transgenic plants: plant metabolic engineering comes of age," *Physiol. Plant.*, vol. 126, pp. 398-406 (2006).
Zhou et al., "Isolation and characterization of genes from the marine microalga *Pavlova salina* encoding three front-end desaturases involved in docosahexaenoic acid biosynthesis," *Psytochemistry*, vol. 68, pp. 785-796 (2007).

* cited by examiner

Fig. 1

```
                   *        20         *        40         *
SEQ ID 1     : --MSLAAKDAASAHSSVLDPKYHCATN--K-SRTDAADLTVSSIDTSREM :  45
d6-Des(Ot)   : MGMRTENNDGIPTVEIAFDGERERAEANVKLSAEKMEPAALAKTFARRYV :  50

60        *        80         *        100
SEQ ID 1     : IIRGRVYDVSDFIKRHPGGSIIKISLG---SDATDAYNNFHIRSKKAEEM :  92
d6-Des(Ot)   : VLEGVFYDVTDEK--HPGGTVIFYALSNTGADATEAFKEFHIRSRKARKA :  98

*        120        *        140        *
SEQ ID 1     : LRALPSREVADGEARDALS-NDFEAIRAQLEAEGYFEDNLWHVAYRVAEV : 141
d6-Des(Ot)   : LRALPSREAKTAKVIDAEMIQDFAKWRKELERDGFFKPSPAHVAYRFAEL : 148

*        160        *        180        *        200
SEQ ID 1     : VAMWAGLRLIWASYWFLGAIVAGIAQG-RCGWLQHEGGHYSLTGNIKID : 190
d6-Des(Ot)   : AAMYALETYLMYARIVVSSVLVYACFFEARCGWVQHEGGHSSLTGNIWWD : 198

*        220        *        240        *
SEQ ID 1     : RHVQMILYGLGCGMSGCYWRNQHNKHHAIPQKLCADPDLQTMPLVAEHGL : 240
d6-Des(Ot)   : KRLDAFTAGFFLACSGDMWNSMHNKHHAIPQKVRHDMDLDTTDAVAEENT : 248

*        260        *        280        *        300
SEQ ID 1     : IGAKAF--GAGSMLAWQABLFGGVITLVSFGWQFVQHFHALRVGNQ : 288
d6-Des(Ot)   : AVEGNPFRGFSKYMRLQAWTEIP-VTSLVILLGMFFLHISKAERGGKY : 297

*        320        *        340        *
SEQ ID 1     : LEIGIMALRYALWYAAFGHIGLGCAERLNAFYVA---VGGTYIETNBAVS : 335
d6-Des(Ot)   : KELVMMLAAHVIRIWTIKAVTGETAMQSIGLELATSWSGCYLRAHESTS : 347

*        360        *        380        *        400
SEQ ID 1     : HTPADVYPHDKHLSWTLMSANHTTNQS-NTPLVNWMAELNFQIRHHLFP : 384
d6-Des(Ot)   : HTPLDVVEADEHLSWVRTAVDHTIDDPSQGWMNILMGFLNCQVIHHLFP : 397

*        420        *        440        *
SEQ ID 1     : SMPQYNHEKICGRVKQLFEEHGVEKVVRIYAKSMRDIYVNLLAVGNASHS : 434
d6-Des(Ot)   : SMPQFRQESVSREFVAFAKEWNLNYKVMTYAGAWRATLGNLDNVG-KHYY : 446

*        460        *
SEQ ID 1     : LHQRNEGLTTPFSAAVRVTGH : 455
d6-Des(Ot)   : VHSQHSEKTA----------- : 456
```

Fig 2.
A
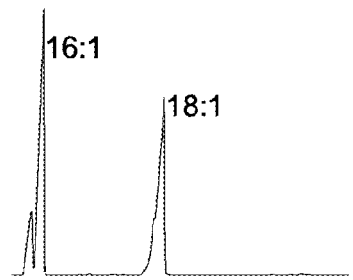
16:1     18:1
B
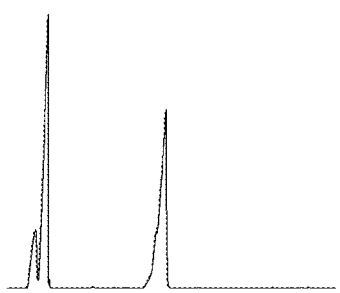
16:1     18:1
C
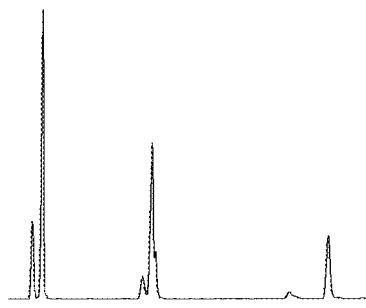
16:1     18:1     20:3
D
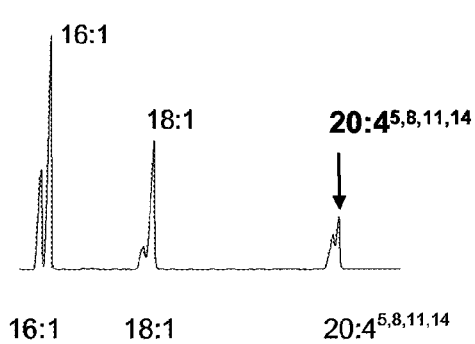
16:1     18:1     20:4$^{5,8,11,14}$

DESATURASE AND METHOD FOR THE PRODUCTION OF POLYUNSATURATED FATTY ACIDS IN TRANSGENIC ORGANISMS

This application is a 371 of PCT/EP09/55210 filed 29 Apr. 2009.

The present invention relates to a polynucleotide from *Emiliana huxleyi* which codes for a desaturase and which can be employed for the recombinant production of polyunsaturated fatty acids. The invention furthermore relates to vectors, host cells and transgenic nonhuman organisms which comprise the polynucleotides according to the invention, and to the polypeptides encoded by the polynucleotides. The invention furthermore relates to antibodies against the polypeptides according to the invention. Finally, the invention also relates to production methods for the polyunsaturated fatty acids and for oil, lipid and fatty acid compositions and to their use as drugs, cosmetics, foodstuffs, feedstuffs, preferably fish food, or food supplements.

Fatty acids and triacylglycerides have a multiplicity of applications in the food industry, in animal nutrition, in cosmetics and in the pharmacological sector. Depending on whether they are free saturated or unsaturated fatty acids or else triacylglycerides with an elevated content of saturated or unsaturated fatty acids, they are suitable for very different applications. Polyunsaturated fatty acids such as linoleic acid and linolenic acid are essential for mammals, since they cannot be produced by the latter themselves. Polyunsaturated ω3-fatty acids and ω6-fatty acids are therefore an important constituent in animal and human nutrition.

Polyunsaturated long-chain ω3-fatty acids such as eicosapentaenoic acid (=EPA, $C20:5^{\Delta5,8,11,14,17}$) or docosahexaenoic acid (=DHA, $C22:6^{\Delta4,7,10,13,16,19}$) are important components in human nutrition owing to their various roles in health aspects, including the development of the child brain, the functionality of the eyes, the synthesis of hormones and other signal substances, and the prevention of cardiovascular disorders, cancer and diabetes (Poulos, A Lipids 30:1-14, 1995; Horrocks, L A and Yeo Y K Pharmacol Res 40:211-225, 1999). This is why there is a demand for the production of polyunsaturated long-chain fatty acids.

Owing to the present-day composition of human food, an addition of polyunsaturated ω3-fatty acids, which are preferentially found in fish oils, to the food is particularly important. Thus, for example, polyunsaturated fatty acids such as docosahexaenoic acid (=DHA, $C22:6^{\Delta4,7,10,13,16,19}$) or eicosapentaenoic acid (=EPA, $C20:5^{\Delta5,8,11,14,17}$) are added to infant formula to improve the nutritional value. The unsaturated fatty acid DHA is said to have a positive effect on the development and maintenance of brain functions.

Hereinbelow, polyunsaturated fatty acids are referred to as PUFA, PUFAs, LCPUFA or LCPUFAs (polyunsaturated fatty acids, PUFA, long-chain polyunsaturated fatty acids, LCPUFA).

The various fatty acids and triglycerides are mainly obtained from microorganisms such as *Mortierella* and *Schizochytrium* or from oil-producing plants such as soybean, oilseed rape, algae such as *Crypthecodinium* or *Phaeodactylum* and others, where they are obtained, as a rule, in the form of their triacylglycerides (=triglycerides=triglycerols). However, they can also be obtained from animals, such as, for example, fish. The free fatty acids are advantageously prepared by hydrolysis. Very long-chain polyunsaturated fatty acids such as DHA, EPA, arachidonic acid (=ARA, $C20:4^{\Delta5,8,11,14}$), dihomo-γ-linolenic acid ($C20:3^{\Delta8,11,14}$) or docosapentaenoic acid (DPA, $C22:5^{\Delta7,10,13,16,19}$) are not synthesized in oil crops such as oilseed rape, soybean, sunflower or safflower. Conventional natural sources of these fatty acids are fish such as herring, salmon, sardine, redfish, eel, carp, trout, halibut, mackerel, zander or tuna, or algae.

Depending on the intended use, oils with saturated or unsaturated fatty acids are preferred. In human nutrition, for example, lipids with unsaturated fatty acids, specifically polyunsaturated fatty acids, are preferred. The polyunsaturated ω3-fatty acids are said to have a positive effect on the cholesterol level in the blood and thus on the possibility of preventing heart disease. The risk of heart disease, a stroke or hypertension can be reduced markedly by adding these ω3-fatty acids to food. Also, ω3-fatty acids have a positive effect on inflammatory, specifically on chronically inflammatory, methods in association with immunological diseases such as rheumatoid arthritis. They are therefore added to foodstuffs, specifically to dietetic foodstuffs, or are employed in medicaments. ω6-Fatty acids such as arachidonic acid tend to have a negative effect on these disorders in connection with these rheumatic diseases on account of our usual dietary intake.

ω3- and ω6-fatty acids are precursors of tissue hormones, known as eicosanoids, such as the prostaglandins, which are derived from dihomo-γ-linolenic acid, arachidonic acid and eicosapentaenoic acid, and of the thromboxanes and leukotrienes, which are derived from arachidonic acid and eicosapentaenoic acid. Eicosanoids (known as the $PG_2$ series) which are formed from ω6-fatty acids generally promote inflammatory reactions, while eicosanoids (known as the $PG_3$ series) from ω3-fatty acids have little or no proinflammatory effect.

Owing to the positive characteristics of the polyunsaturated fatty acids, there has been no lack of attempts in the past to make available genes which are involved in the synthesis of fatty acids or triglycerides for the production of oils in various organisms with a modified content of unsaturated fatty acids. Thus, WO 91/13972 and its US equivalent describe a Δ9-desaturase. WO 93/11245 claims a Δ15-desaturase and WO 94/11516 a Δ12-desaturase. Further desaturases are described, for example, in EP-A-0 550 162, WO 94/18337, WO 97/30582, WO 97/21340, WO 95/18222, EP-A-0 794 250, Stukey et al., J. Biol. Chem., 265, 1990: 20144-20149, Wada et al., Nature 347, 1990: 200-203 or Huang et al., Lipids 34, 1999: 649-659. However, the biochemical characterization of the various desaturases has been insufficient to date since the enzymes, being membrane-bound proteins, present great difficulty in their isolation and characterization (McKeon et al., Methods in Enzymol. 71, 1981: 12141-12147, Wang et al., Plant Physiol. Biochem., 26, 1988: 777-792). As a rule, membrane-bound desaturases are characterized by being introduced into a suitable organism which is subsequently analyzed for enzyme activity by analyzing the starting materials and the products. Δ6-Desaturases are described in WO 93/06712, U.S. Pat. No. 5,614,393, WO 96/21022, WO 00/21557 and WO 99/27111. Their application for production in transgenic organisms is described, for example, in WO 98/46763, WO 98/46764 and WO 98/46765. In this context, the expression of various desaturases and the formation of polyunsaturated fatty acids is also described and claimed; see, for example, WO 99/64616 or WO 98/46776. As regards the expression efficacy of desaturases and its effect on the formation of polyunsaturated fatty acids, it must be noted that the expression of a single desaturase as described to date has only resulted in low contents of unsaturated fatty acids/lipids such as, for example, γ-linolenic acid and stearidonic acid. Moreover, a mixture of ω3- and ω6-fatty acids was obtained, as a rule.

Especially suitable microorganisms for the production of PUFAs are microalgae such as *Phaeodactylum tricornutum, Porphiridium* species, *Thraustochytrium* species, *Schizochytrium* species or *Crypthecodinium* species, ciliates such as *Stylonychia* or *Colpidium*, fungae such as *Mortierella, Entomophthora* or *Mucor* and/or mosses such as *Physcomitrella, Ceratodon* and *Marchantia* (R. Vazhappilly & F. Chen (1998) Botanica Marina 41: 553-558; K. Totani & K. Oba (1987) Lipids 22: 1060-1062; M. Akimoto et al. (1998) Appl. Biochemistry and Biotechnology 73: 269-278). Strain selection has resulted in the development of a number of mutant strains of the microorganisms in question which produce a series of desirable compounds including PUFAs. However, the mutation and selection of strains with an improved production of a particular molecule such as the polyunsaturated fatty acids is a time-consuming and difficult method. This is why recombinant methods as described above are preferred whenever possible. However, only limited amounts of the desired polyunsaturated fatty acids such as DPA, EPA or ARA can be produced with the aid of the abovementioned microorganisms. Moreover, depending on the microorganism used, these are generally generated as fatty acid mixtures of, for example, EPA, DPA and ARA.

A variety of synthetic pathways is being discussed for the synthesis of arachidonic acid, eicosapentaenoic acid (EPA) and docosahexaenoic acid (DHA). Thus, EPA or DHA are produced in marine bacteria such as *Vibrio* sp. or *Shewanella* sp. via the polyketide pathway (Yu, R. et al. Lipids 35:1061-1064, 2000; Takeyama, H. et al. Microbiology 143:2725-2731, 1997).

An alternative strategy is the alternating activity of desaturases and elongases (Zank, T. K. et al. Plant Journal 31:255-268, 2002; Sakuradani, E. et al. Gene 238:445-453, 1999). A modification of this pathway via Δ6-desaturase, Δ6-elongase, Δ5-desaturase, Δ5-elongase and Δ4-desaturase is the Sprecher pathway (Sprecher 2000, Biochim. Biophys. Acta 1486: 219-231) in mammals. Instead of the Δ4-desaturation, a further elongation step is effected here to give $C_{24}$, followed by a further Δ6-desaturation and finally β-oxidation to give the $C_{22}$ chain length. What is known as the Sprecher pathway is, however, not suitable for the production in plants and microorganisms since the regulatory mechanisms are not yet known.

Depending on their desaturation pattern, the polyunsaturated fatty acids can be divided into two large classes, viz. ω6- or ω3-fatty acids, which differ with regard to their metabolic and functional activities. The starting material for the ω6-metabolic pathway is the fatty acid linoleic acid $(18:2^{\Delta 9,12})$ while the ω3-pathway proceeds via linolenic acid $(18:3^{\Delta 9,12,15})$. Linolenic acid is formed by the activity of a Δ15-desaturase (Tocher et al. 1998, Prog. Lipid Res. 37, 73-117; Domergue et al. 2002, Eur. J. Biochem. 269, 4105-4113).

Mammals, and thus also humans, have no corresponding desaturase activity (Δ12- and Δ15-desaturase) and must take up these fatty acids (essential fatty acids) via food. Starting with these precursors, the physiologically important polyunsaturated fatty acids arachidonic acid (=ARA, $20:4^{\Delta 5,8,11,14}$), an ω6-fatty acid and the two ω3-fatty acids eicosapentaenoic acid (=EPA, $20:5^{\Delta 5,8,11,14,17}$) and docosahexaenoic acid (DHA, $22:6^{\Delta 4,7,10,13,17,19}$) are synthesized via the sequence of desaturase and elongase reactions. The application of ω3-fatty acids shows the therapeutic activity described above in the treatment of cardiovascular diseases (Shimikawa 2001, World Rev. Nutr. Diet. 88, 100-108), inflammations (Calder 2002, Proc. Nutr. Soc. 61, 345-358) and arthritis (Cleland and James 2000, J. Rheumatol. 27, 2305-2307).

Higher plants comprise polyunsaturated fatty acids such as linoleic acid (C18:2) and linolenic acid (C18:3). ARA, EPA and DHA are not found at all in the seed oil of higher plants, or only in miniscule amounts (E. Ucciani: Nouveau Dictionnaire des Huiles Végétales [New Dictionary of Vegetable Oils]. Technique & Documentation—Lavoisier, 1995. ISBN: 2-7430-0009-0). However, the production of LCPUFAs in higher plants (preferably in oil crops such as oilseed rape, linseed, sunflower and soybeans) would be advantageous since large amounts of high-quality LCPUFAs for the food industry, animal nutrition and pharmaceutical purposes might be obtained economically. A potential route is via recombinant methods, where genes which code for enzymes of the biosynthesis of LCPUFAs are introduced and expressed. These genes code for, for example, Δ6-desaturases, Δ6-elongases, Δ5-desaturases or Δ4-desaturases. These genes can advantageously be isolated from microorganisms and lower plants which produce LCPUFAs and incorporate them in the membranes or triacylglycerides. Thus, it has already been possible to isolate Δ6-desaturase genes from the moss *Physcomitrella patens* and Δ6-elongase genes from *P. patens* and from the nematode *C. elegans*. (Zank, T. K. et al. Plant Journal 31:255-268, 2002, Beaudoin et al. Biochem Soc Trans 28 : 661-663, 2000).

The first transgenic plants which comprise and express genes coding for LCPUFA biosynthesis enzymes and which produce LCPUFAs were described for the first time, for example, in DE-A-102 19 203 (method for the production of polyunsaturated fatty acids in plants). However, these plants produce LCPUFAs in amounts which require further optimization for methoding the oils which are present in the plants.

To make possible the fortification of food and of feed with these polyunsaturated fatty acids, there is therefore a great need for a simple, inexpensive method for the production of these polyunsaturated fatty acids, specifically in eukaryotic systems.

The object on which the present invention is based is the provision of such means and measures. This object is achieved by the embodiments which are described in the patent claims and hereinbelow.

The present invention thus relates to a polynucleotide comprising a nucleic acid sequence selected from the group consisting of:
  (a) nucleic acid sequence as shown in any of SEQ ID NO: 1;
  (b) nucleic acid sequence which codes for a polypeptide having an amino acid sequence as shown in any of SEQ ID NO: 2;
  (c) nucleic acid sequence which has at least 70% identity to one of the nucleic acid sequence of (a) or (b), and which codes for a polypeptide with desaturaase activity; and
  (d) nucleic acid sequence for a fragment of a nucleic acid of (a), (b) or (c), where the fragment codes for a polypeptide with desaturase activity.

According to the invention, the term "polynucleotide" refers to polynucleotides which comprise nucleic acid sequences which code for polypeptides with desaturase activity. The desaturase activities are preferably required for the biosynthesis of lipids or fatty acids. Especially preferably, they take the form of the following desaturase activity: Δ5-desaturase activity. The desaturase is preferably involved in the synthesis of polyunsaturated fatty acids (PUFAs) and especially preferably in the synthesis of long-chain PUFAs (LCPUFAs). Suitable detection systems for this desaturase activity are described in the examples or in WO 2005/083053. The specific polynucleotides according to the invention, i.e. the polynucleotide with a nucleic acid sequence as shown in SEQ ID NO: 1 or polynucleotides which code for a polypeptide with an amino acid sequence as shown in SEQ ID NO: 2 have been obtained from *Emiliana huxleyi*. The term also comprises variants of the abovementioned specific polynucleotides. These may take the form of homologous, orthologous or paralogous sequences. Such variants comprise nucleic acid sequences which feature at least one base substitution, one base addition or one base deletion, it being intended that the variants still code for a polypeptide with the abovementioned biological activity of the respective starting sequence. Variants comprise polynucleotides which are capable of hybridization with the abovementioned polynucleotides, preferably under stringent conditions. Especially preferred stringent conditions are known to the skilled worker and can be found in Current Protocols in Molecular Biology, John Wiley & Sons, N.Y. (1989), 6.3.1-6.3.6. A preferred example of stringent hybridization conditions are hybridizations in 6× sodium chloride/sodium citrate (=SSC) at approximately 45° C., followed by one or more wash steps in 0.2×SSC, 0.1% SDS at 50 to 65° C. The skilled worker knows that these hybridization conditions differ as a function of the type of nucleic acid and, for example when organic solvents are present, with regard to the temperature and the buffer concentration. Under "standard hybridization conditions", the temperature differs as a function of the type of nucleic acid between 42° C. and 58° C. in aqueous buffer with a concentration of from 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably for example 0.1×SSC and 30° C. to 55° C., preferably between 45° C. and 55° C. The abovementioned hybridization temperatures are determined for example for a nucleic acid of approximately 100 by (=base pairs) in length and a G+C content of 50% in the absence of formamide. The skilled worker knows how to determine the hybridization conditions required with the aid of textbooks, such as the one mentioned hereinabove, or from the following textbooks: Sambrook et al., Molecular Cloning, Cold Spring Harbor Laboratory, 1989; Hames and Higgins (eds.) 1985, Nucleic Acids Hybridization: A Practical Approach, IRL Press at Oxford University Press, Oxford; Brown (ed.) 1991, Essential Molecular Biology: A Practical Approach, IRL Press at Oxford University Press, Oxford. As an alternative, variants of the specific polynucleotides according to the invention may also be provided by polymerase chain reaction (PCR)-based methods. To this end, it is possible first to derive primers from conserved sequences (for example sequences which code for functional domains in the polypeptide). Conserved sequences can be determined by sequence comparisons with polynucleotides which code for polypeptides with a similar activity. The template used may be DNA or cDNA from bacteria, fungi, plants or animals. DNA fragments obtained by PCR can be used for screening suitable genomic libraries or cDNA libraries in order to—if required—isolate the complete open reading frame of the polynucleotide and to determine it by sequencing. Preferred variants comprise polynucleotides which comprise a nucleic acid sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the above-mentioned specific nucleic acid sequences and codes for a polypeptide with the respective biological activity. Equally preferably comprised are polynucleotides which comprise nucleic acid sequences which code for a polypeptide with an amino acid sequence with at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% (or a different percentage than mentioned herein) identity with one of the abovementioned specific amino acid sequences and where the polypeptide has the respective biological activity of the starting sequence.

The percentage of identical nucleotides or amino acids preferably relates to a sequence segment of at least 50% of the sequences to be compared, and especially preferably over the entire length of the sequences to be compared. A multiplicity of programs which implement algorithms for such comparisons are described in the prior art and commercially available. In particular, reference may be made to the algorithms of Needleman and Wunsch or Smith and Waterman, which give particularly reliable results. These algorithms can preferably be implemented by the following programs: PileUp (J. Mol. Evolution., 25, 351-360, 1987, Higgins 1989, CABIOS, 5: 151-153), Gap and BestFit (Needleman 1970, J. Mol. Biol. 48; 443-453 and Smith 1981, Adv. Appl. Math. 2; 482-489), as part of the GCG software (Genetics Computer Group, 575 Science Drive, Madison, Wis., USA 53711, 1991). For the purposes of the present invention, it is especially preferred to determine the percentage (%) of the sequence identity with the GAP program over the entire sequence, with the following set parameters: Gap Weight: 50, Length Weight: 3, Average Match: 10.000 and Average Mismatch: 0.000.

A polynucleotide which only comprises a fragment of the abovementioned nucleic acid sequences is also a polynucleotide according to the invention. Here, it is intended that the fragment codes for a polypeptide which features the biological activity of the starting sequence, or of the polypeptide which the latter codes for. Polypeptides which are encoded by such polynucleotides therefore comprise, or consist of, domains of the abovementioned specific polypeptides (starting polypeptides) which confer the biological activity. A fragment for the purposes of the invention preferably comprises at least 50, at least 100, at least 250 or at least 500 consecutive nucleotides of the abovementioned specific sequences or codes for an amino acid sequence comprising at least 20, at least 30, at least 50, at least 80, at least 100 or at least 150 consecutive amino acids of one of the abovementioned specific amino acid sequences, and confers biological activity, preferably desaturase activity, as described above.

The term "desaturase activity" as used in the present context refers to an enzymatic activity by which a dehydrogenation of fatty acids or fatty acid derivatives as substrates catalyzes. The desaturase activity according to the invention preferably takes the form of deta-5 desaturase (also referred to as Δ5-desaturase activity). Δ5-Desaturases are enzymes with the enzymatic function for the dehydrogenation of C20 fatty acids which are dehydrogenated at the C atom 8-9. Here, the C atoms C5 and C6 are dehydrogenated by in each case one hydrogen atom, giving rise to a double bond between the two C atoms. It is especially preferred that enzymes with desaturase activity—and in particular Δ5-desaturase activity—within the meaning of the present invention also convert acyl-coenzyme A as substrate.

The polynucleotide variants according to the invention preferably feature at least 10%, at least 20%, at least 30%, at least 40%, at least 50%, at least 60%, at least 70%, at least 80% or at least 90% of the respective biological activity of the polypeptide which is encoded by the starting sequence. That is to say the polypeptides which are encoded by the polynucleotides according to the invention can participate in the metabolism of compounds required for the synthesis of fatty acids, fatty acid esters such as diacylglycerides and/or triacylglycerides in an organism, preferably in a plant or plant cell, or can participate in the transport of molecules across membranes, which means $C_{18}$-, $C_{20}$- or $C_{22}$-carbon chains in the fatty acid molecule with double bonds at least two, advantageously three, four, five or six positions.

The polynucleotides according to the invention either comprise the abovementioned specific nucleic acid sequences or consist of them. That is to say, that the polynucleotides according to the invention may, in principle, also comprise further nucleotides. These may preferably be 3'- or 5'-untranslated regions of the genomic nucleic acid sequence. They preferably consist of at least 100, 200 or 500 nucleotides at the 5' terminus and of at least 20, 50 or 100 nucleotides at the 3' terminus of the coding region. Further polynucleotides which comprise additional nucleic acid sequences are those which code for fusion proteins. Such fusion proteins can code for further polypeptide or polypeptide portions, in addition to the abovementioned polypeptides. The additional polypeptide or polypeptide portion may take the form of further enzymes of lipid or fatty acid biosynthesis. Others which are feasible are polypeptides which may act as expression markers (green, yellow, red, blue fluorescent proteins, alkaline phosphatase and others) or so-called "tags" as labels or as an aid for purification (for example FLAG tags, 6-histidine tags, MYC tags and others).

Polynucleotide variants can be isolated from different natural or artificial sources. For example, they can be generated artificially by in-vitro or in-vivo mutagenesis. Homologs or orthologs of the specific sequences can be obtained from a wide range of animals, plants and microorganisms. They are preferably obtained from algae. Algae such as *Isochrysis, Euglena* or *Crypthecodinium*, algae/diatoms such as *Thalassiosira, Phaeodactylum* or *Thraustochytrium, Pythium*, mosses such as *Physcomitrella* or *Ceratodon* are preferred, very especially preferred are the algae of the genus *Euglena* or the diatoms of the class Oomycota such as the genera *Pythium* or *Phytophtora* or fungi from the division Zygomywta from the genera *Rhizopus*. The polynucleotides can also be preferably be obtained from higher plants such as Primulaceae such as *Aleuritia, Calendula stellata, Osteospermum spinescens* or *Osteospermum hyoseroides*, microorganisms such as fungi, such as *Aspergillus, Thraustochytrium, Phytophthora, Entomophthora, Mucor* or *Mortierella*, bacteria such as *Shewanella*, yeasts or animals such as nematodes, for example *Caenorhabditis*, insects or fish. The polynucleotide variants are also preferably derived from an animal from the order vertebrates. Especially preferably, the polynucleotides are derived from the class Vertebrata; Euteleostomi, Actinopterygii; Neopterygii; Teleostei; Euteleostei, Protacanthopterygii, Salmoniformes; Salmonidae or Oncorhynchus and, very especially preferably, from the order Salmoniformes such as the family Salmonidae, such as the genus *Salmo*, for example from the genera and species *Oncorhynchus mykiss, Trutta trutta* or *Salmo trutta fario*. Here, the polynucleotides according to the invention can be isolated by means of standard techniques of molecular biology and of the sequence information provided herein. Also, it is possible, with the aid of comparative algorithms, to identify for example a homologous sequence or homologous, conserved sequence regions at the DNA or amino acid level. These can be employed as hybridization probe and standard hybridization techniques (such as, for example, those described in Sambrook et al., Molecular Cloning: A Laboratory Manual. $2^{nd}$ Ed., Cold Spring Harbor Laboratory, Cold Spring Harbor Laboratory Press, Cold Spring Harbor, N.Y., 1989) for isolating further nucleic acid sequences which are useful in the method. Moreover, it is possible to isolate polynucleotides or fragments thereof by means of polymerase chain reaction (PCR), where oligonucleotide primers which are based on this sequence or parts thereof are employed (for example, a nucleic acid molecule comprising the complete sequence or part thereof can be isolated by polymerase chain reaction using oligonucleotide primers which have been generated on the basis of this same sequence). For example, it is possible to isolate mRNA from cells (for example by the guanidinium thiocyanate extractive method by Chirgwin et al. (1979) Biochemistry 18:5294-5299, and cDNA can be generated by means of reverse transcriptase (for example Moloney MLV reverse transcriptase, obtainable from Gibco/BRL, Bethesda, Md., or AMV reverse transcriptase, obtainable from Seikagaku America, Inc., St. Petersburg, Fla.). Synthetic oligonucleotide primers for the amplification by means of polymerase chain reaction can be generated on the basis of the polynucleotide and amino acid sequences shown in the SEQ ID numbers. A nucleic acid according to the invention can be amplified using cDNA or, alternatively, genomic DNA as the template and suitable oligonucleotide primers, following standard PCR amplification techniques. The nucleic acid amplified thus can be cloned into a suitable vector and characterized by means of DNA sequence analysis. Oligonucleotides which correspond to a desaturase nucleotide sequence can be generated by standard synthetic methods, for example using an automatic DNA synthesizer.

The polynucleotides according to the invention can either be provided in the form of isolated polynucleotides (i.e. isolated from their natural origin, for example the genomic locus) or else in genetically modified form (i.e. the polynucleotides may also be present at their natural genetic locus, but, in such a case, must be genetically modified). An isolated polynucleotide preferably comprises less than 5 kb, 4 kb, 3 kb, 2 kb, 1 kb, 0.5 kb or 0.1 kb of nucleic acid sequence which occurs naturally in its environment. The polynucleotide according to the invention may be present as a single-stranded or double-stranded nucleic acid molecule and may take the form of genomic DNA, cDNA or RNA. Preferably, the polynucleotide according to the invention consists of RNA or DNA. The polynucleotides according to the invention comprise all orientations of the sequences shown in the SEQ ID numbers, i.e. also complementary strands and reverse, or reverse-complementary, orientations. The term furthermore also comprises chemically modified nucleic acids, such as the naturally occurring methylated DNA molecules, or artificial nucleic acids, for example biotinylated nucleic acids.

Owing to the polynucleotides according to the invention, the substrates 20:4Δ5,8,11,14 and 20:5Δ5,8,11,14,17 can be increased in the recombinant production of long-chain PUFAs. The Δ5-desaturase which is encoded by the polynucleotide according to the invention preferentially catalyzes the final synthesis step of 20:3Δ8,11,14 and 20:4Δ8,11,14,17 to give the commercially valuable long-chain polyunsaturated fatty acids. A variety of approaches for isolating Δ5-desaturases have been carried out in the past (for example Domergue et al. (2002), Eur J. Biochem. 269(16):4105-13, Kajikawa et al. (2004) Plant Mol. Biol. 54:335-52). It has also been possible to demonstrate that all of the previously known Δ5-desaturases utilize the same acyl carrier phosphatidylcholin (Domergue et al. (2003) J Biol. Chem. 278(37):35115-26). For Δ6-desaturases, it has been possible to demonstrate that the conversion of acyl-coenzyme A (acyl-carrier coenzyme A) is advantageous for the synthesis of long-chain polyunsaturated fatty acids (Domergue et al. (2005) Biochem J. 389(Pt 2):483-90). However, it has not been possible to date to identify any enzyme for the class of the 45-desaturases which is capable of converting acyl-coenzyme A as the substrate. Neither do sequence comparisons make it possible to predict the substrate specificity with regard to the acyl carrier. Surprisingly, it was possible to isolate, in the context of the present invention, a sequence from the alga *Emiliana huxleyi* (Eukaryota; Haptophyceae; Isochrysidales; Noelaerhabdaceae), which codes for an enzyme with 45-desaturase activity and which converts acyl-coenzyme A substrates. In particular, it has emerged, advantageously, that the polynucleotides according to the invention can be employed particularly efficiently for the recombinant production of polyunsaturated fatty acids in host cells and transgenic organisms. In particular, the polypeptides with 45-desaturase activity which are encoded by the polynucleotide according to the invention are capable of $C_{18}$—, $C_{20}$— and $C_{22}$-fatty acids with two, three, four or five double bonds and preferably polyunsaturated $C_{20}$-fatty acids with three or four double bonds such as $C20:3^{\Delta 8,11,14}$ or $C20:4^{\Delta 8,11,14,17}$. The polynucleotide and amino acid sequences according to the invention especially preferably lead to an increase in the fatty acids 20:4Δ5,8,11,14 (arachidonic acid) and 20:5Δ5,8,11,14,17 (eicosapentaenoic acid).

The invention also comprises oligonucleotides of at least 15 bp, preferably at least 20 bp, at least 25 bp, at least 30 bp, at least 35 bp or at least 50 bp, which are capable of specifically hybridizing under stringent conditions with one of the abovementioned polynucleotides. The oligonucleotides may consist of DNA or RNA or both. Such oligonucleotides can be employed as primers for the PCR, as expression-inhibitory antisense oligonucleotides, for RNA interference (RNAi) approaches or for chimeroplastic or genoplastic approaches. RNAi methods are described for example in Fire et al., Nature (1998) 391:806-811; Fire, Trends Genet. 15, 358-363 (1999); Sharp, RNA interference 2001. Genes Dev. 15, 485-490 (2001); Hammond et al. Nature Rev. Genet. 2, 1110-1119 (2001); Tuschl, Chem. Biochem. 2, 239-245 (2001); Hamilton et al., Science 286, 950-952 (1999); Hammond et al., Nature 404, 293-296 (2000); Zamore et al., Cell 101, 25-33 (2000); Bernstein et al., Nature 409, 363-366 (2001); Elbashir et al., Genes Dev. 15, 188-200 (2001); WO 01/29058; WO 99/32619; or Elbashir et al., 2001 Nature 411: 494-498 and serve for inhibiting gene expression by degrading the mRNA. Chimeroplastic or genoplastic approaches serve the in-vivo modification (for example the introduction of point mutations) into genes at their endogenous loci. Corresponding methods are disclosed in U.S. Pat. No. 5,565,350, U.S. Pat. No. 5,756,325, U.S. Pat. No. 5,871,984, U.S. Pat. No. 5,731, 181, U.S. Pat. No. 5,795,972, U.S. Pat. No. 6,573,046, U.S. Pat. No. 6,211,351, U.S. Pat. No. 6,586,184, U.S. Pat. No. 6,271,360 and U.S. Pat. No. 6,479,292.

In this context, it is especially preferred to employ the Δ6-desaturase encoded by the polynucleotide sequence with SEQ ID NO: 5 (d6Des(Pir)), the Δ6-elongase encoded by the polynucleotide sequence with SEQ ID NO: 7 (d6Elo(Pp)), the Δ5-desaturase encoded by the polynucleotide sequence with SEQ ID NO: 1 (d5Des(Eh)), the Δ12-desaturase encoded by the polynucleotide sequence with SEQ ID NO: 9 (d12Des (Ps)), the Δ15-desaturase encoded by the polynucleotide sequence with SEQ ID NO: 13 (d15Des(Perf)), the ω3-desaturase encoded by the polynucleotide sequence with SEQ ID NO: 11 (o3Des(Pi)), the Δ5-elongase encoded by the polynucleotide sequence with SEQ ID NO: (d5Elo(Ot)), and the Δ4-desaturase encoded by the polynucleotide sequence with SEQ ID NO: 17 (d4Des(Tc)) with the desaturase according to the invention in order to synthesize long-chain polyunsaturated fatty acids. The abovementioned polynucleotides are described in WO2006/100241. Alternatively, it was also possible to employ a Δ9-elongase and a Δ8-desaturase instead of the abovementioned Δ6-desaturase and the Δ6-elongase as described in WO2004/057001. Depending on the fatty acid which is to be prepared, it is possible to coexpress, in the host cells or transgenic organisms described hereinbelow, or to use in the methods according to the invention, a variety of combinations of the polynucleotides according to the invention with the abovementioned desaturases or elongases. Especially preferred combinations for the production of arachidonic acid in table 1, for eicosapentaenoic acid in table 2 and for docosahexaenoic acid in table 3 are detailed hereinbelow. For example, it is possible to use the Δ5-desaturase according to the invention, alone or in a suitable combination (for example a Δ12-desaturase and a Δ15-desaturase), together with d6Des(Pir), d6Elo(Pp), d5Des(Tc), ω3Des(Pi) for the production of EPA. Equally, the Δ5-desaturase according to the invention, alone or in a suitable combination, can be used together with d6Des(Pir), d6Elo(Pp), d5Des(Tc), ω3Des(Pi), d5Elo(Ot), d4Des(Tc) for the production of docosahexaenoic acid.

Preferably, it is the fatty acids in phospholipids or CoA fatty acid esters which are desaturated, advantageously in the CoA fatty acid esters. Thus, a simple, inexpensive production of these polyunsaturated fatty acids is possible, specifically in eukaryotic systems. The unsaturated fatty acids produced by means of the polynucleotides according to the invention can then be formulated as oil, lipid and fatty acid compositions and can be employed in a suitable manner.

The present invention furthermore relates to a vector which comprises the polynucleotide according to the invention.

The term "vector" refers to a nucleic acid molecule which is capable of transporting another nucleic acid molecule, such as the polynucleotides according to the invention, to which it is bound. One type of vector is a "plasmid", a circular double-stranded DNA loop into which additional DNA segments can be ligated. A further type of vector is a viral vector, it being possible for additional DNA segments to be ligated into the viral genome. Certain vectors are capable of autonomous replication in a host cell into which they have been introduced (for example bacterial vectors with bacterial replication origin). Other vectors are advantageously integrated into the genome of a host cell when they are introduced into the host cell, and thus replicate together with the host genome. Moreover, certain vectors can govern the expression of genes with which they are in operable linkage. These vectors are referred to in the present context as "expression vectors". Usually, expression vectors which are suitable for DNA recombination techniques take the form of plasmids. In the present description, "plasmid" and "vector" can be used exchangeably since the plasmid is the form of vector which is most frequently used. However, the invention is also intended to comprise other forms of expression vectors, such as viral vectors, which exert similar functions. Furthermore, the term "vector" is also intended to comprise other vectors with which the skilled worker is familiar, such as phages, viruses such as SV40, CMV, TMV, transposons, IS elements, phasmids, phagemids, cosmids, linear or circular DNA, artificial chromosomes. Finally, the term also comprises constructs for the targeted, i.e. homologous, recombination, or the heterologous insertion of polynucleotides.

Vectors can be introduced into prokaryotic and eukaryotic cells via conventional transformation or transfection techniques. The terms "transformation" and "transfection", conjugation and transduction, as used in the present context, are intended to comprise a multiplicity of methods known in the prior art for the introduction of foreign nucleic acid (for example DNA) into a host cell, including calcium phosphate or calcium chloride coprecipitation, DEAE-dextran-mediated transfection, lipofection, natural competence, chemically mediated transfer, electroporation or particle bombardment. Suitable methods for the transformation or transfection of host cells, including plant cells, can be found in Sambrook et al. (Molecular Cloning: A Laboratory Manual., 2nd ed., Cold Spring Harbor Laboratory, Cold Spring Harbor Laboratory Press, Cold Spring Harbor, N.Y., 1989) and other laboratory textbooks such as Methods in Molecular Biology, 1995, Vol. 44, *Agrobacterium* protocols, Ed.: Gartland and Davey, Humana Press, Totowa, N.J.

Suitable cloning vectors are generally known to the skilled worker. In particular, they include vectors which can replicate in microbial systems, that is mainly vectors which ensure efficient cloning in yeasts or fungi and which make possible the stable transformation of plants. Those which must be mentioned are in particular various binary and cointegrated vector systems which are suitable for the T-DNA-mediated transformation. Such vector systems are, as a rule, characterized in that they comprise at least the vir genes, which are required for the *agrobacterium*-mediated transformation, and the T-DNA-bordering sequences (T-DNA border). Preferably, these vector systems also comprise further cis-regulatory regions such as promoters and terminators and/or selection markers, by means of which suitably transformed organisms can be identified. While in the case of cointegrated vector systems vir genes and T-DNA sequences are arranged on the same vector, binary systems are based on at least two vectors, one of which bears vir genes, but no T-DNA, and the other bears T-DNA, but no vir gene. As a result, the last-mentioned vectors are relatively small, easy to manipulate and to replicate both in *E. coli* and in *Agrobacterium*. These binary vectors include vectors from the pBIB-HYG series, the pPZP series, the pBecks series and the pGreen series. Preferably used according to the invention are Bin19, pBI101, pBinAR, pGPTV and pCAMBIA. An overview of binary vectors and their use is found in Hellens et al, Trends in Plant Science (2000) 5, 446-451. The vectors with the inserted polynucleotides according to the invention can be propagated stably under selective conditions in microorganisms, in particular *Escherichia coli* and *Agrobacterium tumefaciens*, and make possible a transfer of heterologous DNA into plants or microorganisms. The polynucleotides according to the invention can be introduced into organisms such as microorganisms or plants by means of the cloning vectors and thus used for transforming plants. Vectors which are suitable for this purpose are published in: Plant Molecular Biology and Biotechnology (CRC Press, Boca Raton, Fla.), chapter 6/7, p. 71-119 (1993); F. F. White, Vectors for Gene Transfer in Higher Plants; in: Transgenic Plants, vol. 1, Engineering and Utilization, eds.: Kung and R. Wu, Academic Press, 1993, 15-38; B. Jenes et al., Techniques for Gene Transfer, in: Transgenic Plants, vol. 1, Engineering and Utilization, eds.: Kung and R. Wu, Academic Press (1993), 128-143; Potrykus, Annu. Rev. Plant Physiol. Plant Molec. Biol. 42 (1991), 205-225.

The vector is preferably an expression vector. The polynucleotide is present in the expression vector according to the invention in operative (i.e. functional) linkage with an expression control sequence. The expression control sequence together with the polynucleotide and optionally further sequence elements of the vector is also referred to as the expression cassette. The expression control sequence ensures that, after transformation or transfection into a host cell, the polynucleotide can be expressed. The expression control sequence to be used preferably comprises cis-regulatory elements such as promoter and/or enhancer nucleic acid sequences, which are recognized by the transcription machinery of the host cells. The term furthermore comprises other expression control elements, for example polyadenylation signals and RNA-stabilizing sequences. These regulatory sequences are described for example in Goeddel: Gene Expression Technology: Methods in Enzymology 185, Academic Press, San Diego, Calif. (1990) or see: Gruber and Crosby, in: Methods in Plant Molecular Biology and Biotechnology, CRC Press, Boca Raton, Fla., eds.: Glick and Thompson, chapter 7, 89-108, including the literature cited therein. Expression control sequences comprise those which govern the constitutive expression of a nucleotide sequence in many types of host cells, and those which govern the direct expression of the nucleotide sequence only in certain host cells under certain conditions. The skilled worker knows that the design of the expression vector may depend on factors such as the choice of the host cell to be transformed, the extent of the expression of the desired protein and the like. The polynucleotides according to the invention may be present in one or more copies in the expression cassette or in the expression vector according to the invention (for example in the form of several expression cassettes). Here, the regulatory sequences or factors can preferably have a positive effect on the gene expression of the introduced genes, as described above, and thereby increase it. Thus, it is possible to enhance the regulatory elements advantageously at the transcription level by using strong transcription signals such as promoters and/or "enhancers". Besides, it is also possible to enhance the translation, for example by improving the mRNA stability. Further expression control sequences within the meaning of the present invention are translation terminators at the 3' end of the polynucleotides to be translated. An example which can be used here is the OCS1 terminator. As in the case of the promoters, a different terminator sequence should be used for each polynucleotide to be expressed.

Preferred expression control sequences or regulatory sequences are present in promoters such as the cos, tac, trp, tet, trp-tet, lpp, lac, lpp-lac, lacIq, T7, T5, T3, gal, trc, ara, SP6, λ-PR or λ-PL promoters and are advantageously employed in Gram-negative bacteria. Further advantageous regulatory sequences are, for example, present in the Gram-positive promoters amy and SPO2, in the yeast or fungal promoters ADC1, MFα, AC, P-60, CYC1, GAPDH, TEF, rp28, ADH or in the plant promoters CaMV/35S [Franck et al., Cell 21 (1980) 285-294], PRP1 [Ward et al., Plant. Mol. Biol. 22 (1993)], SSU, OCS, lib4, usp, STLS1, B33, nos or in the ubiquitin or phaseolin promoter. Advantageous in this context are also inducible promoters, such as the promoters described in EP-A-0 388 186 (benzenesulfonamide-inducible), Plant J. 2, 1992:397-404 (Gatz et al., tetracycline-inducible), EP-A-0 335 528 (abscisic acid-inducible) or WO 93/21334 (ethanol- or cyclohexenol-inducible). Further suitable plant promoters are the cytosolic FBPase promoter or the ST-LSI promoter of potato (Stockhaus et al., EMBO J. 8, 1989, 2445), the *glycine max* phosphoribosyl-pyrophosphate amidotransferase promoter (Genbank Accession No. U87999) or the node-specific promoter described in EP-A-0 249 676. Especially advantageous promoters are promoters which make possible the expression in tissues which are involved in the biosynthesis of fatty acids. Very especially advantageous are seed-specific promoters, such as the USP promoter, but also other promoters such as the LeB4, DC3, phaseolin or napin promoter. Further especially advantageous promoters are seed-specific promoters which can be used for monocotyledonous or dicotyledonous plants and which are described in U.S. Pat. No. 5,608,152 (oilseed rape napin promoter), WO 98/45461 (*Arobidopsis* oleosin promoter), U.S. Pat. No. 5,504,200 (*Phaseolus vulgaris* phaseolin promoter), WO 91/13980 (*Brassica* Bce4 promoter), by Baeumlein et al., Plant J., 2, 2, 1992:233-239 (LeB4 promoter from a legume), these promoters being suitable for dicots. Examples of promoters which are suitable for monocots are the barley lpt-2 or lpt-1 promoter (WO 95/15389 and WO 95/23230), the barley hordein promoter and other suitable promoters described in WO 99/16890. In principle, it is possible to use all natural promoters together with their regulatory sequences, such as those mentioned above, as expression control sequences. It is also possible to use synthetic promoters, either in addition or alone, in particular when they mediate seed-specific expression, as described, for example, in WO 99/16890.

In order to achieve a particularly high PUFA content, especially in transgenic plants, the polynucleotides of the present invention should preferably be expressed in oil crops in a seed-specific manner. To this end, seed-specific promoters can be used, or those promoters which are active in the embryo and/or in the endosperm. In principle, seed-specific promoters can be isolated both from dicotyledonous and from monocotyledonous plants. Advantageous preferred promoters are listed hereinbelow: USP (=unknown seed protein) and vicilin (*Vicia faba*) [Baumlein et al., Mol. Gen. Genet., 1991, 225(3)], napin (oilseed rape) [U.S. Pat. No. 5,608,152], acyl carrier protein (oilseed rape) [U.S. Pat. No. 5,315,001 and WO 92/18634], oleosin (*Arabidopsis thaliana*) [WO 98/45461 and WO 93/20216], phaseolin (*Phaseolus vulgaris*) [U.S. Pat. No. 5,504,200], Bce4 [WO 91/13980], legumines B4 (LegB4 promoter) [Baumlein et al., Plant J., 2,2, 1992], Lpt2 and Ipt1 (barley) [WO 95/15389 and WO 95/23230], seed-specific promoters from rice, maize and wheat [WO 99/16890], Amy32b, Amy 6-6 and aleurain [U.S. Pat. No. 5,677,474], Bce4 (oilseed rape) [U.S. Pat. No. 5,530,149], glycinin (soybean) [EP 571 741], phosphoenol pyruvate carboxylase (soybean) [JP 06/62870], ADR12-2 (soybean) [WO 98/08962], isocitrate lyase (oilseed rape) [U.S. Pat. No. 5,689,040] or α-amylase (barley) [EP 781 849].

Plant gene expression can also be facilitated via a chemically inducible promoter (see a review in Gatz 1997, Annu. Rev. Plant Physiol. Plant Mol. Biol., 48:89-108). Chemically inducible promoters are particularly suitable when it is desired that gene expression should take place in a time-specific manner. Examples of such promoters are a salicylic acid-inducible promoter (WO 95/19443), a tetracycline-inducible promoter (Gatz et al. (1992) Plant J. 2, 397-404) and an ethanol-inducible promoter.

To ensure stable integration of the various biosynthesis genes into the transgenic plant over a plurality of generations, each of the polynucleotides according to the invention should be expressed under the control of a separate promoter, preferably a promoter which differs from the other promoters, since repeating sequence motifs can lead to instability of the T-DNA, or to recombination events. In this context, the expression cassette is advantageously constructed in such a way that a promoter is followed by a suitable cleavage site (advantageously in a polylinker) for insertion of the nucleic acid to be expressed and, if appropriate, a terminator is then positioned behind the polylinker. This sequence is repeated several times, preferably three, four or five times, so that up to five genes can be combined in one construct and introduced into the transgenic plant in order to be expressed. Advantageously, the sequence is repeated up to three times. To express the nucleic acid sequences, the latter are inserted behind the promoter via a suitable cleavage site, for example in the polylinker. Advantageously, each nucleic acid sequence has its own promoter and, if appropriate, its own terminator. Such advantageous constructs are disclosed, for example, in DE 101 02 337 or DE 101 02 338. However, it is also possible to insert a plurality of nucleic acid sequences behind a promoter and, if appropriate, in front of a terminator. Here, the insertion site, or the sequence, of the inserted nucleic acids in the expression cassette is not of critical importance, that is to say a nucleic acid sequence can be inserted at the first or last position in the cassette without its expression being substantially influenced thereby. Advantageously, different promoters such as, for example, the USP, LegB4 or DC3 promoters, and different terminators can be used in the expression cassette. However, it is also possible to use only one type of promoter in the cassette. This, however, may lead to undesired recombination events.

The recombinant expression vectors used can be designed for the expression in prokaryotic or eukaryotic cells. This is advantageous since intermediate steps of the vector construction are frequently carried out in microorganisms for the sake of simplicity. For example, the Δ12-desaturase, Δ15-desaturase, Δ12- and Δ15-desaturases, ω3-desaturase, Δ6-desaturase, Δ6-elongase, Δ9-elongase, Δ8-desaturase, Δ5-desaturase, Δ5-elongase and/or Δ4-desaturase genes can be expressed in bacterial cells, insect cells (using Baculovirus expression vectors), yeast and other fungal cells (see Romanos, M. A., et al. (1992) "Foreign gene expression in yeast: a review", Yeast 8:423-488; van den Hondel, C. A. M. J. J., et al. (1991) "Heterologous gene expression in filamentous fungi", in: More Gene Manipulations in Fungi, J. W. Bennet & L. L. Lasure, Eds., pp. 396-428: Academic Press: San Diego; and van den Hondel, C. A. M. J. J., & Punt, P. J. (1991) "Gene transfer systems and vector development for filamentous fungi, in: Applied Molecular Genetics of Fungi, Peberdy, J. F., et al., Eds., pp. 1-28, Cambridge University Press: Cambridge), algae (Falciatore et al., 1999, Marine Biotechnology. 1, 3:239-251), ciliates of the types: *Holotrichia, Peritrichia, Spirotrichia, Suctoria, Tetrahymena, Paramecium, Colpidium, Glaucoma, Platyophrya, Potomacus, Desaturaseudocohnilembus, Euplotes, Engelmaniella* and *Stylonychia*, in particular of the genus *Stylonychia lemnae*, using vectors in a transformation method as described in WO 98/01572 and, preferably, in cells of multi-celled plants (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583-586; Plant Molecular Biology and Biotechnology, C Press, Boca Raton, Fla., Chapter 6/7, pp. 71-119 (1993); F. F. White, B. Jenes et al., Techniques for Gene Transfer, in: Transgenic Plants, Vol. 1, Engineering and Utilization, Eds.: Kung and R. Wu, Academic Press (1993), 128-43; Potrykus, Annu. Rev. Plant Physiol. Plant Molec. Biol. 42 (1991), 205-225 (and references cited therein)). Suitable host cells are furthermore discussed in Goeddel, Gene Expression Technology: Methods in Enzymology 185, Academic Press, San Diego, Calif. (1990). As an alternative, the recombinant expression vector can be transcribed and translated in vitro, for example using T7-promoter regulatory sequences and T7-polymerase.

In most cases, the expression of proteins in prokaryotes involves the use of vectors comprising constitutive or inducible promoters which govern the expression of fusion or non-fusion proteins. Typical fusion expression vectors are, inter alia, pGEX (Pharmacia Biotech Inc; Smith, D. B., and Johnson, K. S. (1988) Gene 67:31-40), pMAL (New England Biolabs, Beverly, Mass.) and pRIT5 (Pharmacia, Piscataway, N.J.), where glutathione S-transferase (GST), maltose-E-binding protein and protein A, respectively, are fused with the recombinant target protein. Examples of suitable inducible nonfusion *E. coli* expression vectors are, inter alia, pTrc (Amann et al. (1988) Gene 69:301-315) and pET 11d (Studier et al., Gene Expression Technology: Methods in Enzymology 185, Academic Press, San Diego, Calif. (1990) 60-89). The target gene expression from the vector pTrc is based on the transcription from a hybrid trp-lac fusion promoter by the host RNA polymerase. The target gene expression from the vector pET 11d is based on the transcription of a T7-gn10-lac fusion promoter, which is mediated by a viral RNA polymerase (T7 gn1), which is coexpressed. This viral polymerase is provided by the host strains BL21 (DE3) or HMS174 (DE3) from a resident Aprophagene which harbors a T7 gn1 gene under the transcriptional control of the lacUV 5 promoter. Other vectors which are suitable for prokaryotic organisms are known to the skilled worker, these vectors are, for example in *E. coli* pLG338, pACYC184, the pBR series such as pBR322, the pUC series such as pUC18 or pUC19, the M113 mp series, pKC30, pRep4, pHS1, pHS2, pPLc236, pMBL24, pLG200, pUR290, pIN-III113-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667.

In a further embodiment, the expression vector is a yeast expression vector. Examples of vectors for expression in the yeast *S. cerevisiae* comprise pYeDesaturasec1 (Baldari et al. (1987) Embo J. 6:229-234), pMFa (Kurjan and Herskowitz (1982) Cell 30:933-943), pJRY88 (Schultz et al. (1987) Gene 54:113-123) and pYES2 (Invitrogen Corporation, San Diego, Calif.). Vectors and methods for the construction of vectors which are suitable for use in other fungi, such as the filamentous fungi, comprise those which are described in detail in: van den Hondel, C. A. M. J. J., & Punt, P. J. (1991) "Gene transfer systems and vector development for filamentous fungi, in: Applied Molecular Genetics of fungi, J. F. Peberdy et al., Ed., pp. 1-28, Cambridge University Press: Cambridge, or in: More Gene Manipulations in Fungi [J. W. Bennet & L. L. Lasure, Eds., pp. 396-428: Academic Press: San Diego]. Further suitable yeast vectors are, for example, pAG-1, YEp6, YEp13 or pEMBLYe23.

As an alternative, the polynucleotides of the present invention can also be expressed in insect cells using Baculovirus expression vectors. Baculovirus vectors which are available for the expression of proteins in cultured insect cells (for example Sf9 cells) comprise the pAc series (Smith et al. (1983) Mol. Cell. Biol. 3:2156-2165) and the pVL series (Lucklow and Summers (1989) Virology 170:31-39).

Preferred plant expression vectors comprise those which are described in detail in: Becker, D., Kemper, E., Schell, J., and Masterson, R. (1992) "New plant binary vectors with selectable markers located proximal to the left border", Plant Mol. Biol. 20:1195-1197; and Bevan, M. W. (1984) "Binary *Agrobacterium* vectors for plant transformation", Nucl. Acids Res. 12:8711-8721; Vectors for Gene Transfer in Higher Plants; in: Transgenic Plants, Vol. 1, Engineering and Utilization, Eds.: Kung and R. Wu, Academic Press, 1993, p. 15-38. A plant expression cassette preferably comprises expression control sequences which are capable of governing the expression of genes in plant cells and which are linked operably so that each sequence can fulfill its function, such as transcriptional termination, for example polyadenylation signals. Preferred polyadenylation signals are those which are derived from *Agrobacterium tumefaciens* T-DNA, such as gene 3 of the Ti plasmid pTiACH5 (Gielen et al., EMBO J. 3 (1984) 835 et seq.), which is known as octopine synthase, or functional equivalents thereof, but all other terminators which are functionally active in plants are also suitable. Since plant gene expression is very often not limited to transcriptional levels, a plant expression cassette preferably comprises other sequences which are linked operably, such as translation enhancers, for example the overdrive sequence, which comprises the tobacco mosaic virus 5'-untranslated leader sequence, which increases the protein/RNA ratio (Gallie et al., 1987, Nucl. Acids Research 15:8693-8711). As described above, plant gene expression must be linked operably with a suitable promoter which triggers gene expression with the correct timing or in a cell- or tissue-specific manner. Utilizable promoters are constitutive promoters (Benfey et al., EMBO J. 8 (1989) 2195-2202), such as those which are derived from plant viruses, such as 35S CAMV (Franck et al., Cell 21 (1980) 285-294), 19S CaMV (see also U.S. Pat. No. 5,352,605 and WO 84/02913), or plant promoters, such as the promoter of the small Rubisco subunit, which is described in U.S. Pat. No. 4,962,028. Other preferred sequences for use in operable linkage in plant gene expression cassettes are targeting sequences, which are required for steering the gene product into its corresponding cell compartment (see a review in Kermode, Crit. Rev. Plant Sci. 15, 4 (1996) 285-423 and references cited therein), for example into the vacuole, into the nucleus, all types of plastids, such as amyloplasts, chloroplasts, chromoplasts, the extracellular space, the mitochondria, the endoplasmic reticulum, oil bodies, peroxisomes and other compartments of plant cells. As described above, plant gene expression can also be facilitated via a chemically inducible promoter (see review in Gatz 1997, Annu. Rev. Plant Physiol. Plant Mol. Biol., 48:89-108). Chemically inducible promoters are particularly suitable when it is desired that the gene expression takes place in a time-specific manner. Examples of such promoters are a salicylic-acid-inducible promoter (WO 95/19443), a tetracyclin-inducible promoter (Gatz et al. (1992) Plant J. 2, 397-404) and an ethanol-inducible promoter. Promoters which respond to biotic or abiotic stress conditions are also suitable, for example the pathogen-induced PRP1 gene promoter (Ward et al., Plant. Mol. Biol. 22 (1993) 361-366), the heat-inducible tomato hsp80 promoter (U.S. Pat. No. 5,187,267), the chill-inducible potato alpha-amylase promoter (WO 96/12814) or the wound-inducible pinII promoter (EP-A-0 375 091).

Especially preferred are those promoters which bring about the gene expression in tissues and organs in which the biosynthesis of fatty acids, lipids and oils takes place, in seed cells, such as the cells of the endosperm and of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3):459-67), the *Arabidopsis* oleosin promoter (WO 98/45461), the *Phaseolus vulgaris* phaseolin promoter (U.S. Pat. No. 5,504,200), the *Brassica* Bce4 promoter (WO 91/13980) or the legumine B4 promoter (LeB4; Baeumlein et al., 1992, Plant Journal, 2 (2):233-9), and promoters which bring about the seed-specific expression in monocotyledonous plants such as maize, barley, wheat, rye, rice and the like. Suitable noteworthy promoters are the barley lpt2 or lpt1 gene promoter (WO 95/15389 and WO 95/23230) or the promoters from the barley hordein gene, the rice glutelin gene, the rice oryzin gene, the rice prolamine gene, the wheat gliadine gene, the wheat glutelin gene, the maize zeine gene, the oat glutelin gene, the sorghum kasirin gene or the rye secalin gene, which are described in WO 99/16890. Especially suitable promoters are likewise those which bring about the plastid-specific expression, since plastids are the compartment in which the precursors and some of the end products of lipid biosynthesis are synthesized. Suitable promoters, such as the viral RNA polymerase promoter, are described in WO 95/16783 and WO 97/06250, and the clpP promoter from *Arabidopsis*, described in WO 99/46394.

The abovementioned vectors are only a small overview over possible vectors which are suitable. Further plasmids are known to the skilled worker and are described for example in: Cloning Vectors (eds. Pouwels, P. H., et al., Elsevier, AmsterdamNew York-Oxford, 1985, ISBN 0 444 904018). Further suitable expression systems for prokaryotic and eukaryotic cells, see chapters 16 and 17 of Sambrook, J., Fritsch, E. F., and Maniatis, T., Molecular Cloning: A Laboratory Manual, $2^{nd}$ ed., Cold Spring Harbor Laboratory, Cold Spring Harbor Laboratory Press, Cold Spring Harbor, N.Y., 1989.

As described above, the expression vector can, in addition to the polynucleotides according to the invention, also comprise further genes which are to be introduced into the organisms. It is possible and preferred to introduce into the host organisms, and express in them, regulatory genes, such as genes for inductors, repressors or enzymes which, as a result of their enzymatic activity, engage in the regulation of one or more genes of a biosynthetic pathway. These genes can be of heterologous or homologous origin. Heterologous genes or polynucleotides are derived from an organism of origin which differs from the target organism into which the genes or polynucleotides are to be introduced. In the case of homologous genes or polynucleotides, target organism and organism of origin are identical. The vector therefore preferably comprises at least one further polynucleotide which codes for a further enzyme which is involved in the biosynthesis of lipids or fatty acids. The enzyme is preferably selected from the group consisting of: acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s), fatty acid elongase(s), Δ4-desaturase(s), Δ5-desaturase(s), Δ6-desaturase(s), Δ8-desaturase(s), Δ9-desaturase(s), Δ12-desaturase(s), Δ15-desaturase(s), Δ12- and Δ15-desaturase(s), ω3-desaturase, Δ5-elongase(s), Δ6-elongase(s) and Δ9-elongase(s). Especially preferred gene combinations are listed in tables 5 and 6 in the examples which follow.

The invention also relates to a host cell which comprises the polynucleotide according to the invention or the vector according to the invention.

In principle, host cells for the purposes of the present invention may be all eukaryotic or prokaryotic cells. They may be primary cells from animals, plants or multi-celled microorganisms, for example from those which are mentioned in another place in the description. The term furthermore also comprises cell lines which can be obtained from these organisms.

However, host cells for the purposes of the invention may also be single-celled microorganisms, for example bacteria or fungi. Especially preferred microorganisms are fungi selected from the group of the families Chaetomiaceae, Choanephoraceae, Cryptococcaceae, Cunninghamellaceae, Demetiaceae, Moniliaceae, Mortierellaceae, Mucoraceae, Pythiaceae, Sacharomycetaceae, Saprolegniaceae, Schizosacharomycetaceae, Sodariaceae or Tuberculariaceae. Further preferred microorganisms are selected from the group: Choanephoraceae, such as the genera *Blakeslea*, *Choanephora*, for example the genera and species *Blakeslea trispora*, *Choanephora cucurbitarum*, *Choanephora infundibulifera* var. *cucurbitarum*, Mortierellaceae, such as the genus *Mortierella*, for example the genera and species *Mortierella isabellina*, *Mortierella polycephala*, *Mortierella ramanniana*, *Mortierella vinacea*, *Mortierella zonata*, the family Mucorales, such as the genera and species *Rhizopus oryzae*, *Rhizopus stolonifer*, *Fusarium graminearium*, Pythiaceae, such as the genera *Phytium*, *Phytophthora*, for example the genera and species *Pythium debaryanum*, *Pythium intermedium*, *Pythium irregulare*, *Pythium megalacanthum*, *Pythium paroecandrum*, *Pythium sylvaticum*, *Pythium ultimum*, *Phytophthora cactorum*, *Phytophthora cinnamoms*, *Phytophthora citricola*, *Phytophthora citrophthora*, *Phytophthora cryptogea*, *Phytophthora drechsleri*, *Phytophthora erythroseptica*, *Phytophthora lateralis*, *Phytophthora megasperma*, *Phytophthora nicotianae*, *Phytophthora nicotianae* var. *parasitica*, *Phytophthora palmivora*, *Phytophthora parasitica*, *Phytophthora syringae*, Saccharomycetaceae, such as the genera *Hansenula*, *Pichia*, *Saccharomyces*, *Saccharomycodes*, *Yarrowia*, for example the genera and species *Hansenula anomala*, *Hansenula cafifomica*, *Hansenula canadensis*, *Hansenula capsulata*, *Hansenula ciferrii*, *Hansenula glucozyma*, *Hansenula henricii*, *Hansenula holstfi*, *Hansenula minuta*, *Hansenula nonfermentans*, *Hansenula philodendri*, *Hansenula polymorpha*, *Hansenula saturnus*, *Hansenula subpelliculosa*, *Hansenula wickerhamii*, *Hansenula wingei*, *Pichia alcoholophila*, *Pichia angusta*, *Pichia anomala*, *Pichia bispora*, *Pichia burtonfi*, *Pichia canadensis*, *Pichia capsulata*, *Pichia carsonii*, *Pichia cellobiosa*, *Pichia ciferrii*, *Pichia farinosa*, *Pichia fermentans*, *Pichia finlandica*, *Pichia glucozyma*, *Pichia gufifiermondfi*, *Pichia haplophila*, *Pichia henricii*, *Pichia holstfi*, *Pichia jadinii*, *Pichia findnerfi*, *Pichia membranaefaciens*, *Pichia methanolica*, *Pichia minuta* var. *minuta*, *Pichia minuta* var. *nonfermentans*, *Pichia norvegensis*, *Pichia ohmeri*, *Pichia pastoris*, *Pichia philodendri*, *Pichia pini*, *Pichia polymorpha*, *Pichia quercuum*, *Pichia rhodanensis*, *Pichia sargentensis*, *Pichia stipitis*, *Pichia strasburgensis*, *Pichia subpelficulosa*, *Pichia toletana*, *Pichia trehalophila*, *Pichia vini*, *Pichia xylosa*, *Saccharomyces aceta*, *Saccharomyces bairn*, *Saccharomyces bayanus*, *Saccharomyces bisporus*, *Saccharomyces capensis*, *Saccharomyces carlsbergensis*, *Saccharomyces cerevisiae*, *Saccharomyces cerevisiae* var. *elfipsoideus*, *Saccharomyces chevafieri*, *Saccharomyces delbrueckfi*, *Saccharomyces diastaticus*, *Saccharomyces drosophilarum*, *Saccharomyces elegans*, *Saccharomyces elfipsoideus*, *Saccharomyces fermentati*, *Saccharomyces florentinus*, *Saccharomyces fragilis*, *Saccharomyces heterogenicus*, *Saccharomyces hienipiensis*, *Saccharomyces inusitatus*, *Saccharomyces italicus*, *Saccharomyces kluyveri*, *Saccharomyces krusei*, *Saccharomyces lactis*, *Saccharomyces marxianus*, *Saccharomyces microelfipsoides*, *Saccharomyces montanus*, *Saccharomyces norbensis*, *Saccharomyces oleaceus*, *Saccharomyces paradoxus*, *Saccharomyces pastorianus*, *Saccharomyces pretoriensis*, *Saccharomyces rosea*, *Saccharomyces rouxii*, *Saccharomyces uvarum*, *Saccharomycodes ludwigii*, *Yarrowia fipolyfica*, Schizosaccharomycetaceae such as the genera *Schizosaccharomyces* e.g. the species *Schizosaccharomyces japonicus* var. *japonicus*, *Schizosaccharomyces japonicus* var. *versatilis*, *Schizosaccharomyces malidevorans*, *Schizosaccharomyces octosporus*, *Schizosaccharomyces pombe* var. *malidevorans*, *Schizosaccharomyces pombe* var. *pombe*, Thraustochytriaceae such as the genera *Althornia*, *Aplanochytrium*, *Japonochytrium*, *Schizochytrium*, *Thraustochytrium* e.g. the species *Schizochytrium aggregatum*, *Schizochytrium limacinum*,

*Schizochytrium mangrovei, Schizochytrium minutum, Schizochytrium octosporum, Thraustochytrium aggregatum, Thraustochytrium amoeboideum, Thraustochytrium antacticum, Thraustochytrium arudimentale, Thraustochytrium aureum, Thraustochytrium benthicola, Thraustochytrium globosum, Thraustochytrium indicum, Thraustochytrium kerguelense, Thraustochytrium kinnei, Thraustochytrium motivum, Thraustochytrium multirudimentale, Thraustochytrium pachydermum, Thraustochytrium proliferum, Thraustochytrium roseum, Thraustochytrium rossii, Thraustochytrium striatum* or *Thraustochytrium visurgense*.

Equally preferred as microorganisms are bacteria selected from the group of the families Bacillaceae, Enterobacteriacae or Rhizobiaceae. It is especially preferred to mention the following bacteria selected from the group: Bacillaceae, such as the genus *Bacillus*, for example the genera and species *Bacillus acidocaldarius, Bacillus acidoterrestris, Bacillus alcalophilus, Bacillus amyloliquefaciens, Bacillus amylolyticus, Bacillus brevis, Bacillus cereus, Bacillus circulans, Bacillus coagulans, Bacillus sphaericus* subsp. *fusiformis, Bacillus galactophilus, Bacillus globisporus, Bacillus globisporus* subsp. *marinus, Bacillus halophilus, Bacillus lentimorbus, Bacillus lentus, Bacillus licheniformis, Bacillus megaterium, Bacillus polymyxa, Bacillus psychrosaccharolyticus, Bacillus pumilus, Bacillus sphaericus, Bacillus subtilis* subsp. *spizizenii, Bacillus subtilis* subsp. *subtilis* or *Bacillus thuringiensis*; Enterobacteriacae such as the genera *Citrobacter, Edwardsiella, Enterobacter, Erwinia, Escherichia, Klebsiella, Salmonella* or *Serratia*, for example the genera and species *Citrobacter amalonaticus, Citrobacter diversus, Citrobacter freundii, Citrobacter genomospecies, Citrobacter gillenii, Citrobacter intermedium, Citrobacter koseri, Citrobacter murliniae, Citrobacter sp., Edwardsiella hoshinae, Edwardsiella ictaluri, Edwardsiella tarda, Erwinia alni, Erwinia amylovora, Erwinia ananatis, Erwinia aphidicola, Erwinia billingiae, Erwinia cacticida, Erwinia cancerogena, Erwinia carnegieana, Erwinia carotovora* subsp. *atroseptica, Erwinia carotovora* subsp. *betavasculorum, Erwinia carotovora* subsp. *odorifera, Erwinia carotovora* subsp. *wasabiae, Erwinia chtysanthemi, Erwinia cypripedii, Erwinia dissolvens, Erwinia herbicola, Erwinia mallotivora, Erwinia milletiae, Erwinia nigrifluens, Erwinia nimipressuralis, Erwinia persicina, Erwinia psidii, Erwinia pyrifoliae, Erwinia quercina, Erwinia rhapontici, Erwinia rubrifaciens, Erwinia salicis, Erwinia stewartii, Erwinia tracheiphila, Erwinia uredovora, Escherichia adecarboxylata, Escherichia anindolica, Escherichia aurescens, Escherichia blattae, Escherichia coli, Escherichia coli* var. *communion, Escherichia coli-mutabile, Escherichia fergusonii, Escherichia hermannii, Escherichia sp., Escherichia vulneris, Klebsiella aerogenes, Klebsiella edwardsii* subsp. *atlantae, Klebsiella ornithinolytica, Klebsiella oxytoca, Klebsiella planticola, Klebsiella pneumoniae, Klebsiella pneumoniae* subsp. *pneumoniae, Klebsiella sp., Klebsiella terrigena, Klebsiella trevisanii, Salmonella abony, Salmonella arizonae, Salmonella bongori, Salmonella choleraesuis* subsp. *arizonae, Salmonella choleraesuis* subsp. *bongori, Salmonella choleraesuis* subsp. *choleraesuis, Salmonella choleraesuis* subsp. *diarizonae, Salmonella choleraesuis* subsp. *houtenae, Salmonella choleraesuis* subsp. *indica, Salmonella choleraesuis* subsp. *salamae, Salmonella daressalaam, Salmonella enterica* subsp. *houtenae, Salmonella enterica* subsp. *salamae, Salmonella enteritidis, Salmonella gallinarum, Salmonella heidelberg, Salmonella panama, Salmonella senftenberg, Salmonella typhimurium, Serratia entomophila, Serratia ficaria, Serratia fonticola, Serratia grimesii, Serratia liquefaciens, Serratia marcescens, Serratia marcescens* subsp. *marcescens, Serratia marinorubra, Serratia odorifera, Serratia plymouthensis, Serratia plymuthica, Serratia proteamaculans, Serratia proteamaculans* subsp. *quinovora, Serratia quinivorans* or *Serratia rubidaea*; Rhizobiaceae, such as the genera *Agrobacterium, Carbophilus, Chelatobacter, Ensifer, Rhizobium, Sinorhizobium*, for example the genera and species *Agrobacterium atlanticum, Agrobacterium ferrugineum, Agrobacterium gelatinovorum, Agrobacterium lanymoorei, Agrobacterium meteori, Agrobacterium radiobacter, Agrobacterium rhizogenes, Agrobacterium rubi, Agrobacterium stellulatum, Agrobacterium tumefaciens, Agrobacterium vitis, Carbophilus carboxidus, Chelatobacter heintzii, Ensifer adhaerens, Ensifer arboris, Ensifer fredii, Ensifer kostiensis, Ensifer kummerowiae, Ensifer medicae, Ensifer meliloti, Ensifer saheli, Ensifer terangae, Ensifer xinjiangensis, Rhizobium ciceri, Rhizobium etli, Rhizobium fredii, Rhizobium galegae, Rhizobium gallicum, Rhizobium giardinii, Rhizobium hainanense, Rhizobium huakuii, Rhizobium huautlense, Rhizobium indigoferae, Rhizobium japonicum, Rhizobium leguminosarum, Rhizobium loessense, Rhizobium loti, Rhizobium lupini, Rhizobium mediterraneum, Rhizobium meliloti, Rhizobium mongolense, Rhizobium phaseoli, Rhizobium radiobacter, Rhizobium rhizogenes, Rhizobium rubi, Rhizobium sullae, Rhizobium tianshanense, Rhizobium trifolii, Rhizobium tropici, Rhizobium undicola, Rhizobium vitis, Sinorhizobium adhaerens, Sinorhizobium arboris, Sinorhizobium fredii, Sinorhizobium kostiense, Sinorhizobium kummerowiae, Sinorhizobium medicae, Sinorhizobium meliloti, Sinorhizobium morelense, Sinorhizobium saheli* or *Sinorhizobium xinjiangense*.

Further utilizable host cells are detailed in: Goeddel, Gene Expression Technology: Methods in Enzymology 185, Academic Press, San Diego, Calif. (1990). Expression strains which can be used, for example those with a lower protease activity, are described in: Gottesman, S., Gene Expression Technology: Methods in Enzymology 185, Academic Press, San Diego, Calif. (1990) 119-128. These include plant cells and certain tissues, organs and parts of plants in all their phenotypic forms such as anthers, fibers, root hairs, stalks, embryos, calli, cotelydons, petioles, harvested material, plant tissue, reproductive tissue and cell cultures which are derived from the actual transgenic plant and/or can be used for bringing about the transgenic plant.

Polynucleotides or vectors can be introduced into the host cell as described above by means of transformation or transfection methods which are known in the prior art. Conditions and media for the cultivation of the host cells are also known to the skilled worker.

The host cell according to the invention preferably additionally comprises at least one further enzyme which is involved in the biosynthesis of lipids or fatty acids. Preferred enzymes have already been mentioned in another place in the description. The enzyme can be present in the host cell in endogenous form, i.e. the host cell already naturally expresses a gene which codes for a corresponding enzyme. Alternatively, it is also possible to introduce, into the host cell, a heterologous polynucleotide which codes for the enzyme. Suitable methods and means for the expression of a heterologous polynucleotide are known in the prior art and are described herein in connection with the polynucleotides, vectors and host cells according to the invention.

The invention also relates to a method of generating a polypeptide with desaturase activity, comprising the steps:
(a) expressing a polynucleotide according to the invention as defined above in a host cell; and (b) obtaining, from the host cell, the polypeptide which is encoded by the polynucleotide.

In this context, the polypeptide can be obtained or isolated by all current protein purification methods. The methods comprise, for example, affinity chromatography, molecular sieve chromatography, high-pressure liquid chromatography or else protein precipitation, if appropriate with specific antibodies. Although this is preferred, the method need not necessarily provide a pure polypeptide preparation.

The invention therefore also relates to a polypeptide which is encoded by the polynucleotide according to the invention or which is obtainable by the abovementioned method according to the invention.

The term "polypeptide" refers both to an essentially pure polypeptide, and also to a polypeptide preparation which additionally comprises further components or impurities. The term is also used for fusion proteins and protein aggregates which comprise the polypeptide according to the invention and additionally further components. The term also refers to chemically modified polypeptides. In this context, chemical modifications comprise artificial modifications or naturally occurring modifications, for example posttranslational modifications such as phosphorylation, myristylation, glycosylation and the like. The terms polypeptide, peptide and protein are interchangeable and are used accordingly in the description and in the prior art. The polypeptides according to the invention have the abovementioned biological activities, that is to say desaturase activities, and can influence the biosynthesis of polyunsaturated fatty acids (PUFAs), preferably the long-chain PUFAs (LCPUFAs), as herein described.

The invention also comprises an antibody which specifically recognizes the polypeptide according to the invention.

Antibodies against the polypeptide according to the invention can be prepared by means of known methods, where purified polypeptide or fragments thereof with suitable epitopes are used as the antigen. Suitable epitopes can be determined by means of known algorithms for the antigenicity determination, based on the amino acid sequences of the polypeptides according to the invention provided herein. The relevant polypeptides or fragments can then be synthesized or obtained by recombinant techniques. After animals, preferably mammals, for example hares, rats or mice, have been immunized, the antibodies can then be obtained from the serum, using known methods. Alternatively, monoclonal antibodies or antibody fragments can be provided with the known methods; see, for example, Harlow and Lane "Antibodies, A Laboratory Manual", CSH Press, Cold Spring Harbor, 1988 or Köhler and Milstein, Nature 256 (1975), 495, and Galfré, Meth. Enzymol. 73 (1981), 3.

The antibodies preferably take the form of monoclonal or polyclonal antibodies, single-chain antibodies or chimeric antibodies, and fragments of these such as Fab, Fv or scFv. Further antibodies within the meaning of the invention are bispecific antibodies, synthetic antibodies or their chemically modified derivatives.

The antibodies according to the invention specifically recognize the polypeptides according to the invention, that is to say they do not cross-react significantly with other proteins. This can be assayed by means of methods known in the prior art. For example, the antibodies can be employed for the purposes of detection reactions, immunoprecipitation, immunhistochemistry or protein purification (for example affinity chromatography).

The invention furthermore relates to a transgenic, nonhuman organism which comprises the polynucleotide, the vector or the host cell of the present invention. The transgenic, nonhuman organism preferably takes the form of an animal, a plant or a multicellular microorganism.

The term "transgenic" is understood as meaning that a heterologous polynucleotide, that is to say a polynucleotide which does not occur naturally in the respective organism, is introduced into the organism. This can be achieved either by random insertion of the polynucleotide or by homologous recombination. Naturally, it is also possible to introduce the vector according to the invention instead of the polynucleotide. Methods of introducing polynucleotides or vectors for the purposes of random insertion or homologous recombination are known in the prior art and also described in greater detail hereinbelow. Host cells which comprise the polynucleotide or the vector can also be introduced into an organism and thus generate a transgenic organism. In such a case, such an organism takes the form of a chimeric organism, where only those cells which are derived from the introduced cells are transgenic, i.e. comprise the heterologous polynucleotide.

The transgenic nonhuman organisms are preferably oil-producing organisms, which means organisms which are used for the production of oils, for example fungi such as *Rhizopus* or *Thraustochytrium*, algae such as *Euglena, Nephroselmis, Pseudoscourfielda, Prasinococcus, Scherffelia, Tetraselmis, Mantoniella, Ostreococcus, Crypthecodinium, Phaeodactylum*, or diatoms such as *Pythium* or *Phytophthora* or plants.

Transgenic plants which can be used are, in principle, are all plants, that is to say both dicotyledonous and monocotyledonous plants. They preferably take the form of oil crop plants which comprise large amounts of lipid compounds, such as peanut, oilseed rape, canola, sunflower, safflower (*Carthamus tinctoria*), poppy, mustard, hemp, castor-oil plant, olive, sesame, *Calendula, Punica*, evening primrose, verbascum, thistle, wild roses, hazelnut, almond, *macadamia*, avocado, bay, pumpkin/squash, linseed, soybean, pistachios, borage, trees (oil palm, coconut or walnut) or arable crops such as maize, wheat, rye, oats, triticale, rice, barley, cotton, cassava, pepper, Tagetes, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are plants which are high in C18:2- and/or C18:3-fatty acids, such as sunflower, safflower, tobacco, verbascum, sesame, cotton, pumpkin/squash, poppy, evening primrose, walnut, linseed, hemp, thistle or safflower. Very especially preferred plants are plants such as safflower, sunflower, poppy, evening primrose, walnut, linseed or hemp. In principle, however, all plants which are capable of synthesizing fatty acids are suitable, such as all dicotyledonous or monocotyledonous plants, algae or mosses. Advantageous plants are selected from the group of the plant families Adelotheciaceae, Anacardiaceae, Asteraceae, Apiaceae, Betulaceae, Boraginaceae, Brassicaceae, Bromeliaceae, Caricaceae, Cannabaceae, Convolvulaceae, Chenopodiaceae, Crypthecodiniaceae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Prasinophyceae or vegetable plants or ornamentals such as Tagetes.

Examples which may especially preferably be mentioned are the following plants selected from the group consisting of: Adelotheciaceae such as the genera *Physcomitrella*, for example the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Clchorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Camelina, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Camelina sativa, Melanosinapis communis* [mustard], *Brassica oleracea* [fodder beet] or *Arabadopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sative* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae, such as the genera *Amphora, Cymbella, Okedenia, Phaeodactylum, Reimeria*, for example the genus and species *Phaeodactylum tricornutum*, Ditrichaceae, such as the genera *Ditrichaceae, Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon columbiae, Ceratodon heterophyllus, Ceratodon purpurascens, Ceratodon purpureus, Ceratodon purpureus* ssp. *convolutus, Ceratodon purpureus* ssp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium altemifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae, such as the genus *Elaeagnus*, for example the genus and species *Olea europaea* [olive], Ericaceae, such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae, such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [cassava] or *Ricinus communis* [castor-oil plant], Fabaceae, such as the genera *Pisum, Albizia, Cathormion, Feuillea, Inga, Pithecolobium, Acacia, Mimosa, Medicajo, Glycine, Dolichos, Phaseolus*, soybean, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbeck, Feuilleea lebbeck, Mimosa lebbeck, Mimosa speciosa* [silk tree], *Medicago sativa, Medicago falcata, Medicago varia* [alfalfa] *Glycine max Dolichos soja, Glycine gracilis, Glycine hispida, Phaseolus max, Soja hispida* or *Soja max* [soybean], Funariaceae, such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physcomitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or Oleum cocois [coconut], Gramineae, such as the genus *Saccharum*, for example the genus and species *Saccharum officinarum*, Juglandaceae, such as the genera *Juglans*, *Wallia*, for example the genera and species *Juglans regia*, *Juglans ailanthifolia*, *Juglans sieboldiana*, *Juglans cinerea*, *Wallia cinerea*, *Juglans bixbyi*, *Juglans californica*, *Juglans hindsii*, *Juglans intermedia*, *Juglans jamaicensis*, *Juglans major*, *Juglans microcarpa*, *Juglans nigra* or *Wallia nigra* [walnut], Lauraceae, such as the genera *Persea*, *Laurus*, for example the genera and species *Laurus nobilis* [bay], *Persea americana*, *Persea gratissima* or *Persea persea* [avocado], Leguminosae, such as the genus *Arachis*, for example the genus and species *Arachis hypogaea* [peanut], Linaceae, such as the genera *Linum*, *Adenolinum*, for example the genera and species *Linum usitatissimum*, *Linum humile*, *Linum austriacum*, *Linum bienne*, *Linum angustifolium*, *Linum catharticum*, *Linum flavum*, *Linum grandiflorum*, *Adenolinum grandiflorum*, *Linum lewisii*, *Linum narbonense*, *Linum perenne*, *Linum perenne* var. *lewisii*, *Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum*, *Gossypium arboreum*, *Gossypium barbadense*, *Gossypium herbaceum* or *Gossypium thurberi* [cotton], Marchantiaceae, such as the genus *Marchantia*, for example the genera and species *Marchantia berteroana*, *Marchantia foliacea*, *Marchantia macropora*, Musaceae, such as the genus *Musa*, for example the genera and species *Musa nana*, *Musa acuminata*, *Musa paradisiaca*, *Musa* spp. [banana], Onagraceae, such as the genera *Camissonia*, *Oenothera*, for example the genera and species *Oenothera biennis* or *Camissonia brevipes* [evening primrose], Palmae, such as the genus *Elacis*, for example the genus and species *Elaeis guineensis* [oil palm], Papaveraceae, such as the genus *Papaver*, for example the genera and species *Papaver orientale*, *Papaver rhoeas*, *Papaver dubium* [poppy], Pedaliaceae, such as the genus *Sesamum*, for example the genus and species *Sesamum indicum* [sesame], Piperaceae, such as the genera *Piper*, *Artanthe*, *Peperomia*, *Steffensia*, for example the genera and species *Piper aduncum*, *Piper amalago*, *Piper angustifolium*, *Piper auritum*, *Piper betel*, *Piper cubeba*, *Piper longum*, *Piper nigrum*, *Piper retrofractum*, *Artanthe adunca*, *Artanthe elongata*, *Peperomia elongata*, *Piper elongatum*, *Steffensia elongata* [cayenne pepper], Poaceae, such as the genera *Hordeum*, *Secale*, *Avena*, *Sorghum*, *Andropogon*, *Holcus*, *Panicum*, *Oryza*, *Zea* (maize), *Triticum*, for example the genera and species *Hordeum vulgare*, *Hordeum jubatum*, *Hordeum murinum*, *Hordeum secalinum*, *Hordeum distichon*, *Hordeum aegiceras*, *Hordeum hexastichon*, *Hordeum hexastichum*, *Hordeum irregulare*, *Hordeum sativum*, *Hordeum secalinum* [barley], *Secale cereale* [rye], *Avena sativa*, *Avena fatua*, *Avena byzantina*, *Avena fatua* var. *sativa*, *Avena hybrida* [oats], *Sorghum bicolor*, *Sorghum halepense*, *Sorghum saccharatum*, *Sorghum vulgare*, *Andropogon drummondii*, *Holcus bicolor*, *Holcus sorghum*, *Sorghum aethiopicum*, *Sorghum arundinaceum*, *Sorghum caffrorum*, *Sorghum cernuum*, *Sorghum dochna*, *Sorghum drummondii*, *Sorghum durra*, *Sorghum guineense*, *Sorghum lanceolatum*, *Sorghum nervosum*, *Sorghum saccharatum*, *Sorghum subglabrescens*, *Sorghum verticilliflorum*, *Sorghum vulgare*, *Holcus halepensis*, *Sorghum miliaceum*, *Panicum militaceum* [millet], *Oryza sativa*, *Oryza latifolia* [rice], *Zea mays* [maize] *Triticum aestivum*, *Triticum durum*, *Triticum turgidum*, *Triticum hybernum*, *Triticum macha*, *Triticum sativum* or *Triticum vulgare* [wheat], Porphyridiaceae, such as the genera *Chroothece*, *Flintiella*, *Petrovanella*, *Porphyridium*, *Rhodella*, *Rhodosorus*, *Vanhoeffenia*, for example the genus and species *Porphyridium cruentum*, Proteaceae, such as the genus *Macadamia*, for example the genus and species *Macadamia intergrifolia [macadamia]*, Prasinophyceae, such as the genera *Nephroselmis*, *Prasinococcus*, *Scherffelia*, *Tetraselmis*, *Mantoniella*, *Ostreococcus*, for example the genera and species *Nephroselmis olivacea*, *Prasinococcus capsulatus*, *Scherffelia dubia*, *Tetraselmis chui*, *Tetraselmis suecica*, *Mantoniella squamata*, *Ostreococcus tauri*, Rubiaceae, such as the genus *Coffea*, for example the genera and species *Cofea* spp., *Coffea arabica*, *Coffea canephora* or *Coffea liberica* [coffee], Scrophulariaceae, such as the genus *Verbascum*, for example the genera and species *Verbascum blattaria*, *Verbascum chaixii*, *Verbascum densiflorum*, *Verbascum lagurus*, *Verbascum longifolium*, *Verbascum lychnitis*, *Verbascum nigrum*, *Verbascum olympicum*, *Verbascum phlomoides*, *Verbascum phoenicum*, *Verbascum pulverulentum* or *Verbascum thapsus* [verbascum], Solanaceae, such as the genera *Capsicum*, *Nicotiana*, *Solanum*, *Lycopersicon*, for example the genera and species *Capsicum annuum*, *Capsicum annuum* var. *glabriusculum*, *Capsicum frutescens* [pepper], *Capsicum annuum* [paprika], *Nicotiana tabacum*, *Nicotiana alata*, *Nicotiana attenuata*, *Nicotiana glauca*, *Nicotiana langsdorffii*, *Nicotiana obtusifolia*, *Nicotiana quadrivalvis*, *Nicotiana repanda*, *Nicotiana rustica*, *Nicotiana sylvestris* [tobacco], *Solanum tuberosum* [potato], *Solanum melongena* [eggplant], *Lycopersicon esculentum*, *Lycopersicon lycopersicum*, *Lycopersicon pyriforme*, *Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea].

Multicellular microorganisms which can be employed as transgenic nonhuman organisms are preferably protists or diatoms selected from the group of the families Dinophyceae, Turaniellidae or Oxytrichidae, such as the genera and species: *Crypthecodinium cohnii*, *Phaeodactylum tricomutum*, *Stylonychia mytilus*, *Stylonychia pustulata*, *Stylonychia putrina*, *Stylonychia notophora*, *Stylonychia* sp., *Colpidium campylum* or *Colpidium* sp.

The invention further relates to a method for the production of a substance which has the structure shown in the general formula I hereinbelow

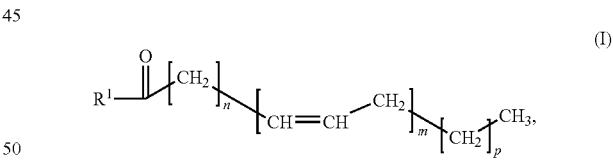

(I)

where the variables and substituents are as follows:
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

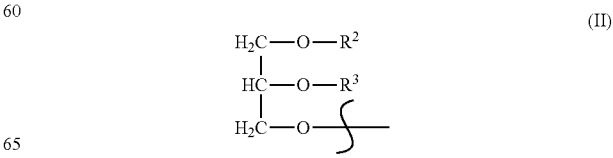

(II)

R²=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, R³=hydrogen, saturated or unsaturated $C_2$-$C_{24}$-alkylcarbonyl, or R² and R³ independently of one another are a radical of the formula Ia:

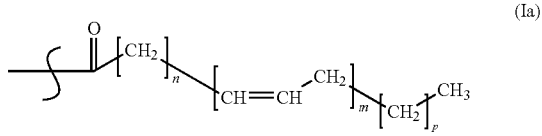

in which
n=2, 3, 4, 5, 6, 7 or 9, m=2, 3, 4, 5 or 6 and p=0 or 3.
and where the method comprises the cultivation of (i) a host cell according to the invention or (ii) a transgenic nonhuman organism according to the invention under conditions which permit the biosynthesis of the substance. Preferably, the abovementioned substance is provided in an amount of at least 1% by weight based on the total lipid content in the host cell or the transgenic organism.

R¹ in the general formula I is hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the general formula II

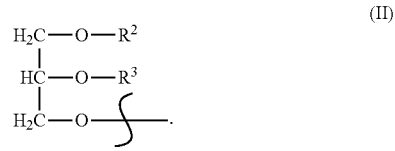

The abovementioned radicals of R¹ are always bonded to the compounds of the general formula I in the form of their thioesters.

R² in the general formula II is hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{1-10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

R³ in the general formula II is hydrogen, saturated or unsaturated $C_2$-$C_{24}$-alkylcarbonyl.

Alkyl radicals which may be mentioned are substituted or unsubstituted, saturated or unsaturated $C_2$-$C_{24}$-alkylcarbonyl chains such as ethylcarbonyl, n-propylcarbonyl, n-butylcarbonyl, n-pentylcarbonyl, n-hexylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl-, n-nonadecylcarbonyl, n-eicosylcarbonyl, n-docosanylcarbonyl or n-tetracosanylcarbonyl, which comprise one or more double bonds. Saturated or unsaturated $C_{10}$-$C_{22}$-alkylcarbonyl radicals such as n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, n-eicosylcarbonyl, n-docosanylcarbonyl or n-tetracosanylcarbonyl, which comprise one or more double bonds are preferred. Especially preferred are saturated and/or unsaturated $C_{10}$-$C_{22}$-alkylcarbonyl radicals such as $C_{1-10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals which comprise one or more double bonds. Very especially preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals which comprise one or more double bonds. These advantageous radicals can comprise two, three, four, five or six double bonds. The especially advantageous radicals with 20 or 22 carbon atoms in the fatty acid chain comprise up to six double bonds, advantageously three, four, five or six double bonds, especially preferably five or six double bonds. All the abovementioned radicals are derived from the corresponding fatty acids.

The abovementioned radicals of R¹, R² and R³ can be substituted by hydroxyl and/or epoxy groups and/or can comprise triple bonds.

The polyunsaturated fatty acids produced in the method according to the invention advantageously comprise at least two, advantageously three, four, five or six, double bonds. The fatty acids especially advantageously comprise four, five or six double bonds. Fatty acids produced in the method advantageously have 18, 20 or 22 C atoms in the fatty acid chain; the fatty acids preferably comprise 20 or 22 carbon atoms in the fatty acid chain. Saturated fatty acids are advantageously reacted to a minor degree, or not at all, with the nucleic acids used in the method. To a minor degree is to be understood as meaning that the saturated fatty acids are reacted with less than 5% of the activity, advantageously less than 3%, especially advantageously with less than 2%, very especially preferably with less than 1, 0.5, 0.25 or 0.125% in comparison with polyunsaturated fatty acids. These fatty acids which have been produced can be produced in the method as a single product or be present in a fatty acid mixture.

Advantageously, the substituents $R^2$ or $R^3$ in the general formulae I and II are, independently of one another, saturated or unsaturated $C_{18}$-$C_{22}$-alkylcarbonyl, especially advantageously, they are, independently of one another, unsaturated $C_{18}$-, $C_{20}$- or $C_{22}$-alkylcarbonyl with at least two double bonds.

The polyunsaturated fatty acids produced in the method are advantageously bound in membrane lipids and/or triacylglycerides, but may also occur in the organisms as free fatty acids or else bound in the form of other fatty acid esters. In this context, they may be present as "pure products" or else advantageously in the form of mixtures of various fatty acids or mixtures of different glycerides. The various fatty acids which are bound in the triacylglycerides can be derived from short-chain fatty acids with 4 to 6 C atoms, medium-chain fatty acids with 8 to 12 C atoms or long-chain fatty acids with 14 to 24 C atoms; preferred are long-chain fatty acids, more preferably long-chain polyunsaturated fatty acids with 18, 20 and/or 22 C atoms.

The method according to the invention advantageously yields fatty acid esters with polyunsaturated $C_{18}$-, $C_{20}$- and/or $C_{22}$-fatty acid molecules with at least two double bonds in the fatty acid ester, advantageously with at least three, four, five or six double bonds in the fatty acid ester, especially advantageously with at least five or six double bonds in the fatty acid ester and advantageously leads to the synthesis of linoleic acid (=LA, $C18:2^{\Delta 9,12}$), γ-linolenic acid (=GLA, $C18:3^{\Delta 6,9,12}$), stearidonic acid (=SDA, $C18:4^{\Delta 6,9,12,15}$), dihomo-γ-linolenic acid (=DGLA, $20:3^{\Delta 8,11,14}$), ω3-eicosatetraenoic acid (=ETA, $C20:4^{\Delta 5,8,11,14}$), arachidonic acid (ARA, $C20:4^{\Delta 5,8,11,14}$), eicosapentaenoic acid (EPA, $C20:5^{\Delta 5,8,11,14,17}$), ω6-docosapentaenoic acid ($C22:5^{\Delta 4,7,10,13,16}$), ω6-docosatetraenoic acid ($C22:4^{\Delta 7,10,13,16}$), ω3-docosapentaenoic acid (=DPA, $C22:5^{\Delta 7,10,13,16,19}$), docosahexaenoic acid (=DHA, $C22:6^{\Delta 4,7,10,13,16,19}$) or mixtures of these, preferably ARA, EPA and/or DHA. ω3-Fatty acids such as EPA and/or DHA are very especially preferably produced.

The fatty acid esters with polyunsaturated $C_{18}$-, $C_{20}$- and/or $C_{22}$-fatty acid molecules can be isolated in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacyl-glycerides, diacylglycerides, triacylglycerides or other fatty acid esters such as the acetylcoenzyme A esters which comprise the polyunsaturated fatty acids with at least two, three, four, five or six, preferably five or six double bonds, from the organisms which have been used for the preparation of the fatty acid esters; advantageously, they are isolated in the form of their diacylglycerides, triacylglycerides and/or in the form of phosphatidylcholine, especially preferably in the form of the triacylglycerides. In addition to these esters, the polyunsaturated fatty acids are also present in the organisms, advantageously the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight.

The method according to the invention yields the LCPUFAs produced in a content of at least 3% by weight, advantageously at least 5% by weight, preferably at least 8% by weight, especially preferably at least 10% by weight, most preferably at least 15% by weight, based on the total fatty acids in the transgenic organisms, advantageously in a transgenic plant. In this context, it is advantageous to convert $C_{18}$- and/or $C_{20}$-fatty acids which are present in the host organisms to at least 10%, advantageously to at least 20%, especially advantageously to at least 30%, most advantageously to at least 40% to give the corresponding products such as DPA or DHA, to mention just two examples. The fatty acids are advantageously produced in bound form. These unsaturated fatty acids can, with the aid of the nucleic acids used in the method according to the invention, be positioned at the sn1, sn2 and/or sn3 position of the advantageously produced triglycerides. Since a plurality of reaction steps are performed by the starting compounds linoleic acid (C18:2) and linolenic acid (C18:3) in the method according to the invention, the end products of the method such as, for example, arachidonic acid (ARA), eicosapentaenoic acid (EPA), ω6-docosapentaenoic acid or DHA are not obtained as absolutely pure products; minor traces of the precursors are always present in the end product. If, for example, both linoleic acid and linolenic acid are present in the starting organism and the starting plant, the end products such as ARA, EPA or DHA are present as mixtures. The precursors should advantageously not amount to more than 20% by weight, preferably not to more than 15% by weight, especially preferably not to more than 10% by weight, most preferably not to more than 5% by weight, based on the amount of the end product in question. Advantageously, only ARA, EPA or only DHA, bound or as free acids, are produced as end products in a transgenic plant in the method according to the invention. If the compounds ARA, EPA and DHA are produced simultaneously, they are advantageously produced in a ratio of at least 1:1:2 (EPA:ARA:DHA), advantageously of at least 1:1:3, preferably 1:1:4, especially preferably 1:1:5.

Fatty acid esters or fatty acid mixtures produced by the method according to the invention advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the method of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (β-hydroxy-9c,11t-octadecadienoic acid). The abovementioned fatty acids are, as a rule, advantageously only found in traces in the fatty acid esters or fatty acid mixtures produced by the method according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the method according to the invention advantageously comprise less than 0.1%, based on the total fatty acids, or no butyric acid, no cholesterol, no clupanodonic acid (=docosapentaenoic acid, $C22:5^{\Delta 4,8,12,15,21}$) and no nisinic acid (tetracosahexaenoic acid, $C23:6^{\Delta 3,8,12,15,18,21}$). Owing to the nucleic acid sequences of the invention, or the nucleic acid sequences used in the method according to the invention, an increase in the yield of polyunsaturated fatty acids of at least 50%, advantageously of at least 80%, especially advantageously of at least 100%, very especially advantageously of at least 150%, in comparison with the nontransgenic starting organism, for example a yeast, an alga, a fungus or a plant such as *Arabidopsis* or linseed can be obtained in a comparison by GC analysis.

Chemically pure polyunsaturated fatty acids or fatty acid compositions can also be prepared by the methods described above. To this end, the fatty acids or the fatty acid compositions are isolated from the organism, such as the microorganisms or the plants or the culture medium in or on which the organisms have been grown, or from the organism and the culture medium, in a known manner, for example via extraction, distillation, crystallization, chromatography or combinations of these methods. These chemically pure fatty acids or fatty acid compositions are advantageous for applications in the food industry sector, the cosmetic industry sector and especially the pharmacological industry sector.

In principle, all genes of the fatty acid or lipid metabolism can be used in the method for the production of polyunsaturated fatty acids, advantageously in combination with the inventive polynucleotide(s) (for the purposes of the present application, the plural is understood as encompassing the singular and vice versa). Genes of the fatty acid or lipid metabolism which are used are advantageously selected from the group consisting of acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferases, fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Genes selected from the group of the Δ4-desaturases, Δ5-desaturases, Δ6-desaturases, Δ8-desaturases, Δ9-desaturases, Δ12-desaturases, Δ15-desaturases, Δ12- and Δ15-desaturases, ω3-desaturases, Δ6-elongases, Δ9-elongases or Δ5-elongases in combination with the polynucleotides according to the invention are preferably used, it being possible to use individual genes or a plurality of genes in combination. For especially preferred gene combinations, reference is made here to tables 5 and 6, which are shown in the examples.

Advantageously, the desaturases used in the method according to the invention convert their respective substrates in the form of the CoA-fatty acid esters. If preceded by an elongation step, this advantageously results in an increased product yield. The respective desaturation products are thereby synthesized in greater quantities, since the elongation step is usually carried out with the CoA-fatty acid esters, while the desaturation step is predominantly carried out with the phospholipids or the triglycerides. Therefore, a substitution reaction between the CoA-fatty acid esters and the phospholipids or triglycerides, which would require a further, possibly limiting, enzyme reaction, is not necessary.

Owing to the enzymatic activity of the polypeptides used in the method according to the invention, a wide range of polyunsaturated fatty acids can be produced in the method according to the invention. Depending on the choice of the organisms, such as the advantageous plants, used for the method according to the invention, mixtures of the various polyunsaturated fatty acids or individual polyunsaturated fatty acids, such as EPA or ARA, can be produced in free or bound form. Depending on the prevailing fatty acid composition in the starting plant (C18:2- or C18:3-fatty acids), fatty acids which are derived from C18:2-fatty acids, such as GLA, DGLA or ARA, or fatty acids which are derived from C18:3-fatty acids, such as SDA, ETA or EPA, are thus obtained. If only linoleic acid (=LA, $C18:2^{\Delta 9,12}$) is present as unsaturated fatty acid in the plant used for the method, the method can only afford GLA, DGLA and ARA as products, all of which can be present as free fatty acids or in bound form. If only α-linolenic acid (=ALA, $C18:3^{\Delta 9,12,15}$) is present as unsaturated fatty acid in the plant used for the method, the method can only afford SDA, ETA, EPA and/or DHA as products, all of which can be present as free fatty acids or in bound form, as described above. Owing to the modification of the activity of the enzymes Δ5-desaturase, Δ6-desaturase, Δ4-desaturase, Δ12-desaturase, Δ15-desaturase, ω3-desaturase, Δ5-elongase and/or Δ6-elongase which play a role in the synthesis, it is possible to produce, in a targeted fashion, only individual products in the abovementioned organisms, advantageously in the abovementioned plants. Owing to the activity of Δ6-desaturase and Δ6-elongase, for example, GLA and DGLA, or SDA and ETA, are formed, depending on the starting plant and unsaturated fatty acid. DGLA or ETA or mixtures of these are preferably formed. If Δ5-desaturase, Δ5-elongase and Δ4-desaturase are additionally introduced into the organisms, advantageously into the plant, ARA, EPA and/or DHA are additionally formed. Advantageously, only ARA, EPA or DHA or mixtures of these are synthesized, depending on the fatty acids present in the organism, or in the plant, which acts as starting substance for the synthesis. Since biosynthetic cascades are involved, the end products in question are not present as pure substances in the organisms. Small amounts of the precursor compounds are always additionally present in the end product. These small amounts amount to less than 20% by weight, advantageously less than 15% by weight, especially advantageously less than 10% by weight, most advantageously less than 5, 4, 3, 2 or 1% by weight, based on the end product DGLA, ETA or their mixtures, or ARA, EPA, DHA or their mixtures, advantageously EPA or DHA or their mixtures.

In addition to the production, directly in the organism, of the starting fatty acids for the polypeptides used in the method of the invention, the fatty acids can also be fed externally. The production in the organism is preferred for reasons of economy. Preferred substrates are linoleic acid ($C18:2^{\Delta 9,12}$), γ-linolenic acid ($C18:3^{\Delta 6,9,12}$), eicosadienoic acid ($C20:2^{\Delta 11,14}$), dihomo-γ-linolenic acid ($C20:3^{\Delta 8,11,14}$), arachidonic acid ($C20:4^{\Delta5,8,11,14}$), docosatetraenoic acid ($C22:4^{\Delta7,10,13,16}$) and docosapentaenoic acid ($C22:5^{\Delta4,7,10,13,15}$).

To increase the yield in the described method for the production of oils and/or triglycerides with an advantageously elevated content of polyunsaturated fatty acids, it is advantageous to increase the amount of starting product for the synthesis of fatty acids; this can be achieved for example by introducing, into the organism, a nucleic acid which codes for a polypeptide with a Δ5-desaturase activity according to the invention. This is particularly advantageous in oil-producing organisms such as those from the family of the Brassicaceae, such as the genus *Brassica*, for example oilseed rape; the family of the Elaeagnaceae, such as the genus *Elaeagnus*, for example the genus and species *Olea europaea*, or the family Fabaceae, such as the genus *Glycine*, for example the genus and species *Glycine max*, which are high in oleic acid. Since these organisms are only low in linoleic acid (Mikoklajczak et al., Journal of the American Oil Chemical Society, 38, 1961, 678-681), the use of the Δ5-desaturases for producing the starting arachidonic acid, or eicosapentaenoic acid, or docosapentaenoic acid, or docosahexaenoic acid is advantageous.

The method according to the invention advantageously employs the abovementioned nucleic acid sequences or their derivatives or homologs which code for polypeptides which retain the enzymatic activity of the proteins encoded by nucleic acid sequences. These sequences, individually or in combination with the polynucleotides according to the invention, are cloned into expression constructs and used for the introduction into, and expression in, organisms. Owing to their construction, these expression constructs make possible an advantageous optimal synthesis of the polyunsaturated fatty acids produced in the method according to the invention.

In a preferred embodiment, the method furthermore comprises the step of obtaining a cell or an intact organism which comprises the nucleic acid sequences used in the method, where the cell and/or the organism is transformed with a polynucleotide according to the invention, a gene construct or a vector as described below, alone or in combination with further nucleic acid sequences which code for proteins of the fatty acid or lipid metabolism. In a further preferred embodiment, this method furthermore comprises the step of obtaining the oils, lipids or free fatty acids from the organism or from the culture. The culture can, for example, take the form of a fermentation culture, for example in the case of the cultivation of microorganisms, such as, for example, *Mortierella, Thalassiosira, Mantoniella, Ostreococcus, Saccharomyces* or *Thraustochytrium*, or a greenhouse- or field-grown culture of a plant. The cell or the organism thus produced is advantageously a cell of an oil-producing organism, such as an oil crop, such as, for example, peanut, oilseed rape, canola, linseed, hemp, soybean, safflower, sunflowers or borage.

In the case of plant cells, plant tissue or plant organs, "growing" is understood as meaning, for example, the cultivation on or in a nutrient medium, or of the intact plant on or in a substrate, for example in a hydroponic culture, potting compost or on arable land.

Suitable organisms or host cells for the method according to the invention are those which are capable of synthesizing fatty acids, specifically unsaturated fatty acids, and/or which are suitable for the expression of recombinant genes. Examples which may be mentioned are plants such as *Arabidopsis*, Asteraceae such as *Calendula* or crop plants such as soybean, peanut, castor-oil plant, sunflower, maize, cotton, flax, oilseed rape, coconut, oil palm, safflower (*Carthamus tinctorius*) or cacao bean, microorganisms, such as fungi, for example the genus *Mortierella, Thraustochytrium, Saprolegnia, Phytophthora* or *Pythium*, bacteria, such as the genus *Escherichia* or *Shewanella*, yeasts, such as the genus *Saccharomyces*, cyanobacteria, ciliates, algae such as *Mantoniella* or *Ostreococcus*, or protozoans such as dinoflagellates, such as *Thalassiosira* or *Crypthecodinium*. Preferred organisms are those which are naturally capable of synthesizing substantial amounts of oil, such as fungi, such as *Mortierella alpina, Pythium insidiosum, Phytophthora infestans*, or plants such as soybean, oilseed rape, coconut, oil palm, safflower, flax, hemp, castor-oil plant, *Calendula*, peanut, cacao bean or sunflower, or yeasts such as *Saccharomyces cerevisiae*, with soybean, flax, oilseed rape, safflower, sunflower, *Calendula, Mortierella* or *Saccharomyces cerevisiae* being especially preferred. In principle, suitable as host organisms are, in addition to the abovementioned transgenic organisms, also transgenic animals, advantageously nonhuman animals, for example *Caenorhabditis elegans*. Further suitable host cells and organisms have already been described extensively above.

Transgenic plants which comprise the polyunsaturated fatty acids synthesized in the method according to the invention can advantageously be marketed directly without there being any need for the oils, lipids or fatty acids synthesized to be isolated. Plants for the method according to the invention are listed as meaning intact plants and all plant parts, plant organs or plant parts such as leaf, stem, seeds, root, tubers, anthers, fibers, root hairs, stalks, embryos, calli, cotelydons, petioles, harvested material, plant tissue, reproductive tissue and cell cultures which are derived from the transgenic plant and/or can be used for bringing about the transgenic plant. In this context, the seed comprises all parts of the seed such as the seed coats, epidermal cells, seed cells, endosperm or embryonic tissue. However, the compounds produced in the method according to the invention can also be isolated from the organisms, advantageously plants, in the form of their oils, fats, lipids and/or free fatty acids. Polyunsaturated fatty acids produced by this method can be obtained by harvesting the organisms, either from the crop in which they grow, or from the field. This can be done via pressing or extraction of the plant parts, preferably of the plant seeds. In this context, the oils, fats, lipids and/or free fatty acids can be obtained by pressing by what is known as cold-beating or cold-pressing without applying heat. To allow for greater ease of disruption of the plant parts, specifically the seeds, they are previously comminuted, steamed or roasted. The seeds which have been pretreated in this manner can subsequently be pressed or extracted with solvent such as warm hexane. The solvent is subsequently removed. In the case of microorganisms, the latter are, after harvesting, for example extracted directly without further methoding steps or else, after disruption, extracted via various methods with which the skilled worker is familiar. In this manner, more than 96% of the compounds produced in the method can be isolated. Thereafter, the resulting products are methoded further, i.e. refined. In this method, for example the plant mucilages and suspended matter are first removed. What is known as desliming can be effected enzymatically or, for example, chemico-physically by addition of acid such as phosphoric acid. Thereafter, the free fatty acids are removed by treatment with a base, for example sodium hydroxide solution. The resulting product is washed thoroughly with water to remove the alkali remaining in the product and then dried. To remove the pigments remaining in the product, the products are subjected to bleaching, for example using fuller's earth or active charcoal. At the end, the product is deodorized, for example using steam.

The PUFAs or LCPUFAs produced by this method are preferably $C_{18}$-, $C_{20}$- or $C_{22}$-fatty acid molecules, advantageously $C_{20}$- or $C_{22}$-fatty acid molecules, with at least two double bonds in the fatty acid molecule, preferably three, four, five or six double bonds. These $C_{18}$-, $C_{20}$- or $C_{22}$-fatty acid molecules can be isolated from the organism in the form of an oil, a lipid or a free fatty acid. Suitable organisms are, for example, those mentioned above. Preferred organisms are transgenic plants.

One embodiment of the invention is therefore oils, lipids or fatty acids or fractions thereof which have been produced by the abovedescribed method, especially preferably oil, lipid or a fatty acid composition comprising PUFAs and being derived from transgenic plants.

As described above, these oils, lipids or fatty acids advantageously comprise 6 to 15% of palmitic acid, 1 to 6% of stearic acid, 7-85% of oleic acid, 0.5 to 8% of vaccenic acid, 0.1 to 1% of arachic acid, 7 to 25% of saturated fatty acids, 8 to 85% of monounsaturated fatty acids and 60 to 85% of polyunsaturated fatty acids, in each case based on 100% and on the total fatty acid content of the organisms. Advantageous polyunsaturated fatty acids which are present in the fatty acid esters or fatty acid mixtures are preferably at least 0.1, 0.2, 0.3, 0.4, 0.5, 0.6, 0.7, 0.8, 0.9 or 1% of arachidonic acid, based on the total fatty acid content. Moreover, the fatty acid esters or fatty acid mixtures which have been produced by the method of the invention advantageously comprise fatty acids selected from the group of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernolic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendulic acid (8t10t12c-octadecatrienoic acid), catalpic acid (9t11t13c-octadecatrienoic acid), eleostearic acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinoleic acid (12-hydroxyoleic acid) and/or coriolic acid (13-hydroxy-9c,11t-octadecadienoic acid). The abovementioned fatty acids are, as a rule, advantageously only found in traces in the fatty acid esters or fatty acid mixtures produced by the method according to the invention, that is to say that, based on the total fatty acids, they occur to less than 30%, preferably to less than 25%, 24%, 23%, 22% or 21%, especially preferably to less than 20%, 15%, 10%, 9%, 8%, 7%, 6% or 5%, very especially preferably to less than 4%, 3%, 2% or 1%. The fatty acid esters or fatty acid mixtures produced by the method according to the invention advantageously comprise less than 0.1%, based on the total fatty acids, or no butyric acid, no cholesterol, no clupanodonic acid (=docosapentaenoic acid, C22:5$^{\Delta 4,8,12,15,21}$) and no nisinic acid (tetracosahexaenoic acid, C23:6$^{\Delta 3,8,12,15,18,21}$).

The oils, lipids or fatty acids according to the invention preferably comprise at least 0.5%, 1%, 2%, 3%, 4% or 5%, advantageously at least 6%, 7%, 8%, 9% or 10%, especially advantageously at least 11%, 12%, 13%, 14% or 15% of ARA or at least 0.5%, 1%, 2%, 3%, 4% or 5%, advantageously at least 6% or 7%, especially advantageously at least 8%, 9% or 10% of EPA and/or DHA, based on the total fatty acid content of the production organism, advantageously of a plant, especially advantageously of an oil crop plant such as soybean, oilseed rape, coconut, oil palm, safflower, flax, hemp, castor-oil plant, *Calendula*, peanut, cacao bean, sunflower, or the abovementioned further mono- or dicotyledonous oil crop plants.

A further embodiment according to the invention is the use of the oil, lipid, the fatty acids and/or the fatty acid composition in feedstuffs, foodstuffs, cosmetics or pharmaceuticals. The oils, lipids, fatty acids or fatty acid mixtures according to the invention can be used in the manner with which the skilled worker is familiar for mixing with other oils, lipids, fatty acids or fatty acid mixtures of animal origin, such as, for example, fish oils. These oils, lipids, fatty acids or fatty acid mixtures, which are composed of vegetable and animal constituents, may also be used for the preparation of feedstuffs, foodstuffs, cosmetics or pharmaceuticals.

The term "oil", "lipid" or "fat" is understood as meaning a fatty acid mixture comprising unsaturated, saturated, preferably esterified, fatty acid(s). The oil, lipid or fat is preferably high in polyunsaturated free or, advantageously, esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The amount of unsaturated esterified fatty acids preferably amounts to approximately 30%, a content of 50% is more preferred, a content of 60%, 70%, 80% or more is even more preferred. For the analysis, the fatty acid content can, for example, be determined by gas chromatography after converting the fatty acids into the methyl esters by transesterification. The oil, lipid or fat can comprise various other saturated or unsaturated fatty acids, for example calendulic acid, palmitic acid, palmitoleic acid, stearic acid, oleic acid and the like. The content of the various fatty acids in the oil or fat can vary, in particular depending on the starting organism.

The polyunsaturated fatty acids with advantageously at least two double bonds which are produced in the method are, as described above, for example sphingolipids, phosphoglycerides, lipids, glycolipids, phospholipids, monoacylglycerol, diacylglycerol, triacylglycerol or other fatty acid esters.

Starting from the polyunsaturated fatty acids with advantageously at least five or six double bonds, which acids have been prepared in the method according to the invention, the polyunsaturated fatty acids which are present can be liberated for example via treatment with alkali, for example aqueous KOH or NaOH, or acid hydrolysis, advantageously in the presence of an alcohol such as methanol or ethanol, or via enzymatic cleavage, and isolated via, for example, phase separation and subsequent acidification via, for example, $H_2SO_4$. The fatty acids can also be liberated directly without the abovedescribed methoding step.

After their introduction into an organism, advantageously a plant cell or plant, the nucleic acids used in the method can either be present on a separate plasmid or, advantageously, integrated into the genome of the host cell. In the case of integration into the genome, integration can be random or else be effected by recombination such that the native gene is replaced by the copy introduced, whereby the production of the desired compound by the cell is modulated, or by the use of a gene in "trans", so that the gene is linked operably with a functional expression unit which comprises at least one sequence which ensures the expression of a gene and at least one sequence which ensures the polyadenylation of a functionally transcribed gene. The nucleic acids are advantageously introduced into the organisms via multi-expression cassettes or constructs for multiparallel expression, advantageously into the plants for the multiparallel seed-specific expression of genes.

Mosses and algae are the only known plant systems which produce substantial amounts of polyunsaturated fatty acids such as arachidonic acid (ARA) and/or eicosapentaenoic acid (EPA) and/or docosahexaenoic acid (DHA). Mosses comprise PUFAs in membrane lipids, while algae, organisms which are related to algae and a few fungi also accumulate substantial amounts of PUFAs in the triacylglycerol fraction. This is why nucleic acid molecules which are isolated from such strains that also accumulate PUFAs in the triacylglycerol fraction are particularly advantageous for the method according to the invention and thus for the modification of the lipid and PUFA production system in a host, in particular plants such as oil crops, for example oilseed rape, canola, linseed, hemp, soybeans, sunflowers and borage. They can therefore be used advantageously in the method according to the invention.

Substrates which are suitable for the polypeptides according to the invention of the fatty acid or lipid metabolism selected from the group acyl-CoA dehydrogenase(s), acyl-ACP [=acyl carrier protein] desaturase(s), acyl-ACP thioesterase(s), fatty acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenase(s), lipoxygenase(s), triacylglycerol lipase(s), allene oxide synthase(s), hydroperoxide lyase(s) or fatty acid elongase(s) are advantageously $C_{16}$-, $C_{18}$- or $C_{20}$-fatty acids. The fatty acids converted as substrates in the method are preferably converted in the form of their acyl-CoA esters and/or their phospholipid esters.

To produce the long-chain PUFAs according to the invention, the polyunsaturated $C_{18}$-fatty acids must first be desaturated by the enzymatic activity of a desaturase and subsequently be elongated by at least two carbon atoms via an elongase. After one elongation cycle, this enzyme activity gives $C_{20}$-fatty acids and after two elongation cycles, $C_{22}$-fatty acids. The activity of the desaturases and elongases used in the method according to the invention preferably leads to $C_{18}$-, $C_{20}$- and/or $C_{22}$-fatty acids, advantageously with at least two double bonds in the fatty acid molecule, preferably with three, four, five or six double bonds, especially preferably to give $C_{20}$- and/or $C_{22}$-fatty acids with at least two double bonds in the fatty acid molecule, preferably with three, four, five or six double bonds, very especially preferably with five or six double bonds in the molecule. After a first desaturation and the elongation have taken place, further desaturation and elongation steps such as, for example, such a desaturation in the 45 and 44 positions may take place. Products of the method according to the invention which are especially preferred are dihomo-γ-linolenic acid, arachidonic acid, eicosapentaenoic acid, docosapentaenoic acid and/or docosahexaenoic acid. The $C_{20}$-fatty acids with at least two double bonds in the fatty acid can be desaturated by the enzymatic activity according to the invention in the form of the free fatty acid or in the form of the esters, such as phospholipids, glycolipids, sphingolipids, phosphoglycerides, monoacylglycerol, diacylglycerol or triacylglycerol.

The preferred biosynthesis site of fatty acids, oils, lipids or fats in the plants which are advantageously used is, for example, in general the seed or cell strata of the seed, so that seed-specific expression of the nucleic acids used in the method is sensible. However, it is obvious that the biosynthesis of fatty acids, oils or lipids need not be limited to the seed tissue, but can also take place in a tissue-specific manner in all the other parts of the plant—for example in epidermal cells or in the tubers.

If microorganism such as yeasts, such as *Saccharomyces* or *Schizosaccharomyces*, fungi such as *Mortierella, Aspergillus, Phytophthora, Entomophthora, Mucor* or *Thraustochytrium*, algae such as *Isochrysis, Mantoniella, Ostreococcus, Phaeodactylum* or *Crypthecodinium* are used as organisms in the method according to the invention, these organisms are advantageously grown in fermentation cultures.

Owing to the use of the nucleic acids according to the invention which code for a desaturase, the polyunsaturated fatty acids produced in the method can be increased by at least 5%, preferably by at least 10%, especially preferably by at least 20%, very especially preferably by at least 50% in comparison with the wild type of the organisms which do not comprise the nucleic acids recombinantly.

In principle, the polyunsaturated fatty acids produced by the method according to the invention in the organisms used in the method can be increased in two different ways. Advantageously, the pool of free polyunsaturated fatty acids and/or the content of the esterified polyunsaturated fatty acids produced via the method can be enlarged. Advantageously, the pool of esterified polyunsaturated fatty acids in the transgenic organisms is enlarged by the method according to the invention.

If microorganisms are used as organisms in the method according to the invention, they are grown or cultured in a manner with which the skilled worker is familiar, depending on the host organism. As a rule, microorganisms are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while introducing oxygen gas. The pH of the nutrient liquid can either be kept constant, that is to say regulated during the culturing period, or not. The cultures can be grown batchwise, semi-batchwise or continuously. Nutrients can be provided at the beginning of the fermentation or fed in semicontinuously or continuously. The polyunsaturated fatty acids produced can be isolated from the organisms as described above by methods known to the skilled worker, for example by extraction, distillation, crystallization, if appropriate precipitation with salt, and/or chromatography. To this end, the organisms can advantageously be disrupted beforehand.

If the host organisms are microorganisms, the methods according to the invention is advantageously carried out at a temperature of between 0° C. and 95° C., preferably between 10° C. and 85° C., especially preferably between 15° C. and 75° C., very especially preferably between 15° C. and 45° C.

In this method, the pH value is advantageously kept between pH 4 and 12, preferably between pH 6 and 9, especially preferably between pH 7 and 8.

The method according to the invention can be operated batchwise, semibatchwise or continuously. An overview over known cultivation methods can be found in the textbook by Chmiel (Bioprozeβtechnik 1. Einführung in die Bioverfahrenstechnik [Biomethod technology 1. Introduction to biomethod technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the strains in question. Descriptions of culture media for various microorganisms can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of very good carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar raffination. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for cultivating microorganisms usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds depends heavily on the particular experiment and is decided upon individually for each specific case. Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air, into the culture. The temperature of the culture is normally 20° C. to 45° C. and preferably 25° C. to 40° C. The culture is continued until formation of the desired product is at a maximum. This aim is normally achieved within 10 hours to 160 hours.

The fermentation broths obtained in this way, in particular those containing polyunsaturated fatty acids, usually contain a dry mass of from 7.5 to 25% by weight.

The fermentation broth can then be methoded further. The biomass may, according to requirement, be removed completely or partially from the fermentation broth by separation methods such as, for example, centrifugation, filtration, decanting or a combination of these methods or be left completely in said broth. It is advantageous to method the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be methoded to obtain the fatty acids present therein.

The polynucleotides or polypeptides of the present invention which are involved in the metabolism of lipids and fatty acids, PUFA cofactors and enzymes or in the transport of lipophilic compounds across membranes are used in the method according to the invention for the modulation of the production of PUFAs in transgenic organisms, advantageously in plants, such as maize, wheat, rye, oats, triticale, rice, barley, soybean, peanut, cotton, *Linum* species such as linseed or flax, *Brassica* species such as oilseed rape, canola and turnip rape, pepper, sunflower, borage, evening primrose and Tagetes, Solanaceae plants such as potato, tobacco, eggplant and tomato, *Vicia* species, pea, cassava, alfalfa, bushy plants (coffee, cacao, tea), *Salix* species, trees (oil palm, coconut) and perennial grasses and fodder crops, either directly (for example when the overexpression or optimization of a fatty acid biosynthesis protein has a direct effect on the yield, production and/or production efficiency of the fatty acid from modified organisms) and/or can have an indirect effect which nevertheless leads to an enhanced yield, production and/or production efficiency of the PUFAs or a reduction of undesired compounds (for example when the modulation of the metabolism of lipids and fatty acids, cofactors and enzymes leads to modifications of the yield, production and/or production efficiency or the composition of the desired compounds within the cells, which, in turn, can affect the production of one or more fatty acids).

The combination of various precursor molecules and biosynthesis enzymes leads to the production of various fatty acid molecules, which has a decisive effect on lipid composition, since polyunsaturated fatty acids (=PUFAs) are not only incorporated into triacylglycerol but also into membrane lipids.

Brassicaceae, Boraginaceae, Primulaceae, or Linaceae are particularly suitable for the production of PUFAs, for example stearidonic acid, eicosapentaenoic acid and docosahexaenoic acid. Linseed (*Linum usitatissimum*) is especially advantageously suitable for the production of PUFAs with the nucleic acid sequences according to the invention, advantageously, as described, in combination with further desaturases and elongases.

Lipid synthesis can be divided into two sections: the synthesis of fatty acids and their binding to sn-glycerol-3-phosphate, and the addition or modification of a polar head group. Usual lipids which are used in membranes comprise phospholipids, glycolipids, sphingolipids and phosphoglycerides. Fatty acid synthesis starts with the conversion of acetyl-CoA into malonyl-CoA by acetyl-CoA carboxylase or into acetyl-ACP by acetyl transacylase. After a condensation reaction, these two product molecules together form acetoacetyl-ACP, which is converted via a series of condensation, reduction and dehydratation reactions so that a saturated fatty acid molecule with the desired chain length is obtained. The production of the unsaturated fatty acids from these molecules is catalyzed by specific desaturases, either aerobically by means of molecular oxygen or anaerobically (regarding the fatty acid synthesis in microorganisms, see F. C. Neidhardt et al. (1996) *E. coli* and *Salmonella*. ASM Press: Washington, D.C., pp. 612-636 and references cited therein; Lengeler et al. (Ed.) (1999) Biology of Procaryotes. Thieme: Stuttgart, N.Y., and the references therein, and Magnuson, K., et al. (1993) Microbiological Reviews 57:522-542 and the references therein). To undergo the further elongation steps, the resulting phospholipid-bound fatty acids must be returned to the fatty acid CoA ester pool from the phospholipids. This is made possible by acyl-CoA: lysophospholipid acyltransferases. Moreover, these enzymes are capable of transferring the elongated fatty acids from the CoA esters back to the phospholipids. If appropriate, this reaction sequence can be traversed repeatedly.

Examples of precursors for the biosynthesis of PUFAs are oleic acid, linoleic acid and linolenic acid. These $C_{18}$-carbon fatty acids must be elongated to $C_{20}$ and $C_{22}$ in order to obtain fatty acids of the eicosa and docosa chain type. With the aid of the desaturases used in the method, such as the Δ12-, Δ15-, Δ12- and Δ15-, ω3-, Δ4-, Δ5- and Δ6-desaturases and/or the Δ5-, Δ6-elongases, arachidonic acid, eicosapentaenoic acid, docosapentaenoic acid or docosahexaenoic acid, advantageously eicosapentaenoic acid and/or docosahexaenoic acid, can be produced and subsequently employed in various applications regarding foodstuffs, feedstuffs, cosmetics or pharmaceuticals. $C_{20}$- and/or $C_{22}$-fatty acids with at least two, advantageously at least three, four, five or six, double bonds in the fatty acid molecule, preferably $C_{20}$- or $C_{22}$-fatty acids with advantageously four, five or six double bonds in the fatty acid molecule, can be prepared using the abovementioned enzymes. Desaturation may take place before or after elongation of the fatty acid in question. This is why the products of the desaturase activities and of the further desaturation and elongation steps which are possible result in preferred PUFAs with a higher degree of desaturation, including a further elongation from $C_{20}$- to $C_{22}$-fatty acids, to fatty acids such as γ-linolenic acid, dihomo-γ-linolenic acid, arachidonic acid, stearidonic acid, eicosatetraenoic acid or eicosapentaenoic acid. Substrates of the desaturases and elongases used in the method according to the invention are $C_{16}$-, $C_{18}$- or $C_{20}$-fatty acids such as, for example, linoleic acid, γ-linolenic acid, α-linolenic acid, dihomo-γ-linolenic acid, eicosatetraenoic acid or stearidonic acid. Preferred substrates are linoleic acid, γ-linolenic acid and/or α-linolenic acid, dihomo-γ-linolenic acid or arachidonic acid, eicosatetraenoic acid or eicosapentaenoic acid. The synthesized $C_{20}$- or $C_{22}$-fatty acids with at least two, three, four, five or six double bonds in the fatty acid are obtained in the method according to the invention in the form of the free fatty acid or in the form of their esters, for example in the form of their glycerides.

The term "glyceride" is understood as meaning a glycerol esterified with one, two or three carboxyl radicals (mono-, di- or triglyceride). "Glyceride" is also understood as meaning a mixture of various glycerides. The glyceride or glyceride mixture may comprise further additions, for example free fatty acids, antioxidants, proteins, carbohydrates, vitamins and/or other substances.

For the purposes of the method according to invention, a "glyceride" is furthermore understood as meaning glycerol derivatives. In addition to the abovedescribed fatty acid glycerides, these also include glycerophospholipids and glyceroglycolipids. Preferred examples which may be mentioned in this context are the glycerophospholipids such as lecithin (phosphatidylcholine), cardiolipin, phosphatidylglycerol, phosphatidylserine and alkylacylglycerophospholipids.

Furthermore, fatty acids must subsequently be translocated to various modification sites and incorporated into the triacylglycerol storage lipid. A further important step in lipid synthesis is the transfer of fatty acids to the polar head groups, for example by glycerol fatty acid acyltransferase (see Frentzen, 1998, Lipid, 100(4-5):161-166).

Publications on plant fatty acid biosynthesis and on the desaturation, the lipid metabolism and the membrane transport of lipidic compounds, on beta-oxidation, fatty acid modification and cofactors, triacylglycerol storage and triacylglycerol assembly, including the references therein, see the following papers: Kinney, 1997, Genetic Engineering, Ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engineering, Ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, Ed.: Murata and Somerville, Rockville, American Society of Plant Physiologists, 150-158, Murphy & Ross 1998, Plant Journal. 13(1):1-16.

The PUFAs produced in the method comprise a group of molecules which higher animals are no longer capable of synthesizing and must therefore take up, or which higher animals are no longer capable of synthesizing themselves in sufficient quantities and must therefore take up additional quantities, although they can be synthesized readily by other organisms such as bacteria; for example, cats are no longer capable of synthesizing arachidonic acid.

Phospholipids for the purposes of the invention are understood as meaning phosphatidylcholine, phosphatidylethanolamine, phosphatidylserine, phosphatidylglycerol and/or phosphatidylinositol, advantageously phosphatidylcholine. The terms "production or productivity" are known in the art and encompasses the concentration of the fermentation product (compounds of the formula I) which is formed within a specific period of time and in a specific fermentation volume (for example kg of product per hour per liter). It also comprises the productivity within a plant cell or a plant, that is to say the content of the desired fatty acids produced in the method relative to the content of all fatty acids in this cell or plant. The term "production efficiency" comprises the time required for obtaining a specific production quantity (for example the time required by the cell to establish a certain throughput rate of a fine chemical). The term "yield or product/carbon yield" is known in the art and comprises the efficiency of the conversion of the carbon source into the product (i.e. the fine chemical). This is usually expressed for example as kg of product per kg of carbon source. By increasing the yield or production of the compound, the amount of the molecules obtained of this compound, or of the suitable molecules of this compound obtained, in a specific culture quantity over a specified period of time is increased. The terms "biosynthesis or biosynthetic pathway" are known in the art and comprise the synthesis of a compound, preferably an organic compound, by a cell from intermediates, for example in a multi-step and strongly regulated method. The terms "catabolism or catabolic pathway" are known in the art and comprise the cleavage of a compound, preferably of an organic compound, by a cell to give catabolites (in more general terms, smaller or less complex molecules), for example in a multi-step and strongly regulated method. The term "metabolism" is known in the art and comprises the totality of the biochemical reactions which take place in an organism. The metabolism of a certain compound (for example the metabolism of a fatty acid) thus comprises the totality of the biosynthetic pathways, modification pathways and catabolic pathways of this compound in the cell which relate to this compound.

By employing, in the method according to the invention, the polynucleotides according to the invention and optionally further polynucleotides which code for enzymes of the lipid or fatty acid metabolism it is possible to achieve various advantageous effects. Thus, it is possible to influence the yield, production and/or production efficiency of the polyunsaturated fatty acids in a plant, preferably in an oil crop plant, or in a microorganism. The number or activity of the polypeptides or polynucleotides according to the invention can be increased, so that larger amounts of the gene products and, ultimately, larger amounts of the compounds of the general formula I are produced. A de novo synthesis in an organism, which, before the gene(s) in question was/were introduced, had been lacking the activity and ability to biosynthesize the compounds, is also possible. The same applies analogously to the combination with further desaturases or elongases or further enzymes of the fatty acid and lipid metabolism. The use of a variety of divergent sequences, i.e. sequences which differ at the DNA sequence level, may also be advantageous in this context, or else the use of gene expression promoters which makes possible a different gene expression as far as timing is concerned, for example as a function of the degree of maturity of a seed or oil-storing tissue.

By introducing, into an organism, a polynucleotide according to the invention alone or in combination with other genes into a cell it is possible not only to increase the biosynthetic flow towards the end product, but also to increase, or to create de novo, the corresponding triacylglycerol composition. Equally, the number or activity of other genes which are required for the import of nutrients for the biosynthesis of one or more fatty acids, oils, polar and/or neutral lipids can be increased, so that the concentration of these precursors, cofactors or intermediates within the cells or within the storage compartment is increased, whereby the ability of the cells to produce PUFAs is further enhanced. By optimizing the activity, or increasing the number, of one or more polynucleotides or polypeptides according to the invention which are involved in the biosynthesis of these compounds, or by destroying the activity of one or more genes which are involved in the degradation of these compounds, it may be possible to increase the yield, production and/or production efficiency of fatty acid and lipid molecules from organisms, in particular from plants. The fatty acids obtained in the method are suitable as starting materials for the chemical synthesis of further products of interest. For example, they can be used for the preparation of pharmaceuticals, foodstuffs, animal feeds or cosmetics, either alone or in combination with one another.

It can be seen from what has been said above that the invention also relates to a method for the preparation of an oil, lipid or fatty acid composition, comprising the steps of the method according to the invention and the further step of formulating the substance as an oil, lipid or fatty acid composition.

In a preferred embodiment of this method, the oil, lipid or fatty acid composition is formulated further to give a drug, a cosmetic product, a foodstuff, a feedstuff, preferably fish food, or a food supplement.

Finally, the invention relates to the principle of using the polynucleotide, the vector, the host cell, the polypeptide or the transgenic, nonhuman organism of the present invention for the production of an oil, lipid or fatty acid composition. The latter is then preferably to be employed as drug, cosmetic product, foodstuff, feedstuff, preferably fish food, or food supplement.

The content of all the references, patent applications, patents and published patent applications cited in the present patent application is hereby incorporated by reference to the respective specific disclosure.

FIGURES

FIG. 1: Sequence alignment of the *O. tauri* Δ6-desaturase (SEQ ID NO: 4) with the sequence from *Emiliana huxleyi* (SEQ ID NO: 2).

FIG. 2: Gas-chromatographic analysis of the feeding of yeasts transformed with pYES2.1/V5-His-TOPO (A) and pYES-SEQ1(Eh) (B). The substance fed was the fatty acid 20:3Δ8,11,14 (C). The Δ5-activity is demonstrated by the appearance of an additional peak with the identity 20:4Δ5,8,11,14 (D).

FIG. 3: Plasmid map of the binary construct LJB1589, transformed into *Brassica napus*, for the EPA synthesis in seeds.

Figure 4:
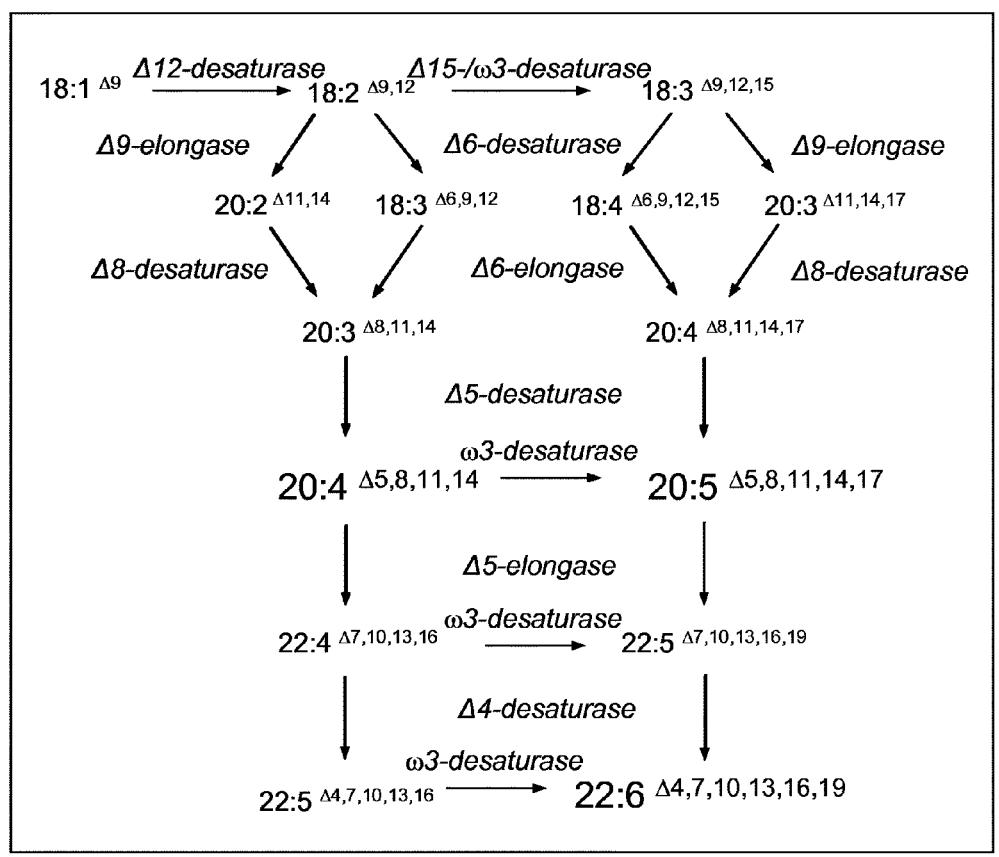

FIG. 4: Synthetic pathways for PUFAs.

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, bacterial cultures and the sequence analysis of recombinant DNA were carried out as described by Sambrook et al. (1989) (Cold Spring Harbor Laboratory Press: ISBN 0-87969-309-6).

Example 2

Sequence Analysis of Recombinant DNA

Recombinant DNA molecules were sequenced with an ABI laser fluorescence DNA sequencer by the method of Sanger (Sanger et al. (1977) Proc. Natl. Acad. Sci. USA 74, 5463-5467). Fragments obtained by polymerase chain reaction were sequenced and verified to avoid polymerase errors in constructs to be expressed.

Example 3

Lipid Extraction from Yeasts and Plants

The effect of the genetic modification in plants, fungi, algae, ciliates or on the production of a desired compound (such as a fatty acid) can be determined by growing the modified microorganisms or the modified plant under suitable conditions (such as those described above) and analyzing the medium and/or the cellular components for the elevated production of the desired product (i.e. of lipids or a fatty acid). These analytical techniques are known to the skilled worker and comprise spectroscopy, thin-layer chromatography, various types of staining methods, enzymatic and microbiological methods and analytical chromatography such as high-performance liquid chromatography (see, for example, Ullman, Encyclopedia of Industrial Chemistry, Vol. A2, p. 89-90 and p. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", p. 469-714, VCH: Weinheim; Belter, P. A., et al. (1988) Bioseparations: downstream methoding for Biotechnology, John Wiley and Sons; Kennedy, J. F., and Cabral, J. M. S. (1992) Recovery methods for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, p. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940 and Browse et al. (1986) Analytic Biochemistry 152:141-145. The qualitative and quantitative analysis of lipids or fatty acids is described in Christie, William W., Advances in Lipid Methodology, Ayr/Scotland: Oily Press (Oily Press Lipid Library; 2); Christie, William W., Gas Chromatography and Lipids. A Practical Guide Ayr, Scotland: Oily Press, 1989, Repr. 1992, IX, 307 pp. (Oily Press Lipid Library; 1); "Progress in Lipid Research", Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for the production of the desired compound, such as intermediates and by-products, in order to determine the overall production efficiency of the compound. The analytical methods comprise measuring the amount of nutrients in the medium (for example sugars, hydrocarbons, nitrogen sources, phosphate and other ions), measuring the biomass composition and the growth, analyzing the production of conventional metabolites of biosynthetic pathways and measuring gases which are generated during the fermentation. Standard methods for these measurements are described in Applied Microbial Physiology; A Practical Approach, P. M. Rhodes and P. F. Stanbury, Ed., IRL Press, p. 103-129; 131-163 and 165-192 (ISBN: 0199635773) and references cited therein.

One example is the analysis of fatty acids (abbreviations: FAME, fatty acid methyl ester; GC-MS, gas liquid chromatography/mass spectrometry; TAG, triacylglycerol; TLC, thin-layer chromatography).

Unambiguous proof for the presence of fatty acid products can be obtained by analyzing recombinant organisms using standard analytical methods: GC, GC-MS or TLC, as described on several occasions by Christie and the references therein (1997, in: Advances on Lipid Methodology, Fourth Edition: Christie, Oily Press, Dundee, 119-169; 1998, Gaschromatographie-Massenspektrometrie-Verfahren [Gas chromatography/mass spectrometry methods], Lipide 33:343-353).

The material to be analyzed can be disrupted by sonication, grinding in a glass mill, liquid nitrogen and grinding or via other applicable methods. After disruption, the material must be centrifuged. The sediment is resuspended in distilled water, heated for 10 minutes at 100° C., cooled on ice and recentrifuged, followed by extraction for one hour at 90° C. in 0.5 M sulfuric acid in methanol with 2% dimethoxypropane, which leads to hydrolyzed oil and lipid compounds, which give transmethylated lipids. These fatty acid methyl esters are extracted in petroleum ether and finally subjected to a GC analysis using a capillary column (Chrompack, WCOT Fused Silica, CP-Wax-52 CB, 25 microM, 0.32 mm) at a temperature gradient of between 170° C. and 240° C. for 20 minutes and 5 minutes at 240° C. The identity of the resulting fatty acid methyl esters must be defined using standards which are available from commercial sources (i.e. Sigma).

Example 4

Cloning a Desaturase Gene from the Alga *Emiliana huxleyi*

A sequence database of *Emiliana huxleyi* was searched using the known sequence of the *Ostreococcus tauri* Δ6-desaturase (Domergue et al. (2005) Biochem J. 389(Pt 2):483-90, SEQ ID NO: 3). It was possible to identify a sequence with homology to the amino acid sequence of the *Ostreococcus tauri* Δ6-desaturase (SEQ ID NO: 4). The sequence was elongated in the 5' and 3' direction by means of RACE-PCR (Clontech, USA) following the manufacturer's instructions (SEQ ID NO: 1), and the coding amino acid sequence (SEQ ID NO: 2) checked with the amino acid sequence of the *Ostreococcus tauri* Δ6-desaturase (SEQ ID NO: 4) in a sequence alignment (FIG. 1). According to ClustalW, the sequence alignment gives a sequence identity of 41%. Other amino acid sequences such as, for example, the Mortierella alpina d5-desaturase (WO2000/012720) show 22% identity.

To characterize the functions of SEQ ID NO: 1 and of the corresponding amino acid sequence, the open reading frame of the DNA was cloned downstream of the galactose-inducible GAL1 promoter of pYES2.1/V5-His-TOPO (Invitrogen), giving rise to the plasmid pYES-SEQ1(Eh). This plasmid was then transformed into the yeast strain INVSC-1 (Invitrogen) following the manufacturer's instructions and selected on plates with DOB-U agar on the basis of uracil auxotrophism. Positive colonies were identified by PCR. To this end, in each case 1 µl of defrosted cells, 200 µM dNTPs, 2.5 U Taq polymerase and 100 µmol of each primer were used to carry out in a total volume of 50 µl. The PCR conditions are as follows: first denaturation at 95° C. for 5 minutes, followed by 30 cycles of 30 seconds at 94° C., 1 minute at 55° C. and 2 minutes at 72° C., and a last elongation step for 10 minutes at 72° C. In parallel, the empty vector pYES2.1/V5-His-TOPO was transformed in the abovedescribed manner into competent yeast cells of the strain INVSC-1. Yeast cells with the plasmids pYES-SEQ1(Eh) were incubated for 12 h in liquid DOB-U medium at 28° C., 200 rpm, and then for a further 12 h in induction medium (DOB-U+2% (w/v) galactose+2% (w/v) raffinose) and 250 μM of fatty acids added to the medium. The specificity and activity of the gene to be characterized can be determined with reference to the added fatty acids.

Yeasts which have been transformed with the plasmids pYES2/V5-His-TOPO or pYES-SEQ1(Eh) were analyzed as follows:

The yeast cells from the main cultures were harvested by centrifugation (100×g, 5 min, 20° C.) and washed with 100 mM NaHCO$_3$, pH 8.0 to remove residual medium and fatty acids. Starting with the yeast cell sediments, fatty acid methyl esters (FAMEs) were prepared by acid methanolysis. To this end, the cell sediments were incubated for one hour at 80° C. together with 2 ml of 1 N methanolic sulfuric acid and 2% (v/v) of dimethoxypropane. The FAMEs were extracted twice with petroleum ether (PE). To remove nonderivatized fatty acids, the organic phases were washed in each case once with 2 ml of 100 mM NaHCO$_3$, pH 8.0 and 2 ml of distilled water. Thereafter, the PE phases were dried with Na$_2$SO$_4$, evaporated under argon and taken up in 100 μl of PE. The samples were separated on a DB-23 capillary column (30 m, 0.25 mm, 0.25 μm, Agilent) in a Hewlett-Packard 6850 gas chromatograph equipped with flame ionization detector. The conditions for the GLC analysis were as follows: the oven temperature was programmed from 50° C. to 250° C. with an increment of 5° C./min and finally 10 min at 250° C. (holding).

The signals are identified by comparing the retention times with corresponding fatty acid standards (Sigma). The methodology is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Activity and Substrate Determination of the Desaturases Identified

The substrate specificity of SEQ ID NO: 1 was determined after expression and feeding of various fatty acids. Surprisingly, only 20:3Δ8,11,14 and 20:4Δ8,11,14,17 of the fed substrates were converted. Thus, the coding sequence SEQ ID NO: 1 has 45-desaturase activity and is hereinbelow referred to as d5Des(Eh). The specific conversion of the fatty acids fed is shown in FIG. 2. After 48 h, 65-70% of the fed fatty acid is converted into the product, the conversion rate being calculated using the following formula:

Conversion rate in %=[product quantity/substrate quantity+product quantity]*100

The percentage of the converted fatty acid in the total fatty acids is 7-8%. The converted fatty acid is distributed to in each case 9% to the lipids phosphatidylethanolamine, phosphatidylinositol and phosphatidylserine. The lipid phosphatidylcholin only accounts for 2%. The remaining fatty acids are found in the neutral lipids. The fact that only little of the product of the d5Des(Eh) is accumulated in phosphatidylcholine, in combination with the distribution to a multiplicity of further lipid classes, shows the coenzyme A specificity of d5Des(Eh).

Example 7

Production of Transgenic Plants for the Production of Long-Chain Polyunsaturated Fatty Acids To produce long-chain polyunsaturated fatty acids in plants, various genes of the metabolic pathway are combined on a binary vector. To produce the fatty acid arachidonic acid (20:4Δ5,8,11,14), genes as described in table 1 were combined. Analogously, genes as described in Table 2 were combined for the production of the fatty acid eicosapentaenoic acid (20:5Δ5,8,11,14,17). Analogously, the genes as described in Table 3 were combined for producing the fatty acid docosahexaenoic acid (22:6Δ4,7,10,13,16,19).

TABLE 1

Gene combination for the production of arachidonic acid

| Genes | Activity | SEQ ID NO |
|---|---|---|
| D6Des(Pir) | Δ6-desaturase | 5 |
| D6Elo(Pp) | Δ6-elongase | 7 |
| D5Des(Eh) | Δ5-desaturase | 1 |
| D12Des(Ps) | Δ12-desaturase | 9 |

TABLE 2

Gene combination for the production of eicosapentaenoic acid

| Genes | Activity | SEQ ID NO |
|---|---|---|
| D6Des(Pir) | Δ6-desaturase | 5 |
| D6Elo(Pp) | Δ6-elongase | 7 |
| D5Des(Eh) | Δ5-desaturase | 1 |
| ω3-Des(Pi) | omega 3-desaturase | 11 |
| D12Des(Ps) | Δ12-desaturase | 9 |
| D15Des(Perf) | Δ15-desaturase | 13 |

TABLE 3

Gene combination for the production of docosahexaenoic acid

| Genes | Activity | SEQ ID NO |
|---|---|---|
| D6Des(Pir) | Δ6-desaturase | 5 |
| D6Elo(Pp) | Δ6-elongase | 7 |
| D5Des(Eh) | Δ5-desaturase | 1 |
| ω3-Des(Pi) | omega 3-desaturase | 11 |
| D12Des(Ps) | Δ12-desaturase | 9 |
| D15Des(Perf) | Δ15-desaturase | 13 |
| D5Elo(Ot) | Δ5-elongase | 15 |
| D4Des(Tc) | Δ4-desaturase | 17 |

Further transformation vectors based on pSUN-USP were generated for the transformation of plants. To this end, NotI cleavage sites were introduced at the 5' and at the 3' end of the coding sequence, using the following primer pairs (see Table 7).

Composition of the PCR Mix (50 μl):
5.00 μl template cDNA
5.00 μl 10× buffer (Advantage polymerase)+25 mM MgCl$_2$
5.00 μl 2 mM dNTP
1.25 μl of each primer (10 μmol/μL)
0.50 μl Advantage polymerase
The Advantage polymerase from Clontech is employed.
PCR Reaction Conditions:
Annealing temperature: 1 min 55° C.
Denaturation temperature: 1 min 94° C.
Elongation temperature: 2 min 72° C.
Number of cycles: 35

TABLE 7

Primer sequences (for cloning transformation vectors based on pSUN-USP)

| Gene | Primer | | SEQ ID NO |
|---|---|---|---|
| D6-Des(Pir) | Fwd: | gcggccgcgccatggtggacctcaagcctgg | 18 |
| | Rvs: | gcggccgttacatcgctgggaactcgg | 19 |
| D5-Des(Eh) | Fwd: | gcggccgcgccatgtcattggctgctaaagatg | 20 |
| | Rvs: | gcggccgtcaatgacctgtaactctaac | 21 |
| O3-Des(Pi) | Fwd: | gcggccgcgccatggcgacgaaggaggcgta | 22 |
| | Rvs: | gcggccgcgttacgtggacttggtcttggcc | 23 |
| D6-Elo(Pp) | Fwd: | gcggccgcgccatggaggtcgtggagagattc | 24 |
| | Rvs: | gcggccgcgtcactcagttttagctccc | 25 |
| D12Des(Ps) | Fwd: | gcggccgccatggcgatcctgaacccggag | 26 |
| | Rvs: | gcggccgcttagagcttgttcttgtagaag | 27 |
| D15Des (Perf) | Fwd: | gcggccgccatggccgtttcttccggtgc | 28 |
| | Rvs: | gcggccgcctaaatcttttggaaggaaag | 29 |
| D5Elo(Ot) | Fwd: | gcggccgcgccatgagcgcctccggtgcgctg | 30 |
| | Rvs: | gcggccgcgttagtcaatttttc | 31 |
| D4Des(Tc) | Fwd: | gcggccgcgccatgacggtcggctacgacgag | 32 |
| | Rvs: | gcggccgcgtcaggcagcgcgctgccagg | 33 |

The PCR products were incubated with the restriction enzyme NotI for 4 h at 37° C. The plant expression vector pSUN300-USP is incubated in the same manner. Thereafter, the PCR products and the 7624 bp vector are separated by agarose gel electrophoresis, and the corresponding DNA fragments are excised. The DNA is purified by means of the Qiagen gel purification kit, following the manufacturer's instructions. Thereafter, vector and PCR products are ligated. The Rapid Ligation kit from Roche is used for this purpose. The plasmids generated are verified by sequencing.

pSUN300 is a derivative of the plasmid pPZP (Hajdukiewicz, P, Svab, Z, Maliga, P., (1994) The small versatile pPZP family of Agrobacterium binary vectors for plant transformation. Plant Mol Biol 25:989-994). pSUN-USP originated from pSUN300, by inserting a USP promoter into pSUN300 in the form of an EcoRI fragment. The polyadenylation signal is the OCS gene from the A. tumefaciens Ti plasmid (ocsTerminator, Genbank Accession V00088) (De Greve, H., Dhaese, P., Seurinck, J., Lemmers, M., Van Montagu, M. and Schell, J. Nucleotide sequence and transcript map of the Agrobacterium tumefaciens Ti plasmid-encoded octopine synthase gene J. Mol. Appl. Genet. 1 (6), 499-511 (1982). The USP promoter corresponds to nucleotides 1 to 684 (Genbank Accession X56240), where part of the noncoding region of the USP gene is present in the promoter. The promoter fragment which is 684 base pairs in size was amplified by a PCR reaction using standard methods with the aid of a synthesized primer and by means of a commercially available T7 standard primer (Stratagene).
(Primer Sequence:

(Primer sequence:
[SEQ ID NO. 82]
5'-GTCGACCCGCGGACTAGTGGGCCCTCTAGACCCGGGGATCC

GGATCTGCTGGCTATGAA-3').

The PCR fragment was recut with EcoRI/SalI and inserted into the vector pSUN300 with OCS terminator. This gave rise to the plasmid named pSUN-USP, which can be employed for transforming plants by means of Agrobacterium tumefaciens.

a) Generation of transgenic oilseed rape plants (modified method of Moloney et al., 1992, Plant Cell Reports, 8:238-242)

To generate transgenic oilseed rape plants, binary vectors such as the pSUN plasmids described hereinabove or, by way of example, the derivative LJB1589 (SEQ ID No. 34, plasmid map in FIG. 3) with the relevant gene combinations were transformed into Agrobacterium tumefaciens C58C1: SHA001 (Deblaere et al, 1984, Nucl. Acids. Res. 13, 4777-4788). A 1:50 dilution of an overnight culture of a positively transformed agrobacterial colony in Murashige-Skoog medium (Murashige and Skoog 1962 Physiol. Plant. 15, 473) supplemented with 3% sucrose (3MS medium) was used for transforming oilseed rape plants (cv. Kumily, Swalof Weibul, Sweden). Petioles or hypocotyls of freshly germinated sterile oilseed rape plants (in each case approx. 1 cm²) were incubated with a 1:50 agrobacterial dilution for 5-10 minutes in a Petri dish. This was followed by 3 days of coincubation in the dark at 25° C. on 3MS medium supplemented with 0.8% Bacto agar. After 3 days, the cultivation was continued with 16 hours light/8 hours dark and was continued, in a 1-week rhythm, on MS medium supplemented with 500 mg/l Claforan (cefotaxim-sodium), 50 mg/l Kanamycin, 20 microM benzylaminopurine (BAP) and 1.6 g/l glucose. Growing shoots were transferred to MS medium supplemented with 2% sucrose, 250 mg/l Claforan and 0.8% Bacto agar. If no roots had formed after three weeks, the growth hormone 2-indolebutyric acid was added to the medium to promote rooting.

Regenerated shoots were obtained on 2MS medium supplemented with kanamycin and Claforan, transferred into soil once rooted, and after cultivation for two weeks grown in a controlled-environment cabinet or in a greenhouse, flowering was induced, mature seeds were harvested and analyzed for expression of the desaturase or elongase genes by means of lipid analyses as described by way of example in Qiu et al. 2001, J. Biol. Chem. 276, 31561-31566.

b) Generation of Transgenic Linseed Plants

Transgenic linseed plants can be generated for example by the method of Bell et al., 1999, In Vitro Cell. Dev. Biol.-Plant. 35(6):456-465 by means of particle bombardment. Agrobacterial-mediated transformations can be effected for example as described by Mlynarova et al. (1994), Plant Cell Report 13: 282-285.

---

We claim:

1. A vector comprising a polynucleotide comprising a nucleic acid sequence selected from the group consisting of:
   (a) a nucleic acid sequence that has at least 95% identity to the sequence of SEQ ID NO: 1 and
   (b) a nucleic acid sequence which codes for a polypeptide having at least 90% identity to the amino acid sequence of SEQ ID NO: 2;
   wherein the nucleic acid sequences of (a) and (b) code for a polypeptide with desaturase activity.

2. The vector according to claim 1, wherein the polynucleotide consists of RNA or DNA.

3. The vector according to claim 1, wherein the vector is an expression vector.

4. The vector according to claim 1, wherein the vector comprises at least one further polynucleotide which codes for a further enzyme which is involved in the biosynthesis of lipids or fatty acids.

5. A nonhuman host cell comprising the vector according to claim 1.

6. The host cell according to claim 5, wherein the host cell additionally comprises at least one further enzyme which is involved in the biosynthesis of lipids or fatty acids.

7. The host cell according to claim 6, wherein the enzyme is selected from the group consisting of an acyl-CoA dehydrogenase, an acyl-ACP (acyl carrier protein) desaturase, an acyl-ACP thioesterase, a fatty acid acyltransferase, an acyl-CoA:lysophospholipid acyltransferase, a fatty acid synthase, a fatty acid hydroxylase, an acetyl-coenzyme A carboxylase, an acyl-coenzyme A oxidase, a fatty acid desaturase, a fatty acid acetylenase, a lipoxygenase, a triacylglycerol lipase, an allene oxide synthase, a hydroperoxide lyase, a fatty acid elongase, a Δ4-desaturase, a Δ5-desaturase, a Δ6-desaturase, a Δ8-desaturase, a Δ9-desaturase, a Δ12-desaturase, a Δ5-elongase, a Δ6-elongase and a Δ9-elongase.

8. A method of fortifying a food or feed product with a polypeptide with desaturase activity, comprising the steps:
   (a) expressing the vector according to claim 1, in a host cell;
   (b) obtaining, from the host cell, the polypeptide which is encoded by the polynucleotide according to (a); and
   (c) adding the polypeptide to the food or feed product.

9. A transgenic, nonhuman organism comprising the vector according to claim 1.

10. The transgenic, nonhuman organism according to claim 9, wherein the organism is an animal, a plant or a multicellular microorganism.

11. A method for the production of a substance which has the structure shown in the general formula I hereinbelow

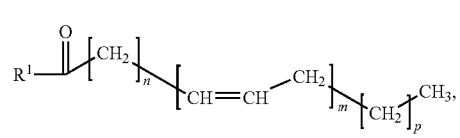

where the variables and substituents are as follows:

$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

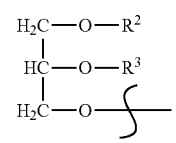

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

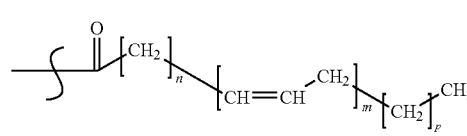

n=2, 3, 4, 5, 6, 7 or 9, m=2, 3, 4, 5 or 6; and p=0 or 3; and wherein the method comprises the cultivation of host cell of claim 5, under conditions which permit the biosynthesis of the substance.

12. A method for the production of a substance which has the structure shown in the general formula I hereinbelow

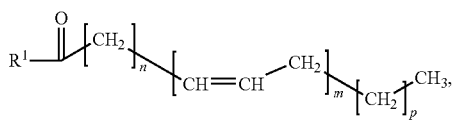

(I)

where the variables and substituents are as follows:
$R^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

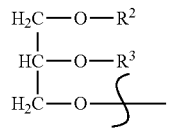

(II)

$R^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated $C_2$-$C_{24}$-alkylcarbonyl, $R^3$=hydrogen, saturated or unsaturated $C_2$-$C_{24}$-alkylcarbonyl, or $R^2$ and $R^3$ independently of one another are a radical of the formula Ia:

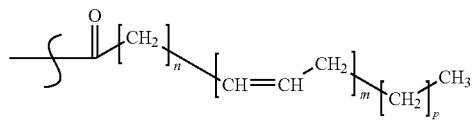

(Ia)

n=2, 3, 4, 5, 6, 7 or 9, m=2, 3, 4, 5 or 6; and p=0 or 3; and
wherein the method comprises the cultivation of a transgenic, nonhuman organism of claim 9, under conditions which permit the biosynthesis of the substance.

13. A method for the production of an oil, lipid or fatty acid composition, comprising the step of the method according to claim 11, and the further step of formulating the substance as an oil, lipid or fatty acid composition.

14. The method according to claim 13, wherein the oil, lipid or fatty acid composition is formulated further to produce a drug, a cosmetic product, a foodstuff, or a feedstuff.

15. The method according to claim 14, wherein the foodstuff is fish food or a food supplement.

* * * * *

SEQUENCE LISTING

<160> NUMBER OF SEQ ID NOS: 35

<210> SEQ ID NO 1
<211> LENGTH: 1368
<212> TYPE: DNA
<213> ORGANISM: Emiliana huxleyi

<400> SEQUENCE: 1

```
atgtcattgg ctgctaaaga tgcagcctcg gcccactcat ccgtcttgga ccctaagtat      60
cacggagcta caaataagtc aagaactgat gcagcagacc ttacagttag ttctatcgac     120
acttctaagg agatgatcat aagggtcgt gtgtatgatg tctctgattt tattaaaagg     180
cacccgggag gaagcattat taaactctcc ttaggttctg atgcaacaga cgcttataac     240
aacttccata ttaggtctaa aaaagcggat aaaatgttga gagctttgcc aagtaggcca     300
gtagcggatg gattcgctag agacgctttg tctgcagact tcgaggccct gagagcccaa     360
ctcgaggccg aaggttactt cgaaccgaat ctgtggcatg tagcttatcg agttgcggaa     420
gtcgttgcta tgtactgggc gggtattaga cttatctggg cgggttattg gttttaagga     480
gccattgtag caggaatagc tcaggggaga tgcggttggc ttcagcatga gggtggtcat     540
tattcgctca caggtaatat taaacttgat cgacacatgc aaatgattat ctatggatta     600
ggttgcggaa tgtccggttg ttattggaga aaccaacata caagcacca tgcgacaccg     660
caaaagttgg gtgcagatcc agaccttcaa acaatgcctc tggttgcgtt ccatggactc     720
atcggtgcta aggctagggg agcaggaaag tcgtggctag catggcaagc tccacttttc     780
tttggaggcg ttatcacaac cctggtatct tttggttggc agttcgtcca acatccaaag     840
cacgcattga gagtaggaaa ccaactcgaa ttaggctata tggctttacg atatgcttta     900
tggtatgcag cattcggtca tcttgggctt ggtggtgctt tcagattgta cgcttttat     960
gtggcagtcg gaggtacata tatcttcacg aactttgcgg tgtctcacac acataaggat    1020
gttgttccac acgataagca tatttcttgg accttgtatt ctgcaaacca taccactaat    1080
caatctaaca cacctctagt caattggtgg atggcctatc tgaatttca aattgaacat    1140
cacctttttcc ctagcatgcc acaatataac catcctaaaa tctgcggaag agtgaaacaa    1200
ttgtttgaaa aacatggcgt agagtacgat gtcagaactt acgcgaagtc aatgcgtgat    1260
acatacgtga atctcttggc tgtgggaaat gcatctcatt cccttcatca gagaaacgag    1320
ggattaacga ctagggagtc tgcggctgtt agagttacag gtcattga                  1368
```

<210> SEQ ID NO 2
<211> LENGTH: 455
<212> TYPE: PRT
<213> ORGANISM: Emiliana huxleyi

<400> SEQUENCE: 2

```
Met Ser Leu Ala Ala Lys Asp Ala Ala Ser Ala His Ser Ser Val Leu
1               5                   10                  15

Asp Pro Lys Tyr His Gly Ala Thr Asn Lys Ser Arg Thr Asp Ala Ala
            20                  25                  30

Asp Leu Thr Val Ser Ser Ile Asp Thr Ser Lys Glu Met Ile Ile Arg
        35                  40                  45
```

```
Gly Arg Val Tyr Asp Val Ser Asp Phe Ile Lys Arg His Pro Gly Gly
     50                  55                  60

Ser Ile Ile Lys Leu Ser Leu Gly Ser Asp Ala Thr Asp Ala Tyr Asn
 65                  70                  75                  80

Asn Phe His Ile Arg Ser Lys Lys Ala Asp Lys Met Leu Arg Ala Leu
                 85                  90                  95

Pro Ser Arg Pro Val Ala Asp Gly Phe Ala Arg Asp Ala Leu Ser Ala
            100                 105                 110

Asp Phe Glu Ala Leu Arg Ala Gln Leu Glu Ala Glu Gly Tyr Phe Glu
        115                 120                 125

Pro Asn Leu Trp His Val Ala Tyr Arg Val Ala Glu Val Val Ala Met
130                 135                 140

Tyr Trp Ala Gly Ile Arg Leu Ile Trp Ala Gly Tyr Trp Phe Leu Gly
145                 150                 155                 160

Ala Ile Val Ala Gly Ile Ala Gln Gly Arg Cys Gly Trp Leu Gln His
                165                 170                 175

Glu Gly Gly His Tyr Ser Leu Thr Gly Asn Ile Lys Leu Asp Arg His
            180                 185                 190

Met Gln Met Ile Ile Tyr Gly Leu Gly Cys Gly Met Ser Gly Cys Tyr
        195                 200                 205

Trp Arg Asn Gln His Asn Lys His His Ala Thr Pro Gln Lys Leu Gly
210                 215                 220

Ala Asp Pro Asp Leu Gln Thr Met Pro Leu Val Ala Phe His Gly Leu
225                 230                 235                 240

Ile Gly Ala Lys Ala Arg Gly Ala Gly Lys Ser Trp Leu Ala Trp Gln
                245                 250                 255

Ala Pro Leu Phe Phe Gly Gly Val Ile Thr Thr Leu Val Ser Phe Gly
            260                 265                 270

Trp Gln Phe Val Gln His Pro Lys His Ala Leu Arg Val Gly Asn Gln
        275                 280                 285

Leu Glu Leu Gly Tyr Met Ala Leu Arg Tyr Ala Leu Trp Tyr Ala Ala
        290                 295                 300

Phe Gly His Leu Gly Leu Gly Gly Ala Phe Arg Leu Tyr Ala Phe Tyr
305                 310                 315                 320

Val Ala Val Gly Gly Thr Tyr Ile Phe Thr Asn Phe Ala Val Ser His
                325                 330                 335

Thr His Lys Asp Val Val Pro His Asp Lys His Ile Ser Trp Thr Leu
            340                 345                 350

Tyr Ser Ala Asn His Thr Thr Asn Gln Ser Asn Thr Pro Leu Val Asn
        355                 360                 365

Trp Trp Met Ala Tyr Leu Asn Phe Gln Ile Glu His His Leu Phe Pro
370                 375                 380

Ser Met Pro Gln Tyr Asn His Pro Lys Ile Cys Gly Arg Val Lys Gln
385                 390                 395                 400

Leu Phe Glu Lys His Gly Val Glu Tyr Asp Val Arg Thr Tyr Ala Lys
                405                 410                 415

Ser Met Arg Asp Thr Tyr Val Asn Leu Leu Ala Val Gly Asn Ala Ser
            420                 425                 430

His Ser Leu His Gln Arg Asn Glu Gly Leu Thr Thr Arg Glu Ser Ala
        435                 440                 445

Ala Val Arg Val Thr Gly His
450                 455
```

<210> SEQ ID NO 3
<211> LENGTH: 1371
<212> TYPE: DNA
<213> ORGANISM: Ostreococcus tauri

<400> SEQUENCE: 3

```
atgtgtgttg agaccgagaa caacgatgga atccctactg tggagatcgc tttcgatgga      60
gagagagaaa gagctgaggc taacgtgaag ttgtctgctg agaagatgga acctgctgct     120
ttggctaaga ccttcgctag aagatacgtg gttatcgagg gagttgagta cgatgtgacc     180
gatttcaaac atcctggagg aaccgtgatt ttctacgctc tctctaacac tggagctgat     240
gctactgagg ctttcaagga gttccaccac agatctagaa aggctaggaa ggcttttggct    300
gctttgcctt ctagacctgc taagaccgct aaagtggatg atgctgagat gctccaggat     360
ttcgctaagt ggagaaagga gttggagagg gacggattct tcaagccttc tcctgctcat     420
gttgcttaca gattcgctga gttggctgct atgtacgctt gggaaccta cttgatgtac      480
gctagatacg ttgtgtcctc tgtgttggtt tacgcttgct cttcggagc tagatgtgga     540
tgggttcaac atgagggagg acattcttct ttgaccggaa acatctggtg ggataagaga    600
atccaagctt tcactgctgg attcggattg ctggatctg agatatgtg aactccatg       660
cacaacaagc accatgctac tcctcaaaaa gtgaggcacg atatggattt ggataccact    720
cctgctgttg ctttcttcaa caccgctgtg aggataata gacctagggg attctctaag    780
tactggctca gattgcaagc ttggaccttc attcctgtga cttctggatt ggtgttgctc    840
ttctggatgt tcttcctcca tccttctaag gctttgaagg gaggaaagta cgaggagctt    900
gtgtggatgt tggctgctca tgtgattaga acctggacca ttaaggctgt tactggattc    960
accgctatgc aatcctacgg actcttcttg gctacttctt gggtttccgg atgctacttg   1020
ttcgctcact tctctacttc tcacacccat ttggatgttg ttcctgctga tgagcatttg   1080
tcttgggtta ggtacgctgt ggatcacacc attgatatcg atccttctca gggatgggtt   1140
aactggttga tgggatactt gaactgccaa gtgattcatc acctcttccc ttctatgcct   1200
caattcagac aacctgaggt gtccagaaga ttcgttgctt tcgctaagaa gtggaacctc   1260
aactacaagg tgatgactta tgctggagct tggaaggcta ctttgggaaa cctcgataat   1320
gtgggaaagc actactacgt gcacggacaa cattctggaa agaccgcttg a            1371
```

<210> SEQ ID NO 4
<211> LENGTH: 456
<212> TYPE: PRT
<213> ORGANISM: Ostreococcus tauri

<400> SEQUENCE: 4

```
Met Cys Val Glu Thr Glu Asn Asn Asp Gly Ile Pro Thr Val Glu Ile
 1               5                  10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95
```

```
Lys Ala Leu Ala Ala Leu Pro Ser Arg Pro Ala Lys Thr Ala Lys Val
            100                 105                 110

Asp Asp Ala Glu Met Leu Gln Asp Phe Ala Lys Trp Arg Lys Glu Leu
        115                 120                 125

Glu Arg Asp Gly Phe Phe Lys Pro Ser Pro Ala His Val Ala Tyr Arg
    130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
            180                 185                 190

Gly Asn Ile Trp Trp Asp Lys Arg Ile Gln Ala Phe Thr Ala Gly Phe
        195                 200                 205

Gly Leu Ala Gly Ser Gly Asp Met Trp Asn Ser Met His Asn Lys His
210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
            260                 265                 270

Val Thr Ser Gly Leu Val Leu Phe Trp Met Phe Phe Leu His Pro
        275                 280                 285

Ser Lys Ala Leu Lys Gly Gly Lys Tyr Glu Glu Leu Val Trp Met Leu
290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
            340                 345                 350

Val Val Pro Ala Asp Glu His Leu Ser Trp Val Arg Tyr Ala Val Asp
        355                 360                 365

His Thr Ile Asp Ile Asp Pro Ser Gln Gly Trp Val Asn Trp Leu Met
370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
            420                 425                 430

Ala Thr Leu Gly Asn Leu Asp Asn Val Gly Lys His Tyr Tyr Val His
        435                 440                 445

Gly Gln His Ser Gly Lys Thr Ala
450                 455
```

<210> SEQ ID NO 5
<211> LENGTH: 1380
<212> TYPE: DNA
<213> ORGANISM: Pythium irregulare

<400> SEQUENCE: 5
atggtggacc tcaagcctgg agtgaagcgc ctggtgagct ggaaggagat ccgcgagcac      60

```
gcgacgcccg cgaccgcgtg gatcgtgatt caccacaagg tctacgacat ctccaagtgg    120
gactcgcacc cggtggctc cgtgatgctc acgcaggccg gcgaggacgc cacggacgcc     180
ttcgcggtct ccacccgtc ctcggcgctc aagctgctcg agcagttcta cgtcggcgac     240
gtggacgaaa cctccaaggc cgagatcgag ggggagccgg cgagcgacga ggagcgcgcg    300
cgccgcgagc gcatcaacga gttcatcgcg tcctaccgcc gtctgcgcgt caaggtcaag    360
ggcatggggc tctacgacgc cagcgcgctc tactacgcgt ggaagctcgt gagcacgttc    420
ggcatcgcgg tgctctcgat ggcgatctgc ttcttcttca acagtttcgc catgtacatg    480
gtcgccggcg tgattatggg gctcttctac cagcagtccg gatggctggc gcacgacttc    540
ttgcacaacc aggtgtgcga gaaccgcacg ctcggcaacc ttatcggctg cctcgtgggc    600
aacgcctggc agggcttcag catgcagtgg tggaagaaca agcacaacct gcaccacgcg    660
gtgccgaacc tgcacagcgc caaggacgag ggcttcatcg gcgacccgga catcgacacc    720
atgccgctgc tggcgtggtc taaggagatg gcgcgcaagg cgttcgagtc ggcgcacggc    780
ccgttcttca tccgcaacca ggcgttccta tacttcccgc tgctgctgct cgcgcgcctg    840
agctggctcg cgcagtcgtt cttctacgtg ttcaccgagt tctcgttcgg catcttcgac    900
aaggtcgagt tcgacggacc ggagaaggcg ggtctgatcg tgcactacat ctggcagctc    960
gcgatcccgt acttctgcaa catgagcctg tttgagggcg tggcatactt cctcatgggc   1020
caggcgtcct gcggcttgct cctggcgctg gtgttcagta ttggccacaa cggcatgtcg   1080
gtgtacgagc gcgaaaccaa gccggacttc tggcagctgc aggtgaccac gacgcgcaac   1140
atccgcgcgt cggtattcat ggactggttc accggtggct tgaactacca gatcgaccat   1200
cacctgttcc cgctcgtgcc gcgccacaac ttgccaaagg tcaacgtgct catcaagtcg   1260
ctatgcaagg agttcgacat cccgttccac gagaccggct tctgggaggg catctacgag   1320
gtcgtggacc acctggcgga catcagcaag gaatttatca ccgagttccc agcgatgtaa   1380
```

<210> SEQ ID NO 6
<211> LENGTH: 459
<212> TYPE: PRT
<213> ORGANISM: Pythium irregulare
<400> SEQUENCE: 6

```
Met Val Asp Leu Lys Pro Gly Val Lys Arg Leu Val Ser Trp Lys Glu
1               5                   10                  15

Ile Arg Glu His Ala Thr Pro Ala Thr Ala Trp Ile Val Ile His His
            20                  25                  30

Lys Val Tyr Asp Ile Ser Lys Trp Asp Ser His Pro Gly Gly Ser Val
        35                  40                  45

Met Leu Thr Gln Ala Gly Glu Asp Ala Thr Asp Ala Phe Ala Val Phe
    50                  55                  60

His Pro Ser Ser Ala Leu Lys Leu Leu Glu Gln Phe Tyr Val Gly Asp
65                  70                  75                  80

Val Asp Glu Thr Ser Lys Ala Glu Ile Glu Gly Pro Ala Ser Asp
                85                  90                  95

Glu Glu Arg Ala Arg Arg Glu Arg Ile Asn Glu Phe Ile Ala Ser Tyr
            100                 105                 110

Arg Arg Leu Arg Val Lys Val Lys Gly Met Gly Leu Tyr Asp Ala Ser
        115                 120                 125

Ala Leu Tyr Tyr Ala Trp Lys Leu Val Ser Thr Phe Gly Ile Ala Val
    130                 135                 140
```

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
            165                 170                 175

Ala His Asp Phe Leu His Asn Gln Val Cys Glu Asn Arg Thr Leu Gly
                180                 185                 190

Asn Leu Ile Gly Cys Leu Val Gly Asn Ala Trp Gln Gly Phe Ser Met
            195                 200                 205

Gln Trp Trp Lys Asn Lys His Asn Leu His His Ala Val Pro Asn Leu
210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
            245                 250                 255

Ser Ala His Gly Pro Phe Phe Ile Arg Asn Gln Ala Phe Leu Tyr Phe
                260                 265                 270

Pro Leu Leu Leu Ala Arg Leu Ser Trp Leu Ala Gln Ser Phe Phe
275                 280                 285

Tyr Val Phe Thr Glu Phe Ser Phe Gly Ile Phe Asp Lys Val Glu Phe
290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
            340                 345                 350

Ser Ile Gly His Asn Gly Met Ser Val Tyr Glu Arg Glu Thr Lys Pro
            355                 360                 365

Asp Phe Trp Gln Leu Gln Val Thr Thr Thr Arg Asn Ile Arg Ala Ser
370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
            420                 425                 430

Gly Phe Trp Glu Gly Ile Tyr Glu Val Val Asp His Leu Ala Asp Ile
            435                 440                 445

Ser Lys Glu Phe Ile Thr Glu Phe Pro Ala Met
    450                 455

<210> SEQ ID NO 7
<211> LENGTH: 873
<212> TYPE: DNA
<213> ORGANISM: Physcomitrella patens

<400> SEQUENCE: 7
atggaggtcg tggagagatt ctacggtgag ttggatggga aggtctcgca gggcgtgaat      60
gcattgctgg gtagttttgg ggtggagttg acgatacgc ccactaccaa aggcttgccc     120
ctcgttgaca gtcccacacc catcgtcctc ggtgtttctg tatacttgac tattgtcatt     180
ggagggcttt tgtggataaa ggccagggat ctgaaaccgc gcgcctcgga gccattttg     240 ctccaagctt tggtgcttgt gcacaacctg ttctgttttg cgctcagtct gtatatgtgc     300
gtgggcatcg cttatcaggc tattacctgg cggtactctc tctggggcaa tgcatacaat     360

```
cctaaacata aagagatggc gattctggta tacttgttct acatgtctaa gtacgtggaa      420
ttcatggata ccgttatcat gatactgaag cgcagcacca ggcaaataag cttcctccac      480
gtttatcatc attcttcaat ttccctcatt tggtgggcta ttgctcatca cgctcctggc      540
ggtgaagcat attggtctgc ggctctgaac tcaggagtgc atgttctcat gtatgcgtat      600
tacttcttgg ctgcctgcct tcgaagtagc ccaaagttaa aaataagta cctttttggg      660 ggcaggtact tgacacaatt ccaaatgttc cagtttatgc tgaacttagt gcaggcttac      720
tacgacatga aaacgaatgc gccatatcca caatggctga tcaagatttt gttctactac      780
atgatctcgt tgctgtttct tttcggcaat ttttacgtac aaaaatacat caaaccctct      840
gacggaaagc aaaagggagc taaaactgag tga                                   873
```

<210> SEQ ID NO 8
<211> LENGTH: 290
<212> TYPE: PRT
<213> ORGANISM: Physcomitrella patens

<400> SEQUENCE: 8

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
                20                  25                  30

Thr Pro Thr Thr Lys Gly Leu Pro Leu Val Asp Ser Pro Thr Pro Ile
            35                  40                  45

Val Leu Gly Val Ser Val Tyr Leu Thr Ile Val Ile Gly Gly Leu Leu
        50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
```

Thr Glu
290

<210> SEQ ID NO 9
<211> LENGTH: 1197
<212> TYPE: DNA
<213> ORGANISM: Phytophtora sojae

<400> SEQUENCE: 9

```
atggctattt tgaaccctga ggctgattct gctgctaacc tcgctactga ttctgaggct     60
aagcaaagac aattggctga ggctggatac actcatgttg agggtgctcc tgctcctttg    120
cctttggagt tgcctcattt ctctctcaga gatctcagag ctgctattcc taagcactgc    180
ttcgagagat cttccgtgac ctccacctac tacatgatca agaacgtgtt gacttgcgct    240
gctttgttct acgctgctac cttcattgat agagctggag ctgctgctta tgttttgtgg    300
cctgtgtact ggttcttcca gggatcttac ttgactggag tgtgggttat cgctcatgag    360
tgtggacatc aggcttattg ctcttctgag gtggtgaaca acttgattgg actcgtgttg    420
cattctgctt tgttggtgcc ttaccactct tggagaatct ctcacagaaa gcaccattcc    480
aacactggat cttgcgagaa cgatgaggtt ttcgttcctg tgaccagatc tgtgttggct    540
tcttcttgga cgagaccttg gaggattct cctctctacc aactctaccg tatcgtgtac    600
atgttggttg ttggatggat gcctggatac ctcttcttca cgctactgg acctactaag    660
tactggggaa agtctaggtc tcacttcaac ccttactccg ctatctatgc tgataggggag    720
agatggatga tcgtgctctc cgatattttc ttggtggcta tgttggctgt tttggctgct    780
ttggtgcaca ctttctcctt caacaccatg gtgaagttct acgtggtgcc ttacttcatt    840
gtgaacgctt acttggtgtt gattacctac ctccaacaca ccgatacata catcccttcat    900
ttcagagagg gagagtggaa ttggttgaga ggagctttgt gcactgtgga tagatcatt    960
ggtccattcc tcgattctgt ggtgcataga atcgtggata cccatgttg ccaccacatc   1020
ttctccaaga tgcctttcta tcattgcgag gaggctacca acgctattaa gcctctcctc   1080
ggaaagttct acttgaagga taccactcct gttcctgttg ctctctggag atcttacacc   1140
cattgcaagt tcgttgagga tgatggaaag gtggtgttct acaagaacaa gctctag     1197
```

<210> SEQ ID NO 10
<211> LENGTH: 398
<212> TYPE: PRT
<213> ORGANISM: Phytophtora sojae

<400> SEQUENCE: 10

Met Ala Ile Leu Asn Pro Glu Ala Asp Ser Ala Ala Asn Leu Ala Thr
1               5                   10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

```
Tyr Val Leu Trp Pro Val Tyr Trp Phe Phe Gln Gly Ser Tyr Leu Thr
                100                 105                 110

Gly Val Trp Val Ile Ala His Glu Cys Gly His Gln Ala Tyr Cys Ser
            115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
    210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Pro Tyr Phe Ile Val Asn Ala Tyr Leu Val Leu Ile
        275                 280                 285

Thr Tyr Leu Gln His Thr Asp Thr Tyr Ile Pro His Phe Arg Glu Gly
    290                 295                 300

Glu Trp Asn Trp Leu Arg Gly Ala Leu Cys Thr Val Asp Arg Ser Phe
305                 310                 315                 320

Gly Pro Phe Leu Asp Ser Val His Arg Ile Val Asp Thr His Val
                325                 330                 335

Cys His His Ile Phe Ser Lys Met Pro Phe Tyr His Cys Glu Glu Ala
            340                 345                 350

Thr Asn Ala Ile Lys Pro Leu Leu Gly Lys Phe Tyr Leu Lys Asp Thr
    355                 360                 365

Thr Pro Val Pro Val Ala Leu Trp Arg Ser Tyr Thr His Cys Lys Phe
370                 375                 380

Val Glu Asp Asp Gly Lys Val Val Phe Tyr Lys Asn Lys Leu
385                 390                 395
```

<210> SEQ ID NO 11
<211> LENGTH: 1086
<212> TYPE: DNA
<213> ORGANISM: Phytophtora infestans

<400> SEQUENCE: 11

```
atggcgacga aggaggcgta tgtgttcccc actctgacgg agatcaagcg gtcgctacct      60
aaagactgtt tcgaggcttc ggtgcctctg tcgctctact acaccgtgcg ttgtctggtg     120
atcgcggtgg ctctaacctt cggtctcaac tacgctcgcg ctctgcccga ggtcgagagc     180
ttctgggctc tggacgccgc actctgcacg ggctacatct gctgcagggg catcgtgttc     240
tggggcttct tcacggtggg ccacgatgcc ggccacggcg ccttctcgcg ctaccacctg     300
cttaacttcg tggtgggcac tttcatgcac tcgctcatcc tcacgccctt cgagtcgtgg     360
aagctcacgc accgtcacca ccacaagaac acgggcaaca ttgaccgtga cgaggtcttc     420
```

```
tacccgcaac gcaaggccga cgaccacccg ctgtctcgca acctgattct ggcgctcggg    480
gcagcgtggc tcgcctattt ggtcgagggc ttccctcctc gtaaggtcaa ccacttcaac    540
ccgttcgagc ctctgttcgt gcgtcaggtg tcagctgtgg taatctctct tctcgcccac    600
ttcttcgtgg ccggactctc catctatctg agcctccagc tgggccttaa gacgatggca    660
atctactact atggacctgt ttttgtgttc ggcagcatgc tggtcattac caccttccta    720
caccacaatg atgaggagac ccatggtac gccgactcgg agtggacgta cgtcaagggc     780
aacctctcgt ccgtggaccg atcgtacggc gcgctcattg acaacctgag ccacaacatc    840
ggcacgcacc agatccacca cctttttccct atcattccgc actacaaact caagaaagcc    900
actgcggcct tccaccaggc tttccctgag ctcgtgcgca agagcgacga gccaattatc    960
aaggctttct tccgggttgg acgtctctac gcaaactacg gcgttgtgga ccaggaggcg   1020
aagctcttca cgctaaagga agccaaggcg gcgaccgagg cggcggccaa gaccaagtcc   1080
acgtaa                                                              1086
```

<210> SEQ ID NO 12
<211> LENGTH: 361
<212> TYPE: PRT
<213> ORGANISM: Phytophtora infestans

<400> SEQUENCE: 12

```
Met Ala Thr Lys Glu Ala Tyr Val Phe Pro Thr Leu Thr Glu Ile Lys
1               5                   10                  15

Arg Ser Leu Pro Lys Asp Cys Phe Glu Ala Ser Val Pro Leu Ser Leu
            20                  25                  30

Tyr Tyr Thr Val Arg Cys Leu Val Ile Ala Val Ala Leu Thr Phe Gly
        35                  40                  45

Leu Asn Tyr Ala Arg Ala Leu Pro Glu Val Glu Ser Phe Trp Ala Leu
    50                  55                  60

Asp Ala Ala Leu Cys Thr Gly Tyr Ile Leu Leu Gln Gly Ile Val Phe
65                  70                  75                  80

Trp Gly Phe Phe Thr Val Gly His Asp Ala Gly His Gly Ala Phe Ser
                85                  90                  95

Arg Tyr His Leu Leu Asn Phe Val Val Gly Thr Phe Met His Ser Leu
            100                 105                 110

Ile Leu Thr Pro Phe Glu Ser Trp Lys Leu Thr His Arg His His His
        115                 120                 125

Lys Asn Thr Gly Asn Ile Asp Arg Asp Glu Val Phe Tyr Pro Gln Arg
    130                 135                 140

Lys Ala Asp Asp His Pro Leu Ser Arg Asn Leu Ile Leu Ala Leu Gly
145                 150                 155                 160

Ala Ala Trp Leu Ala Tyr Leu Val Glu Gly Phe Pro Pro Arg Lys Val
                165                 170                 175

Asn His Phe Asn Pro Phe Glu Pro Leu Phe Val Arg Gln Val Ser Ala
            180                 185                 190

Val Val Ile Ser Leu Leu Ala His Phe Phe Val Ala Gly Leu Ser Ile
        195                 200                 205

Tyr Leu Ser Leu Gln Leu Gly Leu Lys Thr Met Ala Ile Tyr Tyr Tyr
    210                 215                 220

Gly Pro Val Phe Val Phe Gly Ser Met Leu Val Ile Thr Thr Phe Leu
225                 230                 235                 240

His His Asn Asp Glu Glu Thr Pro Trp Tyr Ala Asp Ser Glu Trp Thr
                245                 250                 255
```

Tyr Val Lys Gly Asn Leu Ser Ser Val Asp Arg Ser Tyr Gly Ala Leu
            260                 265                 270

Ile Asp Asn Leu Ser His Asn Ile Gly Thr His Gln Ile His His Leu
        275                 280                 285

Phe Pro Ile Ile Pro His Tyr Lys Leu Lys Ala Thr Ala Ala Phe
    290                 295                 300

His Gln Ala Phe Pro Glu Leu Val Arg Lys Ser Asp Glu Pro Ile Ile
305                 310                 315                 320

Lys Ala Phe Phe Arg Val Gly Arg Leu Tyr Ala Asn Tyr Gly Val Val
                325                 330                 335

Asp Gln Glu Ala Lys Leu Phe Thr Leu Lys Ala Lys Ala Ala Thr
            340                 345                 350

Glu Ala Ala Ala Lys Thr Lys Ser Thr
            355                 360

<210> SEQ ID NO 13
<211> LENGTH: 1176
<212> TYPE: DNA
<213> ORGANISM: Perilla fruticosa

<400> SEQUENCE: 13
atggctgttt cttctggagc taggctttct aagtctggag ctgatggaga agttttcgat     60
ggacagcaac agtacgaggg aattggaaag agagctgctg ataagtttga tcctgctgct    120
cctcctcctt tcaagatcgc tgatatcagg gctgctattc ctgctcattg ctgggttaag    180
aaccccttgga ggagtctttc ttacgttgtg tgggatgttg ctgctgtttt cgctcttctt    240
gctgctgctg tgtacattaa ctcttgggct ttctggcctg tttactggat tgctcaggga    300
actatgttct gggctctttt cgttcttgga cacgattgtg acacggatc tttctctgat     360
aacactactc ttaacaacgt tgtgggacac gttcttcact cttctatcct tgtgccttac    420
cacggatgga gaatctctca taggactcac catcagaacc atggacacgt tgagaaggat    480
gagtcttggg ttccacttcc tgagaacctt tacaagaagc ttgatttctc tactaagttc    540
cttaggtaca agatcccttt ccctatgttc gcttaccctc tttaccttg gtacagatct    600
cctggaaaga ctggatctca cttcaaccct tactctgatc ttttcaagcc taacgagagg    660
ggacttatcg tgacttctac tatgtgttgg gctgctatgg gagtgtttct tctttacgct    720
tctactatcg tgggtcctaa catgatgttc aagctttacg gagtgcctta ccttattttc    780
gtgatgtggc ttgatactgt gacttacctt caccaccacg gatacgataa gaagcttcct    840
tggtacaggt caaaggagtg gtcttacctt agaggaggac ttactactgt ggatcaggat    900
tacggattct tcaacaagat ccaccacgat attggaactc acgtgatcca tcaccttttc    960
cctcagattc ctcactacca ccttgttgag gctactagag aggctaagag ggtgttggga   1020
aactactacc gtgagcctag aaagtctgga cctgtgcctc ttcatcttat ccctgctctt   1080
ttgaagtctc ttggaaggga tcactacgtg tctgataacg gagatatcgt gtactaccag   1140
actgatgatg agcttttccc ttctaagaag atctga                             1176

<210> SEQ ID NO 14
<211> LENGTH: 391
<212> TYPE: PRT
<213> ORGANISM: Perilla fruticosa

<400> SEQUENCE: 14

Met Ala Val Ser Ser Gly Ala Arg Leu Ser Lys Ser Gly Ala Asp Gly

```
                1               5               10              15
              Glu Val Phe Asp Gly Gln Gln Tyr Glu Gly Ile Gly Lys Arg Ala
                              20                  25                  30
              Ala Asp Lys Phe Asp Pro Ala Ala Pro Pro Phe Lys Ile Ala Asp
                              35                  40                  45
              Ile Arg Ala Ala Ile Pro Ala His Cys Trp Val Lys Asn Pro Trp Arg
              50                  55                  60
              Ser Leu Ser Tyr Val Val Trp Asp Val Ala Ala Val Phe Ala Leu Leu
              65                  70                  75                  80
              Ala Ala Ala Val Tyr Ile Asn Ser Trp Ala Phe Trp Pro Val Tyr Trp
                              85                  90                  95
              Ile Ala Gln Gly Thr Met Phe Trp Ala Leu Phe Val Leu Gly His Asp
                              100                 105                 110
              Cys Gly His Gly Ser Phe Ser Asp Asn Thr Thr Leu Asn Asn Val Val
                              115                 120                 125
              Gly His Val Leu His Ser Ser Ile Leu Val Pro Tyr His Gly Trp Arg
                              130                 135                 140
              Ile Ser His Arg Thr His His Gln Asn His Gly His Val Glu Lys Asp
              145                 150                 155                 160
              Glu Ser Trp Val Pro Leu Pro Glu Asn Leu Tyr Lys Lys Leu Asp Phe
                              165                 170                 175
              Ser Thr Lys Phe Leu Arg Tyr Lys Ile Pro Phe Pro Met Phe Ala Tyr
                              180                 185                 190
              Pro Leu Tyr Leu Trp Tyr Arg Ser Pro Gly Lys Thr Gly Ser His Phe
                              195                 200                 205
              Asn Pro Tyr Ser Asp Leu Phe Lys Pro Asn Glu Arg Gly Leu Ile Val
                              210                 215                 220
              Thr Ser Thr Met Cys Trp Ala Ala Met Gly Val Phe Leu Leu Tyr Ala
              225                 230                 235                 240
              Ser Thr Ile Val Gly Pro Asn Met Met Phe Lys Leu Tyr Gly Val Pro
                              245                 250                 255
              Tyr Leu Ile Phe Val Met Trp Leu Asp Thr Val Thr Tyr Leu His His
                              260                 265                 270
              His Gly Tyr Asp Lys Lys Leu Pro Trp Tyr Arg Ser Lys Glu Trp Ser
                              275                 280                 285
              Tyr Leu Arg Gly Gly Leu Thr Thr Val Asp Gln Asp Tyr Gly Phe Phe
                              290                 295                 300
              Asn Lys Ile His His Asp Ile Gly Thr His Val Ile His His Leu Phe
              305                 310                 315                 320
              Pro Gln Ile Pro His Tyr His Leu Val Glu Ala Thr Arg Glu Ala Lys
                              325                 330                 335
              Arg Val Leu Gly Asn Tyr Tyr Arg Glu Pro Arg Lys Ser Gly Pro Val
                              340                 345                 350
              Pro Leu His Leu Ile Pro Ala Leu Leu Lys Ser Leu Gly Arg Asp His
                              355                 360                 365
              Tyr Val Ser Asp Asn Gly Asp Ile Val Tyr Tyr Gln Thr Asp Asp Glu
                              370                 375                 380
              Leu Phe Pro Ser Lys Lys Ile
              385                 390

<210> SEQ ID NO 15
<211> LENGTH: 903
<212> TYPE: DNA
<213> ORGANISM: Ostreococcus tauri
```

<400> SEQUENCE: 15

```
atgtctgctt ctggagcttt gttgcctgct attgctttcg ctgcttacgc ttacgctacc        60
tacgcttatg ctttcgagtg gtctcatgct aacggaatcg ataacgtgga tgctagagag       120
tggattggag ctttgtcttt gagactccct gcaattgcta ccaccatgta cctcttgttc       180
tgccttgtgg gacctagatt gatggctaag agggaggctt ttgatcctaa gggattcatg       240
ctcgcttaca acgcttacca aaccgctttc aacgttgtgg tgctcggaat gttcgctaga       300
gagatctctg gattgggaca acctgtttgg ggatctacta tgccttggag cgataggaag       360
tccttcaaga tttttgttggg agtgtggctc cattacaaca ataagtacct cgagttgttg       420
gatactgtgt tcatggtggc taggaaaaag accaagcagc tctctttctt gcatgtgtac       480
catcatgctt tgttgatttg gcttggtgg cttgtttgtc atctcatggc taccaacgat       540
tgcatcgatg cttatttcgg agctgcttgc aactctttca tccacatcgt gatgtactcc       600
tactacctca tgtctgcttt gggaattaga tgcccttgga agagatatat cacccaggct       660
cagatgttgc aattcgtgat cgtgttcgct catgctgttt tcgtgctcag acaaaagcac       720
tgccctgtta ctttgccttg gcacaaatgt tcgtgatga caaatatgtt ggtgctcttc        780
ggaaacttct acctcaaggc ttactctaac aagtctaggg gagatggagc ttcttctgtt       840
aagcctgctg agactactag agcaccttct gtgagaagaa ccaggtccag gaagatcgat       900
tga                                                                    903
```

<210> SEQ ID NO 16
<211> LENGTH: 300
<212> TYPE: PRT
<213> ORGANISM: Ostreococcus tauri

<400> SEQUENCE: 16

```
Met Ser Ala Ser Gly Ala Leu Leu Pro Ala Ile Ala Phe Ala Ala Tyr
1               5                   10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190
```

```
Phe Ile His Ile Val Met Tyr Ser Tyr Tyr Leu Met Ser Ala Leu Gly
            195                 200                 205

Ile Arg Cys Pro Trp Lys Arg Tyr Ile Thr Gln Ala Gln Met Leu Gln
210                 215                 220

Phe Val Ile Val Phe Ala His Ala Val Phe Val Leu Arg Gln Lys His
225                 230                 235                 240

Cys Pro Val Thr Leu Pro Trp Ala Gln Met Phe Val Met Thr Asn Met
                245                 250                 255

Leu Val Leu Phe Gly Asn Phe Tyr Leu Lys Ala Tyr Ser Asn Lys Ser
                260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
        290                 295                 300

<210> SEQ ID NO 17
<211> LENGTH: 1560
<212> TYPE: DNA
<213> ORGANISM: Thraustochytrium ssp.

<400> SEQUENCE: 17
atgactgttg gatacgatga ggagatccca ttcgagcaag ttagggctca taacaagcca      60
gatgatgctt ggtgtgctat tcatggacac gtgtacgatg ttaccaagtt cgcttctgtt     120
catccaggag gagatattat cttgctcgct gctggaaagg aagctactgt gctctacgag     180
acctaccatg ttagaggagt gtctgatgct gtgctcagaa agtacagaat cggaaagttg     240
ccagatggac aaggaggagc taacgagaag gagaagagaa ccttgtctgg attgtcctct     300
gcttcttact acacctggaa ctccgatttc tacagagtga tgaggagag agttgtggct     360 agattgaagg agagaggaaa ggctagaaga ggaggatacg agttgtggat caaggctttc     420
ttgctccttg ttggattctg gtcctctctt tactggatgt gcaccctcga tccatctttc     480
ggagctatct tggctgctat gtctttggga gtgttcgctg cttttgttgg aacctgcatc     540
caacatgatg gaaaccatgg agctttcgct caatctagat gggttaacaa ggtggcagga     600
tggactttgg atatgatcgg agcttctgga atgacttggg agttccaaca tgtgttggga     660
catcacccat acactaactt gatcgaggag gagaacggat gcaaaaggt gtccggaaag     720 aagatggata ccaagttggc tgatcaagag tctgatccag atgtgttctc cacctaccca     780
atgatgagat tgcatccatg gcatcagaag agatggtatc acaggttcca gcatatctac     840
ggaccattca tcttcggatt catgaccatc aacaaggtgg tgactcaaga tgttggagtg     900
gtgttgagaa agaggctctt ccaaatcgat gctgagtgca gatatgcttc cccaatgtac     960
gttgctaggt tctggatcat gaaggctttg accgtgttgt acatggttgc tctcccatgt    1020
tatatgcaag gaccatggca tggattgaag ctcttcgcta tcgctcattt cacttgcgga    1080
gaggttttgg ctaccatgtt catcgtgaac cacattatcg agggagtgtc ttacgcttct    1140
aaggatgctg ttaagggaac tatggctcca ccaaagacta tgcatggagt gaccccaatg    1200
aacaacacta gaaaggaggt tgaggctgag gcttctaagt ctggagctgt ggttaagtct    1260
gtgccattgg atgattgggc tgctgttcaa tgccaaacct ctgtgaactg gtctgttgga    1320
tcttggttct ggaaccattt ctctggagga ctcaaccatc aaatcgagca tcatctcttc    1380
ccaggattgt ctcacgagac ctactaccac atccaagatg tggttcaatc tacctgtgct    1440
gagtacggag ttccatacca acatgagcca tctttgtgga ctgcttactg gaagatgctc    1500
```
gaacatttga gacaattggg aaacgaggag actcacgagt cttggcaaag agctgcttga    1560

<210> SEQ ID NO 18
<211> LENGTH: 519
<212> TYPE: PRT
<213> ORGANISM: Thraustochytrium ssp.

<400> SEQUENCE: 18

```
Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
    130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365
```

Val Asn His Ile Ile Glu Gly Val Ser Tyr Ala Ser Lys Asp Ala Val
    370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
                405                 410                 415

Val Val Lys Ser Val Pro Leu Asp Asp Trp Ala Ala Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Val Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515

<210> SEQ ID NO 19
<211> LENGTH: 31
<212> TYPE: DNA
<213> ORGANISM: Artificial
<220> FEATURE:
<223> OTHER INFORMATION: Primer

<400> SEQUENCE: 19
gcggccgcgc catggtggac ctcaagcctg g                              31

<210> SEQ ID NO 20
<211> LENGTH: 27
<212> TYPE: DNA
<213> ORGANISM: Artificial
<220> FEATURE:
<223> OTHER INFORMATION: Primer

<400> SEQUENCE: 20
gcggccgtta catcgctggg aactcgg                                    27

<210> SEQ ID NO 21
<211> LENGTH: 33
<212> TYPE: DNA
<213> ORGANISM: Artificial
<220> FEATURE:
<223> OTHER INFORMATION: Primer

<400> SEQUENCE: 21
gcggccgcgc catgtcattg gctgctaaag atg                             33

<210> SEQ ID NO 22
<211> LENGTH: 28
<212> TYPE: DNA
<213> ORGANISM: Artificial
<220> FEATURE:
<223> OTHER INFORMATION: Primer

<400> SEQUENCE: 22
gcggccgtca atgacctgta actctaac                                   28

<210> SEQ ID NO 23
<211> LENGTH: 31
<212> TYPE: DNA
<213> ORGANISM: Artificial
<220> FEATURE:
<223> OTHER INFORMATION: Primer

<400> SEQUENCE: 23
gcggccgcgc catggcgacg aaggaggcgt a        31

<210> SEQ ID NO 24
<211> LENGTH: 31
<212> TYPE: DNA
<213> ORGANISM: Artificial
<220> FEATURE:
<223> OTHER INFORMATION: Primer

<400> SEQUENCE: 24
gcggccgcgt tacgtggact tggtcttggc c        31

<210> SEQ ID NO 25
<211> LENGTH: 32
<212> TYPE: DNA
<213> ORGANISM: Artificial
<220> FEATURE:
<223> OTHER INFORMATION: Primer

<400> SEQUENCE: 25
gcggccgcgc catggaggtc gtggagagat tc       32

<210> SEQ ID NO 26
<211> LENGTH: 28
<212> TYPE: DNA
<213> ORGANISM: Artificial
<220> FEATURE:
<223> OTHER INFORMATION: Primer

<400> SEQUENCE: 26
gcggccgcgt cactcagttt tagctccc            28

<210> SEQ ID NO 27
<211> LENGTH: 30
<212> TYPE: DNA
<213> ORGANISM: Artificial
<220> FEATURE:
<223> OTHER INFORMATION: Primer

<400> SEQUENCE: 27
gcggccgcca tggcgatcct gaacccggag          30

<210> SEQ ID NO 28
<211> LENGTH: 30
<212> TYPE: DNA
<213> ORGANISM: Artificial
<220> FEATURE:
<223> OTHER INFORMATION: Primer

<400> SEQUENCE: 28
gcggccgctt agagcttgtt cttgtagaag          30

<210> SEQ ID NO 29
<211> LENGTH: 29
<212> TYPE: DNA
<213> ORGANISM: Artificial
<220> FEATURE:
<223> OTHER INFORMATION: Primer

```
<400> SEQUENCE: 29
gcggccgcca tggccgtttc ttccggtgc                                        29

<210> SEQ ID NO 30
<211> LENGTH: 30
<212> TYPE: DNA
<213> ORGANISM: Artificial
<220> FEATURE:
<223> OTHER INFORMATION: Primer

<400> SEQUENCE: 30
gcggccgcct aaatctttt ggaaggaaag                                        30

<210> SEQ ID NO 31
<211> LENGTH: 32
<212> TYPE: DNA
<213> ORGANISM: Artificial
<220> FEATURE:
<223> OTHER INFORMATION: Primer

<400> SEQUENCE: 31
gcggccgcgc catgagcgcc tccggtgcgc tg                                    32

<210> SEQ ID NO 32
<211> LENGTH: 23
<212> TYPE: DNA
<213> ORGANISM: Artificial
<220> FEATURE:
<223> OTHER INFORMATION: Primer

<400> SEQUENCE: 32
gcggccgcgt tagtcaattt ttc                                              23

<210> SEQ ID NO 33
<211> LENGTH: 32
<212> TYPE: DNA
<213> ORGANISM: Artificial
<220> FEATURE:
<223> OTHER INFORMATION: Primer

<400> SEQUENCE: 33
gcggccgcgc catgacggtc ggctacgacg ag                                    32

<210> SEQ ID NO 34
<211> LENGTH: 29
<212> TYPE: DNA
<213> ORGANISM: Artificial
<220> FEATURE:
<223> OTHER INFORMATION: Primer

<400> SEQUENCE: 34
gcggccgcgt caggcagcgc gctgccagg                                        29

<210> SEQ ID NO 35
<211> LENGTH: 26755
<212> TYPE: DNA
<213> ORGANISM: Artificial
<220> FEATURE:
<223> OTHER INFORMATION: Plasmid

<400> SEQUENCE: 35
ctatacaaag ttgatagctt ggcgtaatcg atgtaccgat atcaatttaa attggccggc      60
cgagctccct gcaggggggcc cggcgcgcct ctagattaat taaaggcctt agttactaat    120
cagtgatcag attgtcgttt cccgccttca gtttaaacta tcagtgtttg acaggatata    180
```

```
ttggcgggta aacctaagag aaaagagcgt ttattagaat aatcggatat ttaaaagggc    240
gtgaaaaggt ttatccgttc gtccatttgt atgtcaatat ccatgataag tcgcgctgta    300
tgtgtttgtt tgaatattca tggaacgcag tggcggtttt catggcttgt tatgactgtt    360
tttttggggt acagtctatg cctcgggcat ccaagcagca agcgcgttac gccgtgggtc    420
gatgtttgat gttatggagc agcaacgatg ttacgcagca gggcagtcgc cctaaaacaa    480
agttaaacat catgggtgaa gcggtcatcg ccgaggtgtc cacccagctg tcggaagtcg    540
tgggtgtcat cgagcgccac ctcgaaccga ccctcctcgc cgtgcatctg tatggtagcg    600
ccgttgacgg cggccttaag ccccattcgg acatcgacct gcttgtcacc gttaccgtcc    660
gtctcgacga gaccacgcgc cgcgcgctta caacgacct tctggaaacg tccgcctccc    720
ccggcgagag cgaaatcctg cgcgcggttg aggtgacgat tgtggtgcac gatgacatca    780 tccctggcg ctatccggcc aaacgcgaac tccagttcgg cgaatggcag cgtaatgata    840 ttctggcgg tatcttgaa ccggccacca tcgacattga tctggcgatc ctgctcacca    900
aggcccggga gcatagcgtg gccctcgtcg gccccgcggc cgaggaactt ttcgacccgg    960
tgccggaaca ggatctgttc gaagcactga acgagacgct gaccctgtgg aactccccgc   1020
cggattgggc gggcgatgag cgcaatgtgg tccttacgct gagccggatt tggtactcgg   1080
cggttaccgg caagatcgcg ccgaaggatg tcgccgccga ctgggcgatg gagcgccttc   1140
cggcgcaata ccagcccgtg atcctcgaag cgcgccaagc ctatctgggc caagaagaag   1200
accgtctcgc gtcccgggcc gaccagctcg aagaatttgt ccactatgtc aagggcgaga   1260
tcacgaaggt cgttggcaaa taatgtctag ctagaaattc gttcaagccg acgccgcttc   1320
gcggcgcggc ttaactcaag cgttagatgc actaagcaca taattgctca cagccaaact   1380
atcgatgagt tgaaggaccc cgtagaaaag atcaaaggat cttcttgaga tccttttttt   1440
ctgcgcgtaa tctgctgctt gcaaacaaaa aaccaccgc taccagcggt ggtttgtttg   1500
ccggatcaag agctaccaac tcttttttccg aaggtaactg gcttcagcag agcgcagata   1560
ccaaatactg tccttctagt gtagccgtag ttaggccacc acttcaagaa ctctgtagca   1620
ccgcctacat acctcgctct gctaatcctg ttaccagtgg ctgctgccag tggcgataag   1680
tcgtgtctta ccgggttgga ctcaagacga tagttaccgg ataaggcgca gcggtcgggc   1740
tgaacggggg gttcgtgcac acagcccagc ttggagcgaa cgacctacac cgaactgaga   1800
tacctacagc gtgagctatg agaaagcgcc acgcttcccg aagggagaaa ggcggacagg   1860
tatccggtaa cgcgcagggt cggaacagga gagcgcacga gggagcttcc aggggggaaac  1920 gcctggtatc tttatagtcc tgtcgggttt cgccacctct gacttgagcg tcgatttttg   1980
tgatgctcgt caggggggcg gagcctatgg aaaaacgcca gcaacgcggc ctttttacgg   2040
ttcctggcct tttgctggcc ttttgctcac atgttctttc ctgcgttatc ccctgattct   2100
gtggataacc gtattaccgc ctttgagtga gctgataccg ctcgccgcag ccgaacgacc   2160
gagcgcagcg agtcagtgag cgaggaagcg gaagagcgcc tgatgcggta ttttctcctt   2220
acgcatctgt gcggtatttc acaccgcata ggccgcgata ggccgacgcg aagcggcggg   2280
gcgtagggag cgcagcgacc gaagggtagg cgcttttttgc agctcttcgg ctgtgcgctg   2340
gccagacagt tatgcacagg ccaggcgggt tttaagagtt ttaataagtt ttaaagagtt   2400
ttaggcggaa aaatcgcctt ttttctcttt tatatcagtc acttacatgt gtgaccggtt   2460
cccaatgtac ggctttgggt tcccaatgta cgggttccgg ttcccaatgt acggctttgg   2520
```

```
gttcccaatg tacgtgctat ccacaggaaa gagacctttt cgaccttttt cccctgctag   2580
ggcaatttgc cctagcatct gctccgtaca ttaggaaccg gcggatgctt cgccctcgat   2640
caggttgcgg tagcgcatga ctaggatcgg gccagcctgc cccgcctcct ccttcaaatc   2700
gtactccggc aggtcatttg acccgatcag cttgcgcacg gtgaaacaga acttcttgaa   2760
ctctccggcg ctgccactgc gttcgtagat cgtcttgaac aaccatctgg cttctgcctt   2820
gcctgcggcg cggcgtgcca ggcggtagag aaaacggccg atgccggggt cgatcaaaaa   2880
gtaatcgggg tgaaccgtca gcacgtccgg gttcttgcct tctgtgatct cgcggtacat   2940
ccaatcagca agctcgatct cgatgtactc cggccgcccg gtttcgctct ttacgatctt   3000
gtagcggcta atcaaggctt caccctcgga taccgtcacc aggcggccgt tcttggcctt   3060
cttggtacgc tgcatggcaa cgtgcgtggt gtttaaccga atgcaggttt ctaccaggtc   3120
gtctttctgc tttccgccat cggctcgccg gcagaacttg agtacgtccg caacgtgtgg   3180
acggaacacg cggccgggct tgtctcccct cccttcccgg tatcggttca tggattcggt   3240
tagatgggaa accgccatca gtaccaggtc gtaatcccac acactggcca tgccggcggg   3300
gcctgcggaa acctctacgt gcccgtctgg aagctcgtag cggatcacct cgccagctcg   3360
tcggtcacgc ttcgacagac ggaaaacggc cacgtccatg atgctgcgac tatcgcgggt   3420
gcccacgtca tagagcatcg gaacgaaaaa atctggttgc tcgtcgccct tgggcggctt   3480
cctaatcgac ggcgcaccgg ctgccggcgg ttgccgggat tctttgcgga ttcgatcagc   3540
ggccccttgc cacgattcac cggggcgtgc ttctgcctcg atgcgttgcc gctgggcggc   3600
ctgcgcggcc ttcaacttct ccaccaggtc atcacccagc gccgcgccga tttgtaccgg   3660
gccggatggt ttgcgaccgc tcacgccgat tcctcgggct tgggggttcc agtgccattg   3720
cagggccggc agacaaccca gccgcttacg cctggccaac cgcccgttcc tccacacatg   3780
gggcattcca cggcgtcggt gcctggttgt tcttgatttt ccatgccgcc tcctttagcc   3840
gctaaaattc atctactcat ttattcattt gctcatttac tctggtagct gcgcgatgta   3900
ttcagatagc agctcggtaa tggtcttgcc ttggcgtacc gcgtacatct tcagcttggt   3960
gtgatcctcc gccggcaact gaaagttgac ccgcttcatg gctggcgtgt ctgccaggct   4020
ggccaacgtt gcagccttgc tgctgcgtgc gctcggacgg ccggcactta gcgtgtttgt   4080
gcttttgctc atttttctctt tacctcatta actcaaatga gttttgattt aatttcagcg   4140
gccagcgcct ggacctcgcg ggcagcgtcg ccctcgggtt ctgattcaag aacggttgtg   4200
ccggcggcgg cagtgcctgg gtagctcacg cgctgcgtga tacgggactc aagaatgggc   4260
agctcgtacc cggccagcgc ctcggcaacc tcaccgccga tgcgcgtgcc tttgatcgcc   4320
cgcgacacga caaaggccgc ttgtagcctt ccatccgtga cctcaatgcg ctgcttaacc   4380
agctccacca ggtcggcggt ggcccaaatg tcgtaagggc ttggctgcac cggaatcagc   4440
acgaagtcgg ctgccttgat cgcggacaca gccaagtccg ccgcctgggg cgctccgtcg   4500
atcactacga agtcgcgccg gccgatggcc ttcacgtcgc ggtcaatcgt cggcggtcg   4560 atgccgacaa cggttagcgg ttgatcttcc cgcacggccg cccaatcgcg ggcactgccc   4620
tgggatcgaa atcgactaa cagaacatcg gcccgcgcga gttgcagggc gcggctaga   4680 tgggttgcga tggtcgtctt gcctgacccg cctttctggt taagtacagc gataaccttc   4740
atgcgttccc cttgcgtatt tgtttattta ctcatcgcat catatacgca gcgaccgcat   4800
gacgcaagct gttttactca aatacacatc acctttttag atgatcagtg attttgtgcc   4860
gagctgccgg tcggggagct gttggctggc tggtggcagg atatattgtg gtgtaaacaa   4920
```

```
attgacgctt agacaactta ataacacatt gcggacgtct ttaatgtact gaatttagtt    4980
actgatcact gattaagtac tgcgatcgcc tcgacatatt gtttttgttt cacataaatg    5040
tcgttttgga ttattcatgt aatattttaa actaaagtac aattttttgac tactttagtt   5100 tactagttaa gcttttattt ttttgactaa ccattgaatg atgaagagat caacgcatca    5160
tatttacaac ttacatagtc ttttggaagt gtaaattgct aatactacct aaaatatatc    5220
tataattaac taatatttt tcgtcaatta taatagatca attaaaaggc tatcaaaagg     5280
aaaaaaatga aatccacatc ctgccatcat aacctcatgc tggaaaaaga atgaaaaaa     5340 tataaaaaat ttcttttgtt tattaaattt acaactttaa tactagtttc ttttctattt    5400
tttaaaagct tttgtcactt acttaaaaaa aaaaacttt ttgaaatatt cctacttcca     5460
atgtctgatt agtgcttctg gatttccttt ttggatcatg tgaatcctaa atcagaaaaa    5520
ttcatataat acccaattca gtatattttc atacttcaat ttacaagagt tctctatgtt    5580
tttagcttct ttcttttaag ccaaatgttt taagcatctt ttatacatta aaataattta    5640
gtgttgagtt gagattttt ttttttttt ttggatttac ttgttcaaaa tctgaaaaaa      5700
tgtttacaga aggttaaaat gaaccaaaag gcatatcaag ctagattttg aattacccta    5760
tttcatcgta tacacaaaac tgataatgtg gacacagttg attttacttc tcgatgacat    5820
cgtagtttta tttaatttgg aaaccacggc ccatatgagc acatttcaat taaaaaccaa    5880
tggtaagagc attttccatg caagattcga gagatattaa cccagtgact gttaaaacag    5940
cttagaaccc taataacgaa tttcaattac tcaatttacc attcgcattt cgcaataacc    6000
aaactgagcc agtcacaagg agtaaaccga accggattat ttatttataa aatgaaagaa    6060
aggaaaccaa acaacaacag cagtagtagt ctgacgtaaa ccaaaaagca ggcagatcaa    6120
caactaaaag aaactcaaat taccaaaaca aacaggaaat tgcaaactaa gttttttttac   6180 catatgcata caaagaccat aaaaggttct gataatcacc ggtttcatct cgtcgagatt    6240
accctgttat ccctatcagt atttaatccg gccatctcct tccgttatga catcgttgaa    6300
agtgccacca ttcgggatca tcggcaacac atgttcttgg tgcggacaaa tcacatccaa    6360
caggtaaggt cctggtgtat ccagcattgt ctgaatagct tctcggagat ctgctttctt    6420
tgtcaccctc gccgctggaa tcccgcaagc tgctgcaaac agcaacatgt tcgggaatat    6480
ctcgtcctcc tgagccggat ccccgagaaa tgtgtgagct cggttagctt tgtagaaccg    6540
atcttcccat tgcataacca tgccaagatg ctggttgttt aataaaagta ccttcactgg    6600
aagattctct acacgaatag tggctagctc ttgcacattc attataaagc ttccatctcc    6660
gtcaatatcc acaactatcg catcaggggtt agcaacagac gctccaatcg cagcaggaag   6720
tccaaatccc atagctccaa ggcctcctga tgatagccac tgccttggtt tcttgtaatt    6780
gtagaactgc gccgcccaca tttgatgttg cccgacacca gtacttatta tggcttttcc    6840
atcagtcaac tcatcaagga ccttaatcgc atactgtgga ggaatagctt ccccaaacgt    6900
cttaaagctc aacggaaact tctgtttctg tacgttcaac tcattcctcc aaactccaaa    6960
atcaagctta agctcctccg ctcggttctc aagaaccttta ttcatccctt gcaaagccag   7020
cttaacatca ccacacacag acacatgagg agtcttattc ttcccaatct cagccgagtc    7080
aatatcaata tgaacaatct tagccctact agcaaaagcc tcaagcttac ccgtgacacg    7140
atcatcaaac cttaccccaa acgccaacaa caaatcacta tgctccacag cgtaatttgc    7200
atacacagtc ccatgcattc caagcatatg taacgacaac tcatcatcac aaggataaga    7260
```

```
tcccagcccc atcaacgtac tcgcaacagg gatccccgta agctcaacaa acctacccaa      7320
ttcatcgcta gaattcaaac aaccaccacc aacatacaac acaggcttct tagactcaga      7380
aatcaaccta acaatctgct ccaaatgaga atcttccgga ggtttaggca tcctagacat      7440
ataaccaggt aatctcatag cctgttccca attaggaatc gcaagctgtt gttgaatatc      7500
tttaggaaca tcaaccaaaa caggtccagg tctaccagaa gtagctaaaa agaaagcttc      7560
ctcaataatc ctagggatat cttcaacatc catcacaaga tagttatgct tcgtaatcga      7620
acgcgttacc tcaacaatcg gagtctcttg aaacgcatct gtaccaatca tacgacgagg      7680
gacttgtcct gtgattgcta caagaggaac actatctaac aacgcatcgg ctaatccgct      7740
aacgagattt gtagctccgg gacctgaagt ggctatacag atacctggtt tacctgagga      7800
tcgagcgtat ccttctgctg cgaatacacc tccttgttcg tgacgaggaa ggacgttacg      7860
gattgaggaa gagcgggtta aggcttggtg aatctccatt gatgtacctc cagggtaagc      7920
gaatacggtt tctacgcctt gacgttctaa agcttcgacg aggatatcag cgcctttgcg      7980
gggttgatct ggagcgaatc gggagatgaa tgtttcgggt ttggtaggtt tggttggaga      8040
gggagtggtt gtgacattgg tggttgtgtt gagcacggcg gagatggagg agggagagct      8100
ggatttgata ccgcggcggc gggaggagga ggatgatttg ttggggttta gggagaatgg      8160
gagggagaat ctggagattg gtaatggtga tttggaggag gaaggagatg gtttggtgga      8220
gaaggagatc gaagaagatg ttgttgttgt tgttgttgcc gccgccatgg ttcagctgca      8280
catacataac atatcaagat cagaacacac atatacacac acaaatacaa tcaagtcaac      8340
aactccaaaa agtccagatc tacatatata catacgtaaa taacaaaatc atgtaaataa      8400
tcacaatcat gtaatccaga tctatgcaca tatatatata cacaattaat aaaaaaaatg      8460
atataacaga tctatatcta tgtatgtaac aacacaatca gatgagagaa gtgatgtttt      8520
cagatctgta tacatacaaa cacaaacaga tgaacaattg atacgtagat ccatatgtat      8580
acgtacaatt agctacacga ttaaatgaaa aaaatcaacg atttcggatt ggtacacaca      8640
aacgcaacaa tatgaagaaa ttcatatctg attagatata aacataacca cgtgtagata      8700
cacagtcaaa tcaacaaatt tatagcttct aaacggatga gatgaacaag ataaagatat      8760
tcacataagg catacataag ataagcagat taacaaacta gcaataatac atacctaatt      8820
aaaacaagga ataacagaga gagagagaga gagagagatt taccttgaaa atgaagagga      8880
gaagagagga tttcttaaaa ttgggggtag agaaagaaag atgatgaatt gtgagaaagg      8940
agagatagaa gggggggttg tatatatagg ctgtagaaga ttattttttgt gtttgaggcg      9000 gtgaaggaag aggggatctg actatgacac gtttgcggtt acgtatttcg ataggagtct      9060
ttcaacgctt aacgccgtta ctctatatga ccgtttgggc cgtaacgggg ccgtttgtta      9120
acgctgatgt tgattctttt ctttctttct tcttcctttt tttaaagaag caattgtaca      9180
atcgttgcta gctgtcaaac ggataaattcg gatacggata tgcctatatt catatccgta      9240 attttttggat tcgaattttc ccctctaggg ataacagggt aatggatcta tattgttttt      9300
gtttcacata aatgtcgttt tggattattc atgtaatatt ttaaactaaa gtacaatttt      9360
tgactacttt agtttactag ttaagctttt attttttttga ctaaccattg aatgatgaag      9420
agatcaacgc atcatattta caacttacat agtcttttgg aagtgtaaat tgctaatact      9480
acctaaaata tatctataat taactaatat tttttcgtca attataatag atcaattaaa      9540
aggctatcaa aaggaaaaaa atgaaatcca catcctgcca tcataacctc atgctggaaa      9600
aagaaatgaa aaaatataaa aaatttcttt tgtttattaa atttacaact ttaatactag      9660
```

```
tttcttttct attttttaaa agcttttgtc acttacttaa aaaaaaaaaa cttttgaaa      9720 tattcctact tccaatgtct gattagtgct tctggatttc cttttggat catgtgaatc       9780 ctaaatcaga aaaattcata taatacccaa ttcagtatat tttcatactt caatttacaa     9840
gagttctcta tgttttagc ttcttcttt taagccaaat gttttaagca tcttttatac       9900
attaaaataa tttagtgttg agttgagatt ttttttttt tttttggat ttacttgttc       9960 aaaatctgaa aaatgttta cagaaggtta aatgaacca aaaggcatat caagctagat      10020
tttgaattac cctatttcat cgtatacaca aaactgataa tgtggacaca gttgatttta    10080
cttctcgatg acatcgtagt tttatttaat ttggaaacca cggcccatat gagcacattt    10140
caattaaaaa ccaatggtaa gagcattttc catgcaagat tcgagagata ttaacccagt    10200
gactgttaaa acagcttaga accctaataa cgaatttcaa ttactcaatt taccattcgc    10260
atttcgcaat aaccaaactg agccagtcac aaggagtaaa ccgaaccgga ttatttattt    10320
ataaaatgaa agaaaggaaa ccaaacaaca acagcagtag tagtctgacg taaaccaaaa    10380
agcaggcaga tcaacaacta aaagaaactc aaattaccaa aacaaacagg aaattgcaaa    10440
ctaagttttt ttaccatatg catacaaaga ccataaaagg ttctgataat caccggtttc    10500
atctcagatc cgcgatcgcc aattgacgcg tactagtgta caagcttgcg gccgcgaatt    10560
cggtacatcc ggccagtgaa ttatcaacta tgtataataa agttgggtac cggcctatta    10620
ggccacggtc cgtacagtgt tgccacaat cagtaaattg aacggagaat attattcata     10680
aaaatacgat agtaacgggt gatatattca ttagaatgaa ccgaaaccgg cggtaaggat    10740
ctgagctaca catgctcagg ttttttacaa cgtgcacaac agaattgaaa gcaaatatca    10800
tgcgatcata ggcgtctcgc atatctcatt aaagcagcaa tcaattatta attaatcaat    10860
gacctgtaac tctaacagcc gcagactccc tagtcgttaa tccctcgttt ctctgatgaa    10920
gggaatgaga tgcatttccc acagccaaga gattcacgta tgtatcacgc attgacttcg    10980
cgtaagttct gacatcgtac tctacgccat gttttcaaa caattgtttc actcttccgc     11040
agattttagg atggttatat tgtggcatgc tagggaaaag gtgatgttca atttgaaaat    11100
tcagataggc catccaccaa ttgactagag gtgtgttaga ttgattagtg gtatggtttg    11160
cagaatacaa ggtccaagaa atatgcttat cgtgtggaac aacatcctta tgtgtgtgag    11220
acaccgcaaa gttcgtgaag atatatgtac ctccgactgc cacataaaaa gcgtacaatc    11280
tgaaagcacc accaagccca agatgaccga atgctgcata ccataaagca tatcgtaaag    11340
ccatatagcc taattcgagt tggtttccta ctctcaatgc gtgctttgga tgttggacga    11400
actgccaacc aaaagatacc agggttgtga taacgcctcc aaagaaaagt ggagcttgcc    11460
atgctagcca cgactttcct gctcccctag ccttagcacc gatgagtcca tggaacgcaa    11520
ccagaggcat tgtttgaagg tctggatctg cacccaactt ttgcggtgtc gcatggtgct    11580
tgttatgttg gttctccaa taacaaccgg acattccgca acctaatcca tagataatca    11640
tttgcatgtg tcgatcaagt ttaatattac ctgtgagcga ataatgacca ccctcatgct    11700
gaagccaacc gcatctcccc tgagctattc ctgctacaat ggctcctaaa accaataac    11760 ccgcccagat aagtctaata cccgcccagt acatagcaac gacttccgca actcgataag    11820
ctacatgcca cagattcggt tcgaagtaac cttcggcctc gagttgggct ctcagggcct    11880
cgaagtctgc agacaaagcg tctctagcga atccatccgc tactggccta cttggcaaag    11940
ctctcaacat tttatccgct ttttagacc taatatggaa gttgttataa gcgtctgttg      12000
```

```
catcagaacc taaggagagt ttaataatgc ttcctcccgg gtgcctttta ataaaatcag   12060
agacatcata cacacgaccc cttatgatca tctccttaga agtgtcgata gaactaactg   12120
taaggtctgc tgcatcagtt cttgacttat ttgtagctcc gtgatactta gggtccaaga   12180
cggatgagtg ggccgaggct gcatctttag cagccaatga catggaaggc gcggaggtgt   12240
gagagtgagt tgtgagttgt gtggtgggtt tggtgagatt ggggatggtg ggtttatata   12300
gtggagactg aggaatgggg tcgtgagtgt taactttgca tgggctacac gtgggttctt   12360
ttgggcttac acgtagtatt attcatgcaa atgcagccaa tacatatacg gtattttaat   12420
aatgtgtggg aatacaatat gccgagtatt ttactaattt tggcaatgac aagtgtacat   12480
ttggattatc ttacttggcc tctcttgctt taatttggat tatttttatt ctcttacctt   12540
ggccgttcat attcacatcc ctaaaggcaa gacagaattg aatggtggcc aaaaattaaa   12600
acgatggata tgacctacat agtgtaggat caattaacgt cgaaggaaaa tactgattct   12660
attaggggtg agagttgatc ggttaattat ccaatacatg ccgttggtta attaggatta   12720
tataaaaaat cgatcatcta ttagaatcga ttacggttaa ataggtataa aaatggagag   12780
aattgaatca gttataaatt tgttttcagt taaaatattt ctatgatctt caatcgattt   12840
cggtatttta tactcaacat ggaaaaaatt tcaaatgtat ttcttctaaa agcaaaagaa   12900
tctataaaaa ctatcatttt atccaaaaca ccaaaatagt cttttacaat cttttacagc   12960
cttcacataa acgaaaacaa aagtgaacaa tttcttttta cagcctttac accaaaaaga   13020
ctacgatgaa ctatgataaa atttcataat ctaaaaacat taatgaggta aagactctct   13080
caaatgggat attcttcgaa aatttttcata atcgaacgat atacttgaat ttgcaactca   13140
tgaccgaaat tgtcccaatc cataatactc tttgacaccc tatcagatcc caacgttgtc   13200 cctggttttcg aaaccaccat ttcaaacatg aacatatcac aaaataaaca tttagacacc   13260
aaatatctgc taatggccgg cctaacctgc aggatacaag tgcgcacaga ctagcggccg   13320
ctaatcccgg gaattaccgg tagtaggcgc cttgttttag actgaatata acacaacgat   13380
tatatagccg ctgtctttgt ttgaagagaa tggactacat gctgaaaaat agtgatacaa   13440
gaatcgttgt tttaatgcta aaatgaccat ctcgtgattt aacttttctg gaccaatgat   13500
tgtaaagttt tttttagaga ggtggtgata aacatatatt gattttgaa atgaatagag   13560 ttagaaagta agaaaaatac aataaaaatg ttaaataatg ttgtagaaat agaaatggaa   13620
gagaagtgta aagaaattta aataaaaatt agatgggaga gtaagttagt ttatattgat   13680
ttgttttgtg gttagtttat ctatgttata cttttaactt ataataatcc tttccatcat   13740
taagcaattt ttaaaaatga cataattta aaattatgaa gtaataattg gcatggtgaa   13800
taatagacag tgtaaatggt gtaaatatat gagctcccat tttatttatt gctcccattt   13860
tatttatttt agtttgtgtg acagatgaac attattagga ggaaaggtat aagcagggtt   13920
taactgtcac agggaaggtg gttttgggag tcttagttaa ttaatcagat cttcttagaa   13980
gggaaaagct catcatcagt ctggtagtac acgatatctc cgttatcaga cacgtagtga   14040
tcccttccaa gagacttcaa aagagcaggg ataagatgaa gaggcacagg tccagacttt   14100
ctaggctcac ggtagtagtt tcccaacacc ctcttagcct ctctagtagc ctcaacaagg   14160
tggtagtgag gaatctgagg gaaaaggtga tggatcacgt gagttccaat atcgtggtgg   14220
atcttgttga agaatccgta atcctgatcc acagtagtaa gtcctcctct aaggtaagac   14280
cactcctttg acctgtacca aggaagcttc ttatcgtatc cgtggtggtg aaggtaagtc   14340
acagtatcaa gccacatcac gaaaataagg taaggcactc cgtaaagctt gaacatcatg   14400
```

```
ttaggaccca cgatagtaga agcgtaaaga agaaacactc ccatagcagc ccaacacata   14460
gtagaagtca cgataagtcc cctctcgtta ggcttgaaaa gatcagagta agggttgaag   14520
tgagatccag tctttccagg agatctgtac caaaggtaaa gagggtaagc gaacataggg   14580
aaagggatct tgtacctaag gaacttagta gagaaatcaa gcttcttgta aaggttctca   14640
ggaagtggaa cccaagactc atccttctca acgtgtccat ggttctgatg gtgagtccta   14700
tgagagattc tccatccgtg gtaaggcaca aggatagaag agtgaagaac gtgtcccaca   14760
acgttgttaa gagtagtgtt atcagagaaa gatccgtgtc cacaatcgtg tccaagaacg   14820
aaaagagccc agaacatagt tccctgagca atccagtaaa caggccagaa agcccaagag   14880
ttaatgtaca cagcagcagc aagaagagcg aaaacagcag caacatccca cacaacgtaa   14940
gaaagactcc tccaagggtt cttaacccag caatgagcag gaatagcagc cctgatatca   15000
gcgatcttga aaggaggagg agcagcagga tcaaacttat cagcagctct ctttccaatt   15060
ccctcgtact gttgctgtcc atcgaaaact tctccatcag ctccagactt agaaagccta   15120
gctccagaag aaacagccat ggtggatccg gcgcgccggt catgcattca tgcattaacc   15180
atcactctct tctctatttta tacaacaaca aatgcaaaat cttccaact tttttctttc   15240 attttattat tcaactccaa attaacaatt attaaacaac gatggcaatg catccacgtc   15300
atcaaaaaag tatatgaaat aattagttta aatttaaata gatatttatg gagagaagcg   15360
gtttggcagg tagcaatggg aagtgagagg agtgctgagg tggcagtgtg catggccagt   15420
aggctcataa tgagaagagg tgggagctga ggtggcagca tgcatgccca gtggtgtcat   15480
catgggaaga ggaaggagct cacgtggcaa catgcatggc gagttgtgtc atagtgaaaa   15540
aaccaaagtc gaaagtgaca tgagacatgt gtggagagga gggagctgag gtggcagcgt   15600
gcatggtgag ttgtgtcatg tggggaatct aaaattctaa tttgattttc ccttttttat   15660
ttaattgtat atattatata tattccctag tttatcctta tttatttttac tctgttgtga   15720 actacaatga ttgtactaca tacatgacta aatgatcaca caggtgtgag aggatctgaa   15780
tgactttaga atgttttttt aaaattatat tttttaaata tttgtatttc tataaactct   15840
aatcatgtat tagaatgttt tgaaaaactc taagttttta caaaaatata tgtataacat   15900
atattgttat aattagatgt ttttttgtgt gtgttatatt taatgatatc aaaacatttc   15960
atccttatga taacctgacg gtagtgggtt tattgtgttt ctcgtgtgta cttttttttg   16020
tttaattcta acttcaagac ttaactaaaa gtttctaata agatgtttaa caaaattgtt   16080
ttcttgaaat cttgtctctg agtggtgctc atgactagaa aacctaatta caattattat   16140
attaaaagtt taagtctctt atattattat tacagaaaca aagagataag gacattttttt  16200 ttaatctttt ttcttcctta ccttcctttaa tctcaaatga aacataaatt tgttttgtta   16260
actgttgccc ctttgtctgg tgatgaggaa ataacacatt ttctatagaa ggatcctggc   16320
cggcctagta gatttaaatt ggccttagtg gccaagcttg gcgtaatcat ggccactttg   16380
tacaagaaag ctgggtggta ccggcctatt aggccacggt ccgtacagtg tttgccattg   16440
atgcatgttg tcaatcaatt ggcaagtcat aaaatgcatt aaaaaatatt ttcatactca   16500
actacaaatc catgagtata actataatta taaagcaatg attagaatct gacaaggatt   16560
ctggaaaatt acataaagga aagttcataa atgtctaaaa cacaagagga catacttgta   16620
ttcagtaaca tttgcagctt ttctaggtct gaaaatatat ttgttgccta gtgaataagc   16680
ataatggtac aactacaagt gttttactcc tcatattaac ttcggtcatt agaggccacg   16740
```

-continued

```
atttgacaca ttttactca aaacaaatg tttgcatatc tcttataatt tcaaattcaa    16800
cacacaacaa ataagagaaa aaacaaataa tattaatttg agaatgaaca aaaggaccat   16860
atcattcatt aactcttctc catccatttc catttcacag ttcgatagcg aaaaccgaat   16920
aaaaaacaca gtaaattaca agcacaacaa atggtacaag aaaaacagtt ttcccaatgc   16980
cataatactc gaaccaatca attattaatt aactagagct tgttcttgta gaacaccacc   17040
tttccatcat cctcaacgaa cttgcaatgg gtgtaagatc tccagagagc aacaggaaca   17100
ggagtggtat ccttcaagta gaactttccg aggagaggct taatagcgtt ggtagcctcc   17160
tcgcaatgat agaaaggcat cttggagaag atgtggtggc aaacatgggt atccacgatt   17220
ctatgcacca cagaatcgag gaatggacca aatgatctat ccacagtgca caaagctcct   17280
ctcaaccaat tccactctcc ctctctgaaa tgagggatgt aggtatcggt gtgttggagg   17340
taggtaatca acaccaagta agcgttcaca atgaagtaag gcaccacgta gaacttcacc   17400
atggtgttga aggagaaagt gtgcaccaaa gcagccaaaa cagccaacat agccaccaag   17460
aaaatatcgg agagcacgat catccatctc tccctatcag catagatagc ggagtaaggg   17520
ttgaagtgag acctagactt tccccagtac ttagtaggtc cagtagcgtt gaagaagagg   17580
tatccaggca tccatccaac aaccaacatg tacacgatac ggtagagttg gtagagagga   17640
gaatcctcca aggtctcgtt ccaagaagaa gccaacacag atctggtcac aggaacgaaa   17700
acctcatcgt tctcgcaaga tccagtgttg gaatggtgct ttctgtgaga gattctccaa   17760
gagtggtaag gcaccaacaa agcagaatgc aacacgagtc caatcaagtt gttcaccacc   17820
tcagaagagc aataagcctg atgtccacac tcatgagcga taacccacac tccagtcaag   17880
taagatccct ggaagaacca gtacacaggc cacaaaacat aagcagcagc tccagctcta   17940
tcaatgaagg tagcagcgta gaacaaagca gcgcaagtca acacgttctt gatcatgtag   18000
taggtggagg tcacgaaaga tctctcgaag cagtgcttag gaatagcagc tctgagatct   18060
ctgagagaga aatgaggcaa ctccaaaggc aaaggagcag gagcaccctc aacatgagtg   18120
tatccagcct cagccaattg tctttgctta gcctcagaat cagtagcgag gttagcagca   18180
gaatcagcct cagggttcaa aatagccatg gcggatccgg cgcggtgttt ttaatcttgt   18240
ttgtattgat gagttttggt ttgagtaaag agtgaagccg atgagttaat ttataggcta   18300
taaaggagat ttgcatggcg atcacgtgta ataatgcatg cacgcatgtg attgtatgtg   18360
tgtgctgtga gagagaagct cttaggtgtt tgaagggagt gacaagtggc gaagaaaaac   18420
aattctccgc ggctgcatgc tatgtgtaac gtgtagctaa tgttctggca tggcatctta   18480
tgaacgattc ttttaaaaa caaggtaaaa acttaacttc ataaaattaa aaaaaaaacg   18540
tttactaagt tggtttaaaa ggggatgaga gtctataaat tttggaggta gtgccgttgg   18600
gaatataaat tgggagctta atcagaatta tagaagttaa agttgattta gtcacggtca   18660
atataaattg ggaatttgag tcaaaatctt ccaaattcgg aatccgtctt gttacacccg   18720
gtggatagga gccgaacggt ttgaaaatac ttgaaatgtg gatgcaggtg caggctggtt   18780
taattttatg ttgaatggat acatgtcaat cgaatttgag ttataggtac acattttact   18840
ctgatactaa aatgtaacat ttgtctcaag aatgggtagg tcatccttat ggccggccta   18900
acctgcagga tacaagtgcg cacagactag cggccgctaa tcccgggaat taccggtagt   18960
aggcgccatt gatgcatgtt gtcaatcaat tggcaagtca taaatgcat taaaaaatat   19020
tttcatactc aactacaaat ccatgagtat aactataatt ataaagcaat gattagaatc   19080
tgacaaggat tctggaaaat tacataaagg aaagttcata aatgtctaaa acacaagagg   19140
```

```
acatacttgt attcagtaac atttgcagct tttctaggtc tgaaaatata tttgttgcct    19200
agtgaataag cataatggta caactacaag tgttttactc ctcatattaa cttcggtcat    19260
tagaggccac gatttgacac attttttactc aaaacaaaat gtttgcatat ctcttataat   19320
ttcaaattca acacacaaca aataagagaa aaaacaaata atattaattt gagaatgaac    19380
aaaaggacca tatcattcat taactcttct ccatccattt ccatttcaca gttcgatagc    19440
gaaaaccgaa taaaaaacac agtaaattac aagcacaaca aatggtacaa gaaaaacagt    19500
tttcccaatg ccataatact cgaactcagg tagacttggt cttagcagca gcttcagtag    19560
cagccttagc ctccttcaaa gtgaagagct tagcctcttg atcaaccact ccgtagttag    19620
catacaacct tcccactctg aagaaagcct tgatgattgg ctcatcggac tttctcacaa    19680
gctctgggaa agcttggtgg aaagcagcag tagccttctt gagcttgtag tgtgggataa    19740
ttgggaagag gtggtggatc tggtgagttc cgatgttgtg ggagaggtta tcgatgagag    19800
caccgtaaga tctatccaca gaggacaagt ttcccttcac gtaagtccac tcagaatcag    19860
cataccatgg agtctcctca tcgttgtggt gcaagaaggt ggtaatcacc aacatagatc    19920
cgaacacgaa aactggtccg tagtagtaga tagccatggt cttaagtccc aactggagag    19980
acaagtagat agagagtcca gcaacgaaga agtgagcgag caaagagata accacagcgg    20040
acacttgtct cacaaaaagt ggctcgaatg ggttgaagtg gttcaccttt cttggtggga    20100
atccctccac caaataagca agccaagcag ctcccaaagc caagatcaag ttcctggaca    20160
atgggtgatc atcagccttt ctctgtgggt agaacacctc atctctatcg atgtttccgg    20220
tgttcttgtg gtggtgtctg tgggtcaact tccaagactc gaatgggtc aagatgagag    20280
agtgcatgaa ggttcccaca acgaagttca agaggtggta tctagagaaa gctccgtgtc    20340
cagcatcgtg tccaacagtg aagaatcccc agaacacaat tccctggagg aggatatatc    20400
cagtgcacaa agcagcatcc aaagcccaga aagactcaac ctctggcaaa gctctagcgt    20460
agttcaatcc gaaggtcaaa gccacagcaa taaccaagca tctcacagtg tagtagagag    20520
acaaaggcac agaagcctcg aagcaatcct ttgggagaga tctcttgatc tcggtgagag    20580
ttgggaaaac gtaagcctcc tttgtagcca tggttgtttt taatcttgtt tgtattgatg    20640
agttttggtt tgagtaaaga gtgaagccga tgagttaatt tataggctat aaaggagatt    20700
tgcatggcga tcacgtgtaa taatgcatgc acgcatgtga ttgtatgtgt gtgctgtgag    20760
agagaagctc ttaggtgttt gaagggagtg acaagtggcg aagaaaaaca attctccgcg    20820
gctgcatgct atgtgtaacg tgtagctaat gttctggcat ggcatcttat gaacgattct    20880
ttttaaaaac aaggtaaaaa cttaacttca taaaattaaa aaaaaaacgt ttactaagtt    20940
ggtttaaaag gggatgagag tctataaatt ttggaggtag tgccgttggg aatataaatt    21000
gggagcttaa tcagaattat agaagttaaa gttgatttag tcacggtcaa tataaattgg    21060
gaatttgagt caaaatcttc caaattcgga atccgtcttg ttacacccgg tggataggag    21120
ccgaacggtt tgaaaatact tgaaatgtgg atgcaggtgc aggctggttt aattttatgt    21180
tgaatggata catgtcaatc gaatttgagt tataggtaca cattttactc tgatactaaa    21240
atgtaacatt tgtctcaaga atgggtaggt catccttatg gccggcctag tagatttaaa    21300
ttggccttag tggccaagct tggcgtaatc atggagcctg cttttttgta caaacttggg    21360
taccggccta ttaggccacg gtccgtacag tgtttgcccc ccactccgcc ctacactcgt    21420
atatatatgc ctaaacctgc cccgttcctc atatgtgata ttattatttc attattaggt    21480
```

```
ataagatagt aaacgataag gaaagacaat ttattgagaa agccatgcta aaatatagat   21540
agatatacct tagcaggtgt ttattttaca acataacata acatagtagc tagccagcag   21600
gcaggctaaa acatagtata gtctatctgc aggggggtacg gtcgaggcgg ccttaattaa   21660
ttatcaagcg gtcttttccag aatgttgtcc gtgcacgtag tagtgctttc ccacattatc   21720
gaggtttccc aaagtagcct tccaagctcc agcataagtc atcaccttgt agttgaggtt   21780
ccacttctta gcgaaagcaa cgaatcttct ggacacctca ggttgtctga attgaggcat   21840
agaagggaag aggtgatgaa tcacttggca gttcaagtat cccatcaacc agttaaccca   21900
tccctgagaa ggatcgatat caatggtgtg atccacagcg tacctaaccc aagacaaatg   21960
ctcatcagca ggaacaacat ccaaatgggt gtgagaagta gagaagtgag cgaacaagta   22020
gcatccggaa acccaagaag tagccaagaa gagtccgtag gattgcatag cggtgaatcc   22080
agtaacagcc ttaatggtcc aggttctaat cacatgagca gccaacatcc acacaagctc   22140
ctcgtacttt cctcccttca aagcttagaa ggatggagg aagaacatcc agaagagcaa   22200
caccaatcca gaagtcacag gaatgaaggt ccaagcttgc aatctgagcc agtacttaga   22260 gaatcccta ggtctattat cctccacagc ggtgttgaag aaagcaacag caggagtggt   22320
atccaaatcc atatcgtgcc tcactttttg aggagtagca tggtgcttgt tgtgcatgga   22380
gttccacata tctccagatc cagccaatcc gaatccagca gtgaaagctt ggattctctt   22440
atcccaccag atgtttccgg tcaaagaaga atgtcctccc tcatgttgaa cccatccaca   22500
tctagctccg aagaagcaag cgtaaaccaa cacagaggac acaacgtatc tagcgtacat   22560
caagtaggtt cccaaagcgt acatagcagc caactcagcg aatctgtaag caacatgagc   22620
aggagaaggc ttgaagaatc cgtccctctc caactccttt ctccacttag cgaaatcctg   22680
gagcatctca gcatcatcca ctttagcggt cttagcaggt ctagaaggca aagcagccaa   22740
agccttccta gcctttctag atctgtggtg gaactccttg aaagcctcag tagcatcagc   22800
tccagtgtta gagagagcgt agaaaatcac ggttcctcca ggatgtttga aatcggtcac   22860
atcgtactca actccctcga taaccacgta tcttctagcg aaggtcttag ccaaagcagc   22920
aggttccatc ttctcagcag acaacttcac gttagcctca gctctttctc tctctccatc   22980
gaaagcgatc tccacagtag ggattccatc gttgttctcg gtctcaacac acatggtggc   23040
gcggttcagc ttgatcgctc tattaattag ttcattgttt tatacgtgaa gaaaagaaa    23100 gagacggaat atatggcaaa aaacatgcaa ggggacgtgt gttaacatac gtgtcttatg   23160
actaattatt cgtagtggca gtttctacca tctggaaatg gaattgatat acacaggcca   23220
gcaagacact ctagcttacc atagagcatt ttcatgcaca cttttttaaa agacaaagga   23280
agtatattaa tagatggtca taattctgaa tgttttatta cctttaacat tccaacaagg   23340
ttaaaaccaa tgtttcaaga tgtcaatgtg tccttcacaa actcatatat tgaattacta   23400
gtttgaccaa gatataaggg ttaactctaa aacataagaa aatatgacac aaatataaaa   23460
taaatatcag atatattgag agatctcaaa attattaaga ataaaatatc taagtattaa   23520
tattgttggt ggtattctaa aggtgacagg tgataaatta tattattgta aaatttaaaa   23580
taagagaata ttttatatt gttgtaaaat ttaaaataag agaatatttt tgagttacgt    23640
tttgtactaa atttctattg atggattttg gactttgaaa taccataatt tctattcaat   23700
tcattacaca tttttttcca gcatacaatt tagcattaca aagttttat ataggcttga    23760 agaaaagtaa catagaaaac aataattcaa aaatcaagac gaggactatt tggttttctc   23820
aatcttaatg atacaacttt atcataattt taaataagga caataattat aatgtgatga   23880
```

```
ttacaatttt cttataatac ttactaaagg tagtggtggt tacaacacat taattttaac  23940
actcccctt aatgtgttgc tctttaactc ccattacttc tctaagttgt taaaatcttc   24000
ctctttgtag tattttagta aaagtgtctg taagttgctc ttatgaactg cagaaaggta  24060
actgcacatt tccttcttca atcactcttc gaatgaagtg gtgttttatg ttaatgtgtc  24120
tagtccgact atgaaaaaca ggattctttg tgttgtacta caaattttt cctctcagtc   24180
ttcaagaatt ttctcataag atcttccatg acatcaagtt tgcagcactg atacatcaat  24240
ttaggtttgg aattggcaca agagcaaaat ggtcaattgc acactgaaaa gtcaaacttt  24300
gacttttgca tcaacatcaa atttcaagaa tcacatttca tcaagacatg ttagaatatg  24360
aagtttgttt tattaagaaa gtcaaaagtc aagtttgctt tggaaaagtc aaaattctaa  24420
acacttagaa atttttctaa ctgttaagaa atatgacaag ttcagaactt ctggccagat  24480
tttcaccatg atgcaagttg attctggaag aacttctgac acaagagttg tagatttcaa  24540
tgagatctaa gacattgcgg aacagaactt ctcttaaaaa tgatgggatt tcaagttata  24600
aatctttgaa gacacgtcca tgaaactgaa gtactcaata aattttgggc cttcccaaga  24660
cggaatttgg ttagaacttc tggagcagtt ttcacgtagg ttcaatcaga gtttgcaaga  24720
gtaattcaaa gaaagtctac aaagcatgtt acaagctttc tgaaaagtct tagaactcct  24780
tcagaacatg ttggaacaga gagattcaaa gatcagaagt tggatacagt ccgggccgtc  24840
gatggccggc ctaacctgca ggatacaagt gcgcacagac tagcggccgc taatcccggg  24900
aattaccggt agtaggcgcc ctgaattaac gccgaattaa ttcggggat ctggatttta    24960
gtactggatt ttggttttag gaattagaaa ttttattgat agaagtattt tacaaataca  25020
aatacatact aagggtttct tatatgctca acacatgagc gaaaccctat aggaaccta   25080
attcccttat ctgggaacta ctcacacatt attatggaga aactcgagct tgtcgagata  25140
tcgggctaga gcgccaccgc ggtggagatc tgcggcctta attaatcaag cggacttctt  25200
cttctttgga gccatgtagg attgcacgaa gaactgagcg aagaggaaga aaagggagag  25260
aatgtacacg aagtacacga tggtgattct gagggaaacc ttatcgcatc cgtggaaaac  25320
caagtaggta gcttgggaca tcatgatggt gaattgcaag agttggaaag cggtcaaaga  25380
tgacttccac cagattggca aagactttcc ggtcttagaa tccttggtgt gcatgcagat  25440
gaagtagtag gtgtacatca cggtgtgaat gaatccgttg aggaggatgg tcaagaagat  25500
atctccatcg tagagcacgt tagcgttcaa ccagtagaag aggaagatgg tggtatgatg  25560
gtacacgtgc aagaaagaga gttgtctcca cttctttccg agcacaatga agatggtatc  25620
ccagaaatcc cacactttgg agatgtagaa gagccagagc aagttagcaa ctggtggatc  25680
gttcacgttg aagtggttgc atggcataac ggtgtatccg ttcctataag cgaggaatcc  25740
agcctcaaca gtcatgtaag cgcagaggaa gatttgagac acgttgtaga ggaacttgat  25800
agggtatggg tccatagctg ggagagattg catcacagca gatcccaaga tcacgaaagc  25860
gatgtagatg agagcaatgg tgatagcgga tctgaaatcg cacaaccacc aatcctccct  25920
atcagctctg aactttccat ctggatcact ccaatcgatg atagcagctc caatcttatc  25980
catagcagcg ttataagcat ccatggtact ggctatgaag aaattataat cgtgtaaaac  26040
ttagtgagtg tgtatgaatg aaagtattgc aaaatcctca ttatatagac tacatgcata  26100
actagttgca tgtaaatttg tagttttctt cattattgca tcctccaagt ggatgtcatg  26160
gttttacaca tggcttccat gcaaatcatt tccaaaatat ttttaaactt tccacagggc  26220
```

| | | | | | |
|---|---|---|---|---|---|
| atccatgcat | gcacctcaaa | acttgtgtgt | ggtaacattg | ttgtcttgaa | aaattactaa | 26280
| accttttgtc | cacgtgacgt | tcatgcacct | caaatcttgt | gtggtaccat | tattatcctc | 26340
| aagaattatt | gaatgtttgg | tgtatatgcc | atccatgcag | cattgcaaca | attaaatctc | 26400
| caaaccttgt | ggtaccatat | tcactcactt | taattctcct | atagtagaaa | tattagcaaa | 26460
| tatttacatt | tccagttgat | tagtatatgt | atttagaaga | caaaaataat | ttagaatcaa | 26520
| ttaatcaact | tgcaaattgc | taagtgttgg | caaacgttag | cataaaaggt | gttataaatt | 26580
| tagtaccaaa | tataaaaatt | tatcgcaaat | caaatacata | acacacatag | taaaacaaaa | 26640
| acaaattaca | agggtttaga | cgtttagtgg | caatgtgtaa | atttgctgca | gtggccggcc | 26700
| tagtagattt | aaattggcct | tagtggccaa | gcttggcgta | atcatggcaa | ctttt | 26755